(12) United States Patent
Pesaro et al.

(10) Patent No.: US 12,350,357 B2
(45) Date of Patent: Jul. 8, 2025

(54) ACTIVE AGENTS FOR SKIN AND HAIR CARE WITH PHYSICOCHEMICAL MODIFYING PROPERTIES

(71) Applicant: SYMRISE AG, Holzminden (DE)

(72) Inventors: Manuel Pesaro, Romanel-sur-Lausanne (DE); Sabine Lange, Holzminden (DE); Ricarda Kräling, Holzminden (DE)

(73) Assignee: SYMRISE AG, Holzminden (DE)

( * ) Notice: Subject to any disclaimer, the term of this patent is extended or adjusted under 35 U.S.C. 154(b) by 848 days.

(21) Appl. No.: 17/428,327

(22) PCT Filed: Jan. 22, 2020

(86) PCT No.: PCT/EP2020/051499
§ 371 (c)(1),
(2) Date: Aug. 4, 2021

(87) PCT Pub. No.: WO2020/160904
PCT Pub. Date: Aug. 13, 2020

(65) Prior Publication Data
US 2022/0105016 A1    Apr. 7, 2022

(30) Foreign Application Priority Data
Feb. 4, 2019   (WO) ................. PCT/EP2019/052582

(51) Int. Cl.
*A61K 8/37*    (2006.01)
*A61Q 5/00*    (2006.01)
(Continued)

(52) U.S. Cl.
CPC .............. *A61K 8/375* (2013.01); *A61Q 5/006* (2013.01); *A61Q 5/02* (2013.01); *A61Q 19/007* (2013.01); *A61Q 19/10* (2013.01); *A61K 2800/30* (2013.01)

(58) Field of Classification Search
CPC .... A61K 8/375; A61K 2800/30; A61Q 5/006; A61Q 5/02; A61Q 19/007; A61Q 19/10
See application file for complete search history.

(56) References Cited

FOREIGN PATENT DOCUMENTS

| CN | 101641313 A | 2/2010 |
|---|---|---|
| EP | 2548448 A1 | 1/2013 |

(Continued)

OTHER PUBLICATIONS

Database GNPD [Online] Mintel; May 22, 2017 (May 22, 2017), anonymous: "Volume+ Shampoo", retrieved from www.gnpd.com (Year: 2017).*

(Continued)

*Primary Examiner* — Deborah D Carr
(74) *Attorney, Agent, or Firm* — POLSINELLI PC

(57) ABSTRACT

The present invention primarily relates to the use of a fatty acid ester or of a mixture of two or more fatty acid esters or of a mixture comprising one or more fatty acid esters, wherein the fatty acid ester or one, two, three or more, preferably all, of the fatty acid ester(s) is/are selected from the group consisting of 3-hydroxypropyl caprylate, 3-hydroxypropyl undecylenate and glyceryl monoundecylenate, for modifying the physicochemical properties of a skin care product. The present invention further relates to methods for modifying the physicochemical properties of a skin care product as well as to methods for manufacturing a skin care product and to particular skin care products.

20 Claims, 6 Drawing Sheets

(51) Int. Cl.
  *A61Q 5/02* (2006.01)
  *A61Q 19/00* (2006.01)
  *A61Q 19/10* (2006.01)

(56) References Cited

FOREIGN PATENT DOCUMENTS

| | | | |
|---|---|---|---|
| JP | H09110648 | * | 4/1997 |
| JP | H09110648 A | | 4/1997 |
| JP | 2002114669 A | | 4/2002 |
| JP | 2002114670 A | | 4/2002 |
| JP | 2018123129 A | * | 8/2018 |
| WO | 2007095262 A2 | | 8/2007 |
| WO | 2011101239 A2 | | 8/2011 |
| WO | WO-2018012021 A1 | * | 1/2018 |
| WO | 2019007792 A1 | | 1/2019 |

OTHER PUBLICATIONS

"Technical data TRIstat ECO", , Jul. 30, 2013 (Jul. 30, 2013), pp. 1-13, . Retrieved from the Internet: URL:http://www.innovadex.com/documents/1190990.pdf?bs=612&b=319722&st=20 (Year: 2013).*
International Search Report and Written Opinion issued on Apr. 22, 2020 for corresponding PCT Application No. PCT/EP2020/051499.
Database GNPD; Mintel; "Volume + Shampoo," 2017; pp. 1-4 XP055630494.
"Technical data TRIstat ECO," 2013; pp. 1-13 XP055122754.
Brazilian Office Action issued on Aug. 11, 2024 for corresponding Brazilian Application No. BR 11 2021 015349-7.
"Soft-Run Body Exfoliant Scrub for Gel", GNPD, Mintel, (Jan. 7, 2019), Database accession No. 6187283, URL: www.gnpd.com XP055630497.

* cited by examiner

ACTIVE AGENTS FOR SKIN AND HAIR CARE WITH PHYSICOCHEMICAL MODIFYING PROPERTIES

CROSS-REFERENCE TO RELATED APPLICATIONS

This application is a national stage application (under 35 U.S.C. § 371) of PCT/EP2020/051499, filed Jan. 22, 2020, which claims benefit of PCT Application No. PCT/EP2019/052582, filed Feb. 4, 2019, which are incorporated herein by reference in their entireties.

FIELD OF THE INVENTION

The present invention primarily relates to the use of a fatty acid ester or of a mixture as defined herein for modifying the physicochemical properties of a skin care product. The present invention further relates to methods for modifying the physicochemical properties of a skin care product as well as to methods for manufacturing a skin care product and to particular skin care products.

Further aspects of the present invention will arise from the description below, in particular from the examples, as well as from the attached patent claims.

BACKGROUND

*Malassezia* is a genus of fungi and is naturally found on the skin surfaces of many animals, including humans. As the fungus requires fat to grow, it is most common in areas with many sebaceous glands, i.e. on the scalp, face, and upper part of the body. However, when the fungus grows too rapidly, the natural renewal of cells is disturbed and, for example, dandruff appears on the scalp along with an itching sensation.

It is also well known that substances for care of the skin, particularly the scalp, are used in particular formulations such as, for example, shampoos or gels (e.g. aqueous or aqueous/ethanolic/glycolic based shampoos or gels). Positive physicochemical properties of an active agent, such as e.g. of a topical antifungal agent against dandruff, in these formulations are highly desirable, since they facilitate the manufacture of the formulations and may be experienced in a positive way by the end user. Such positive physicochemical properties of an active agent are e.g. the ability to increase the viscosity or the foam volume or the foam stability of a formulation.

None of the typically used topical antifungal agents, such as e.g. climbazole, zinc pyrithione and piroctone olamine, display any such positive physicochemical properties in skin care formulations.

In DE 42 37 367 A1 fatty acid esters are described as antimycotic agents. These esters are preferably selected from the group of hexyl laurate, isopropyl stearate, glyceryl monolaurate, caprylic acid tryglyceride and capric acid tryglyceride. No physicochemical properties of the active agents are disclosed.

DE 42 34 188 A1 relates to ethoxylated and propoxylated organic compounds as antimycotic agents in cosmetics. No physicochemical properties of the active agents are disclosed.

DE 10 2004 046 603 A1 describes substance mixtures comprising fatty acid esters of polyols and salts of short chain fatty acids to counteract microorganisms. Again, DE 10 2004 046 603 A1 does not disclose any physicochemical properties of the active agents.

SU 1286204 A1 discloses the use of a mixture of mono- (50-60%), di- (30-35%) and triesters (10-15%) of glycerol and undecylenic acid to give antimicrobial properties to a cosmetic base. It also discloses that the mixture combines well with other ingredients of cosmetic products and shampoos.

DE 33 14 786 A1 discloses a mixture with antimycotic activity comprising mono and/or di-10-undecylenic acid glyceryl esters. The mixtures are used in the treatment of nasal cavity mycosis and onychomycosis. It does not disclose any physicochemical properties of the active agents.

In WO 2006/054110 A2, esters of 1,2,3-propanetriol with one or more C11 to C24 fatty acids are described, wherein at least one fatty acid has at least one double bond. The application field for these substances is the treatment of chronic inflammatory disorders.

WO 2007/095262 A2 discloses 1,3-propanediol esters for the purpose of dissolving botanical extracts, fragrance concentrates and oils.

It was thus an object of the present invention to provide skin care agents that impart positive physicochemical properties to a skin care formulation. Moreover, it was an object of the present invention to provide certain skin care formulations, such as e.g. (anti-dandruff) shampoos, with particularly positive physicochemical properties.

DETAILED DESCRIPTION OF THE INVENTION

Figure 1:
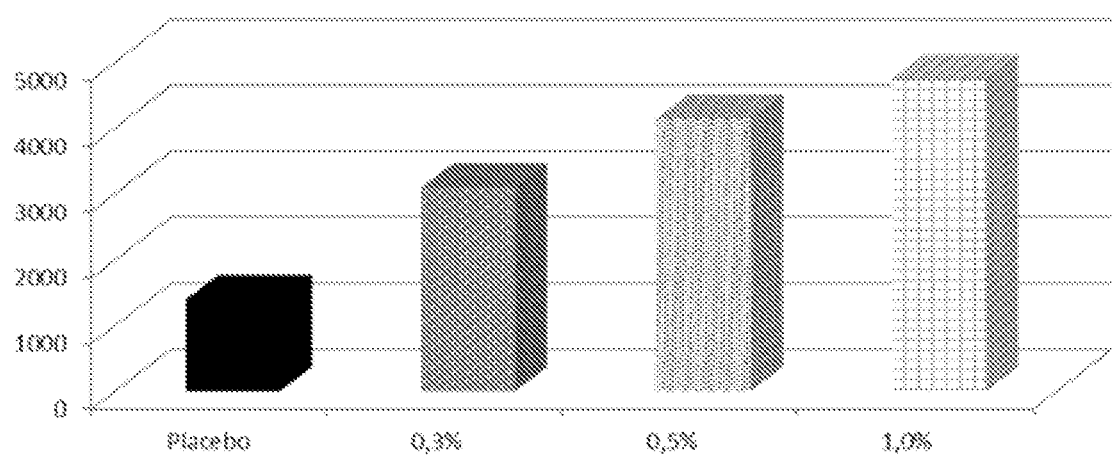
FIG. 1 shows the viscosity in η [mPas] (y-axis) of shampoos comprising 0, 0.3, 0.5 or 1.0 wt.-% of 3-hydroxypropyl caprylate versus placebo.

According to a first aspect of the present invention, the stated object is achieved by the use of a fatty acid ester or of a mixture of two or more fatty acid esters or of a mixture comprising one or more fatty acid esters, wherein the fatty acid ester or one, two or more, preferably all, of the fatty acid ester(s) is/are selected from the group consisting of 3-hydroxypropyl caprylate, 3-hydroxypropyl undecylenate and glyceryl monoundecylenate, for modifying the physicochemical properties of a skin care product.

Within the framework of the present text, a modification of the physicochemical properties of a skin care product, preferably for a scalp care product, relates to a modification of one, more or all characteristics selected from the group consisting of viscosity, foam stability and foam volume of a skin care product, preferably for a scalp care product. Preferred and particularly advantageous modifications of the physicochemical properties of a skin care product, preferably for a scalp care product, according to the present invention will be described below.

Caprylate refers to an ester of caprylic acid (CAS Registry Number of caprylic acid: 124-07-2; also known as octanoic acid) and undecylenate refers to an ester of 10-undecylenic acid (CAS Registry Number of 10-undecylenic acid: 112-38-9; also known as 10-undecenoic acid).

3-Hydroxypropyl caprylate refers to the monoester of the alcohol 1,3-propanediol (CAS Registry Number: 504-63-2) with caprylic acid and 3-hydroxypropyl undecylenate refers to the monoester of the alcohol 1,3-propanediol with 10-undecylenic acid.

A preferred embodiment of the present invention relates to the use of a fatty acid ester or of a mixture of two or more fatty acid esters or of a mixture comprising one or more fatty acid esters, wherein the fatty acid ester or one, two or three, preferably all, of the fatty acid ester(s) is/are selected from the group consisting of 3-hydroxypropyl caprylate, 3-hydroxypropyl undecylenate, and glyceryl monoundecylenate, for modifying the physicochemical properties of a skin care product.

A particularly preferred embodiment of the invention relates to the use of a fatty acid ester or of mixture of two or more fatty acid esters or of a mixture comprising one or more fatty acid esters, wherein the fatty acid ester or one or two, preferably all, of the fatty acid ester(s) is/are selected from the group consisting of 3-hydroxypropyl caprylate and 3-hydroxypropyl undecylenate, for modifying the physicochemical properties of a skin care product.

A preferred embodiment of the invention relates to the use of 3-hydroxypropyl caprylate or of 3-hydroxypropyl undecylenate or of glyceryl monoundecylenate or of a mixture comprising 3-hydroxypropyl caprylate or comprising 3-hydroxypropyl undecylenate or comprising glyceryl monoundecylenate for modifying the physicochemical properties of a skin care product.

Another preferred embodiment of the invention relates to the use of a mixture of 3-hydroxypropyl caprylate and 3-hydroxypropyl undecylenate, or of glyceryl monocaprylate and 3-hydroxypropyl undecylenate, or of 3-hydroxypropyl caprylate and glyceryl monoundecylenate, or of glyceryl monocaprylate and glyceryl monoundecylenate, or of 3-hydroxypropyl caprylate and glyceryl monocaprylate, or to the use of a mixture comprising 3-hydroxypropyl caprylate and 3-hydroxypropyl undecylenate, or glyceryl monocaprylate and 3-hydroxypropyl undecylenate, or 3-hydroxypropyl caprylate and glyceryl monoundecylenate, or glyceryl monocaprylate and glyceryl monoundecylenate, or 3-hydroxypropyl caprylate and glyceryl monocaprylate for modifying the physicochemical properties of a skin care product.

Another preferred embodiment of the invention relates to the use of a mixture of 3-hydroxypropyl caprylate, glyceryl monocaprylate and 3-hydroxypropyl undecylenate, or to the use of a mixture comprising 3-hydroxypropyl caprylate, glyceryl monocaprylate and 3-hydroxypropyl undecylenate for modifying the physicochemical properties of a skin care product.

Another preferred embodiment of the invention relates to the use of a mixture of 3-hydroxypropyl caprylate, glyceryl monocaprylate, 3-hydroxypropyl undecylenate and glyceryl monoundecylenate, or to the use of a mixture comprising 3-hydroxypropyl caprylate, glyceryl monocaprylate, 3-hydroxypropyl undecylenate and glyceryl monoundecylenate for modifying the physicochemical properties of a skin care product.

Another preferred embodiment relates to the use of a fatty acid ester or mixture as defined herein, wherein the total amount of said fatty acid or mixture comprised in the skin care product as defined herein is from 0.01 to 5 wt.-%, more preferably from 0.05 to 2 wt.-%, most preferably from 0.1 to 1 wt.-%, relative to the total weight of said skin care product.

It was surprisingly found that the fatty acid esters or mixtures as defined herein do not only show excellent antimycotic activity against dandruff-causing *Malassezia* spp., but also are able to significantly alter the physicochemical properties of skin care products such as e.g. surfactant based formulation (anti-dandruff) shampoos.

Thus, a preferred embodiment of the invention relates to the use as defined herein, wherein the skin care product is a product selected from the group consisting of leave-on skin care product, preferably oil in water emulsion or aqueous formulation or aqueous and/or ethanolic and/or glycolic-based formulation or water in oil emulsion, and rinse-off skin care product, preferably shampoo, more preferably anti-dandruff shampoo, surfactant-based cleansing formulation, preferably micellar water, or shower gel.

Another preferred embodiment relates to the use as defined herein, wherein the skin care product is a soap, preferably a bar soap or syndet soap (solid or liquid appearance).

Preferably, the modified skin care product is a rinse-off skin care product, preferably a shampoo, more preferably an anti-dandruff shampoo, or a shower gel. Also preferred is a soap, preferably a bar soap or syndet soap (solid or liquid appearance).

Another preferred embodiment of the invention relates to the use as defined herein, wherein the modification of the physicochemical properties is an increase of the viscosity or of the foam volume or of the foam stability of the skin care product, preferably of a shampoo.

It is particularly advantageous to increase the viscosity of a skin care product, because it enables the thickening of the formulation even into a gel-like state of the formulation, if desired. A skin care product that does not run off the user's hand during application is preferred by the consumers since it facilitates handling of the product and avoids spillage of the product during handling. The viscosity of a skin care product can be measured as described in the examples further below.

It is also advantageous to increase the foam volume of certain skin care products, particularly of rinse-off skin care products such as e.g. (anti-dandruff) shampoos or shower gels, because a higher foam volume facilitates the cleansing/treatment of the skin and/or hair by the user. The foam volume of a skin care product can be determined as described in the examples further below.

Usually, the viscosity of a skin care product is assured or increased by the addition of certain thickeners and the foam volume and foam stability of a skin care product is assured or increased by the addition of certain foaming agents. However, it was surprisingly found during the studies underlying the present invention that the use of a fatty acid ester or of a mixture as defined herein enables an increase of the viscosity or of the foam volume or of the foam stability of a skin care product. Thus, its use enables a reduction or even complete omission of other thickeners and/or foaming agents in the skin care formulation, which in turn facilitates the formulation process and saves production time and costs.

Another preferred embodiment of the invention relates to the use as defined herein, wherein the fatty acid ester or mixture as defined herein are further used to avoid dandruff and/or to reduce the amount of dandruff on human skin, preferably on human scalp.

Within the framework of the present text, the term "avoiding dandruff on human skin, preferably on human scalp" relates to a preventive measure where the first occurrence or reoccurrence of dandruff on a defined area of human skin, preferably of human scalp, is avoided by applying the fatty acid esters or mixtures as defined herein once or repeatedly to said defined area of human skin. As a result, no dandruff is visible on said defined area of the human skin when inspected by naked human eye.

Within the framework of the present text, the term "reducing the amount of dandruff on human skin, preferably on human scalp" relates to a measure where the total amount of dandruff on a defined area of human skin, preferably of human scalp, as observed by naked human eye is reduced by more than 10, 20, 30, 40 50, 60, 70, 80 or 90% after one-off or repeated treatment of said defined area with the fatty acid esters or mixtures as defined herein.

Another preferred embodiment of the invention relates to the use as defined herein, wherein the skin care product is sulfate-free and/or comprises sodium cocoyl isethionate, sodium cocoamphoacetate, sodium cocoyl glutamate, sodium methyl cocoyl taurate, sodium cocoyl isethionate, sodium cocoamphoacetate, sodium cocoyl glutamate, and sodium methyl cocoyl taurate, cocamide MIPA, disodium cocoyl glutamate, disodium lauryl sulfosuccinate, lauroyl/myristoyl methyl glucamide, sodium C14-C16 olefin sulfonate, sodium cocoamphoacetate, sodium cocoyl alaninate, sodium cocoyl glutamate, sodium cocoyl glycinate, sodium cocoyl isethionate, sodium laureth-5 carboxylate, sodium laureth-6 carboxylate, sodium lauroyl glutamate, sodium lauroyl lactylate, sodium lauroyl methyl isethionate, coco-glucoside, decyl glucoside, lauryl glucoside, cocamide MEA, cocoamidopropyl betaine, coco betaine, glycol distearate, laureth-4, isostearamide MIPA, lauryl hydroxysultaine, PEG-200 hydrogenated glyceryl palmate, PEG-7 glyceryl cocoate, PEG-4 rapeseedamide, PEG-40 hydrogenated castor oil, trideceth-9, and/or sodium lauroyl sarcosinate. The most commonly used sulfate compounds within the cosmetic industry are sodium laureth sulfate, sodium lauryl sulfate, and ammonium laureth sulfate. They are widely used in combinations with other surfactants to reduce irritation. Especially for color-treated, dry hair & dry scalp there is a tendency to use mild sulfate free formulations. However, very often these formulations tend to poor foaming properties vs sulfate based formulations. Additionally, sulfate based shampoos can easily thickened by sodium chloride, which does not work well with sulfate free surfactants. Increasing the viscosity is therefore a further challenge for sulfate free formulations. Surprisingly, it has been found that the fatty acid esters or mixtures as defined herein even lead to an increase of the viscosity, the foam volume and the foam stability of a sulfate-free skin care product.

Another aspect of the present invention relates to a method for modifying the physicochemical properties of a skin care product comprising or consisting of the following steps:
(i) providing the ingredients of a skin care product or a skin care product (apart from the substance(s) provided in step (ii)),
(ii) providing a fatty acid ester or a mixture of two or more fatty acid esters or a mixture comprising one or more fatty acid esters, wherein the fatty acid ester or one, two or more, preferably all, of the fatty acid ester(s) is/are selected from the group consisting of 3-hydroxypropyl caprylate, 3-hydroxypropyl undecylenate and glyceryl monoundecylenate,
(iii) mixing the components of steps (i) and (ii).

A preferred embodiment of the present invention relates to a method as defined herein, wherein the fatty acid ester or one, two or three, preferably all, of the fatty acid ester(s) provided as fatty acid ester or mixture of two or more fatty acid esters or mixture comprising one or more fatty acid esters in step (ii) is/are selected from the group consisting of 3-hydroxypropyl caprylate and 3-hydroxypropyl undecylenate.

Another preferred embodiment of the present invention relates to a method as defined herein, wherein the fatty acid ester or one, two or three, preferably all, of the fatty acid ester(s) provided as fatty acid ester or mixture of two or more fatty acid esters or mixture comprising one or more fatty acid esters in step (ii) is/are selected from the group consisting of 3-hydroxypropyl caprylate, 3-hydroxypropyl undecylenate and glyceryl monoundecylenate.

Another preferred embodiment of the present invention relates to a method as defined herein, wherein the fatty acid ester or one or two, preferably all, of the fatty acid ester(s) provided as fatty acid ester or mixture of two or more fatty acid esters or mixture comprising one or more fatty acid esters in step (ii) is/are selected from the group consisting of 3-hydroxypropyl caprylate and 3-hydroxypropyl undecylenate.

Another preferred embodiment of the present invention relates to a method as defined herein, wherein the fatty acid ester provided in step (ii) is 3-hydroxypropyl caprylate or 3-hydroxypropyl undecylenate or glyceryl monoundecylenate.

Another preferred embodiment of the present invention relates to a method as defined herein, wherein the mixture comprising one or more fatty acid esters provided in step (ii) comprises 3-hydroxypropyl caprylate or 3-hydroxypropyl undecylenate or glyceryl monoundecylenate.

Another preferred embodiment of the present invention relates to a method as defined herein, wherein the mixture of two or more fatty acid esters provided in step (ii) is a mixture of 3-hydroxypropyl caprylate and 3-hydroxypropyl undecylenate, or of glyceryl monocaprylate and 3-hydroxypropyl undecylenate, or of 3-hydroxypropyl caprylate and glyceryl monoundecylenate, or of glyceryl monocaprylate and glyceryl monoundecylenate, or of 3-hydroxypropyl caprylate and glyceryl monocaprylate.

Another preferred embodiment of the present invention relates to a method as defined herein, wherein the mixture comprising one or more fatty acid esters provided in step (ii) comprises 3-hydroxypropyl caprylate and 3-hydroxypropyl undecylenate, or glyceryl monocaprylate and 3-hydroxypropyl undecylenate, or 3-hydroxypropyl caprylate and glyceryl monoundecylenate, or glyceryl monocaprylate and glyceryl monoundecylenate, or 3-hydroxypropyl caprylate and glyceryl monocaprylate.

Another preferred embodiment of the present invention relates to a method as defined herein, wherein the mixture of two or more fatty acid esters provided in step (ii) is a mixture of 3-hydroxypropyl caprylate, glyceryl monocaprylate and 3-hydroxypropyl undecylenate.

Another preferred embodiment of the present invention relates to a method as defined herein, wherein the mixture comprising one or more fatty acid esters provided in step (ii) comprises 3-hydroxypropyl caprylate, glyceryl monocaprylate and 3-hydroxypropyl undecylenate.

Another preferred embodiment of the present invention relates to a method as defined herein, wherein the mixture of two or more fatty acid esters provided in step (ii) is a mixture of 3-hydroxypropyl caprylate, glyceryl monocaprylate, 3-hydroxypropyl undecylenate and glyceryl monoundecylenate.

Another preferred embodiment of the present invention relates to a method as defined herein, wherein the mixture comprising one or more fatty acid esters provided in step (ii) comprises 3-hydroxypropyl caprylate, glyceryl monocaprylate, 3-hydroxypropyl undecylenate and glyceryl monoundecylenate.

Another preferred embodiment of the present invention relates to a method as defined herein, wherein the total amount of the fatty acid ester or the mixture of two or more fatty acid esters or the mixture comprising one or more fatty acid esters provided in step (ii) is from 0.01 to 5 wt.-%, more preferably from 0.05 to 2 wt.-%, most preferably from 0.1 to 1 wt.-%, relative to the total weight of the skin care product obtained in step (iii).

Step (i) of the method as described herein may take place before step (ii) or step (i) of the method as described herein may take place after step (ii).

In the method as defined herein, the ingredients of a skin care product (apart from the substances provided in step (ii)) provided in step (i) may be provided separately or (partly) pre-mixed. The same applies to the fatty acid esters provided in step (ii), i.e. the fatty acid esters of the mixture of two or more fatty acid esters or the fatty acid ester(s) and other ingredient(s) of the mixture comprising one or more fatty acid esters may be provided separately (so that they only form the respective mixture after step (iii)) or (partly) pre-mixed.

The fatty acid ester or mixtures as described herein provided in step (ii) is/are provided in an amount that is sufficient to modify the physicochemical properties (as defined above) of the final skin care product (product of step (iii)).

A preferred embodiment of the present invention relates to a method as defined herein, wherein the skin care product is a product selected from the group consisting of leave-on skin care product, preferably oil in water emulsion or water in oil emulsion, and rinse-off skin care product, preferably shampoo, more preferably anti-dandruff shampoo, or shower gel. Another preferred embodiment relates to the method as defined herein, wherein the skin care product is a soap, preferably a bar soap or syndet soap.

Preferably, the skin care product whose physicochemical properties are modified in a method according to the invention is a rinse-off skin care product, preferably a shampoo, more preferably an anti-dandruff shampoo, or a shower gel. Also preferred is a soap, preferably a bar soap or syndet soap.

Another preferred embodiment of the present invention relates to a method as defined herein, wherein the modification of the physicochemical properties of the skin care product is an increase of the viscosity or foam volume or foam stability of the skin care product, preferably of a shampoo.

What has been stated above with regard to the increase of the viscosity or of the foam volume or of the foam stability of the skin care product in terms of the use as defined herein applies mutatis mutandis to the (preferred) embodiment(s) of the method as defined herein.

Another preferred embodiment relates to a method as defined herein, wherein the skin care product is a shampoo and the component(s) in step (ii) is/are provided in an amount that the resulting product is an anti-dandruff shampoo, i.e. displays antimycotic properties.

Another preferred embodiment of the invention relates to the method as defined herein, wherein the skin care product is sulfate-free and/or comprises sodium cocoyl isethionate, sodium cocoamphoacetate, sodium cocoyl glutamate, sodium methyl cocoyl taurate, sodium cocoyl isethionate, sodium cocoamphoacetate, sodium cocoyl glutamate, and sodium methyl cocoyl taurate, cocamide MIPA, disodium cocoyl glutamate, disodium lauryl sulfosuccinate, lauroyl/myristoyl methyl glucamide, sodium C14-C16 olefin sulfonate, sodium cocoamphoacetate, sodium cocoyl alaninate, sodium cocoyl glutamate, sodium cocoyl glycinate, sodium cocoyl isethionate, sodium laureth-5 carboxylate, sodium laureth-6 carboxylate, sodium lauroyl glutamate, sodium lauroyl lactylate, sodium lauroyl methyl isethionate, coco-glucoside, decyl glucoside, lauryl glucoside, cocamide MEA, cocoamidopropyl betaine, coco betaine, glycol distearate, laureth-4, isostearamide MIPA, lauryl hydroxysultaine, PEG-200 hydrogenated glyceryl palmate, PEG-7 glyceryl cocoate, PEG-4 rapeseedamide, PEG-40 hydrogenated castor oil, trideceth-9, and/or sodium lauroyl sarcosinate.

Another aspect of the present invention relates to a method for manufacturing a product selected from the group consisting of leave-on skin care product, preferably oil in water emulsion or water in oil emulsion, and rinse-off skin care product, preferably shampoo, more preferably anti-dandruff shampoo, shower gel, or soaps, preferably bar soaps or syndet soaps, comprising or consisting of the following steps:
(i) providing the ingredients of a leave-on or rinse-off skin care product or a leave-on or rinse-off skin care product (apart from the substance(s) provided in step (ii)),
(ii) providing a fatty acid ester or a mixture of two or more fatty acid esters or a mixture comprising one or more fatty acid esters, wherein the fatty acid ester or one, two or more, preferably all, of the fatty acid ester(s) is/are selected from the group consisting of 3-hydroxypropyl caprylate, 3-hydroxypropyl undecylenate and glyceryl monoundecylenate,
(iii) mixing the components of steps (i) and (ii).

A preferred embodiment of the present invention relates to a method as defined herein, wherein the fatty acid ester or one or two, preferably all, of the fatty acid ester(s) provided as fatty acid ester or mixture of two or more fatty acid esters or mixture comprising one or more fatty acid esters in step (ii) is/are selected from the group consisting of 3-hydroxypropyl caprylate and 3-hydroxypropyl undecylenate.

Another preferred embodiment of the present invention relates to a method as defined herein, wherein the fatty acid ester or one, two or three, preferably all, of the fatty acid ester(s) provided as fatty acid ester or mixture of two or more fatty acid esters or mixture comprising one or more fatty acid esters in step (ii) is/are selected from the group consisting of 3-hydroxypropyl caprylate, 3-hydroxypropyl undecylenate and glyceryl monoundecylenate.

Another preferred embodiment of the present invention relates to a method as defined herein, wherein the fatty acid ester or one or two, preferably all, of the fatty acid ester(s) provided as fatty acid ester or mixture of two or more fatty acid esters or mixture comprising one or more fatty acid esters in step (ii) is/are selected from the group consisting of 3-hydroxypropyl caprylate and 3-hydroxypropyl undecylenate.

Another preferred embodiment of the present invention relates to a method as defined herein, wherein the fatty acid ester provided in step (ii) is 3-hydroxypropyl caprylate or 3-hydroxypropyl undecylenate or glyceryl monoundecylenate.

Another preferred embodiment of the present invention relates to a method as defined herein, wherein the mixture comprising one or more fatty acid esters provided in step (ii) comprises 3-hydroxypropyl caprylate or 3-hydroxypropyl undecylenate or glyceryl monoundecylenate.

Another preferred embodiment of the present invention relates to a method as defined herein, wherein the mixture of two or more fatty acid esters provided in step (ii) is a mixture of 3-hydroxypropyl caprylate and 3-hydroxypropyl undecylenate, or of glyceryl monocaprylate and 3-hydroxypropyl undecylenate, or of 3-hydroxypropyl caprylate and glyceryl monoundecylenate, or of glyceryl monocaprylate and glyceryl monoundecylenate, or of 3-hydroxypropyl caprylate and glyceryl monocaprylate.

Another preferred embodiment of the present invention relates to a method as defined herein, wherein the mixture comprising one or more fatty acid esters provided in step (ii) comprises 3-hydroxypropyl caprylate and 3-hydroxypropyl undecylenate, or glyceryl monocaprylate and 3-hydroxypropyl undecylenate, or 3-hydroxypropyl caprylate and glyceryl monoundecylenate, or glyceryl monocaprylate and glyceryl monoundecylenate, or 3-hydroxypropyl caprylate and glyceryl monocaprylate.

Another preferred embodiment of the present invention relates to a method as defined herein, wherein the mixture of two or more fatty acid esters provided in step (ii) is a mixture of 3-hydroxypropyl caprylate, glyceryl monocaprylate and 3-hydroxypropyl undecylenate.

Another preferred embodiment of the present invention relates to a method as defined herein, wherein the mixture comprising one or more fatty acid esters provided in step (ii) comprises 3-hydroxypropyl caprylate, glyceryl monocaprylate and 3-hydroxypropyl undecylenate.

Another preferred embodiment of the present invention relates to a method as defined herein, wherein the mixture of two or more fatty acid esters provided in step (ii) is a mixture of 3-hydroxypropyl caprylate, glyceryl monocaprylate, 3-hydroxypropyl undecylenate and glyceryl monoundecylenate.

Another preferred embodiment of the present invention relates to a method as defined herein, wherein the mixture comprising one or more fatty acid esters provided in step (ii) comprises 3-hydroxypropyl caprylate, glyceryl monocaprylate, 3-hydroxypropyl undecylenate and glyceryl monoundecylenate.

Another preferred embodiment of the present invention relates to a method as defined herein, wherein the total amount of the fatty acid ester or the mixture of two or more fatty acid esters or the mixture comprising one or more fatty acid esters provided in step (ii) is from 0.01 to 5 wt.-%, more preferably from 0.05 to 2 wt.-%, most preferably from 0.1 to 1 wt.-%, relative to the total weight of the skin care product obtained in step (iii).

Preferably, the present invention relates to a method for manufacturing a rinse-off skin care product, preferably a shampoo, more preferably an anti-dandruff shampoo, or a shower gel.

Step (i) of the method as described herein may take place before step (ii) or step (i) of the method as described herein may take place after step (ii).

In the method as defined herein, the ingredients of a leave-on or rinse-off skin care product (apart from the substance(s) provided in step (ii)) provided in step (i) may be provided separately or (partly) pre-mixed. The same applies to the fatty acid esters provided in step (ii), i.e. the fatty acid esters of the mixture of two or more fatty acid esters or the fatty acid ester(s) and other ingredient(s) of the mixture comprising one or more fatty acid esters may be provided separately (so that they only form the respective mixture after step (iii)) or (partly) pre-mixed.

According to a preferred embodiment, the fatty acid ester or mixtures as described herein provided in step (ii) of the method as described herein is/are provided in an amount that is sufficient to modify the physicochemical properties (as defined above) of the final skin leave-on or rinse-off care product (product of step (iii)).

Another preferred embodiment relates to a method as defined herein, wherein the product is a shampoo and the component(s) in step (ii) is/are provided in an amount that the resulting product is an anti-dandruff shampoo, i.e. displays antimycotic properties.

Another preferred embodiment of the invention relates to the method as defined herein, wherein the skin care product is sulfate-free and/or comprises sodium cocoyl isethionate, sodium cocoamphoacetate, sodium cocoyl glutamate, sodium methyl cocoyl taurate, sodium cocoyl isethionate, sodium cocoamphoacetate, sodium cocoyl glutamate, and sodium methyl cocoyl taurate, cocamide MIPA, disodium cocoyl glutamate, disodium lauryl sulfosuccinate, lauroyl/myristoyl methyl glucamide, sodium C14-C16 olefin sulfonate, sodium cocoamphoacetate, sodium cocoyl alaninate, sodium cocoyl glutamate, sodium cocoyl glycinate, sodium cocoyl isethionate, sodium laureth-5 carboxylate, sodium laureth-6 carboxylate, sodium lauroyl glutamate, sodium lauroyl lactylate, sodium lauroyl methyl isethionate, coco-glucoside, decyl glucoside, lauryl glucoside, cocamide MEA, cocoamidopropyl betaine, coco betaine, glycol distearate, laureth-4, isostearamide MIPA, lauryl hydroxysultaine, PEG-200 hydrogenated glyceryl palmate, PEG-7 glyceryl cocoate, PEG-4 rapeseedamide, PEG-40 hydrogenated castor oil, trideceth-9, and/or sodium lauroyl sarcosinate.

Another aspect of the present invention relates to a shampoo, preferably an anti-dandruff shampoo, preferably manufactured according to a method as defined herein, comprising or consisting of
(i) one or more surfactant(s) selected from the group consisting of sodium lauryl ether sulfate, cocamidopropyl betaine, lauryl glucoside, caprylyl/capryl glucoside, sodium lauryl sulfate, disodium laureth sulfosuccinate, sodium lauryl sulfoacetate, decyl glucoside, sodium lauroyl sarcosinate, glycol distearate, coco-betaine, PPG-5-ceteth-20, coco-glucoside, diethylhexyl sodium sulfosuccinate, ammonium cocoyl isethionate, ammonium cocoyl sarcosinate, diethylhexyl sodium sulfosuccinate, cocamide-MEA, PEG-7 glyceryl cocoate, glycol/distearate, sodium oleoyl sarcosinate, sodium cocoyl isethionate, sodium cocoamphoacetate, sodium cocoyl glutamate, sodium methyl cocoyl taurate, sodium cocoyl isethionate, sodium cocoamphoacetate, sodium cocoyl glutamate, and sodium methyl cocoyl taurate, cocamide MIPA, disodium cocoyl glutamate, disodium lauryl sulfosuccinate, lauroyl/myristoyl methyl glucamide, sodium C14-C16 olefin sulfonate, sodium cocoamphoacetate, sodium cocoyl alaninate, sodium cocoyl glutamate, sodium cocoyl glycinate, sodium cocoyl isethionate, sodium laureth-5 carboxylate, sodium laureth-6 carboxylate, sodium lauroyl glutamate, sodium lauroyl lactylate, sodium lauroyl methyl isethionate, coco betaine, glycol distearate, laureth-4, isostearamide MIPA, lauryl hydroxysultaine, PEG-200 hydrogenated glyceryl palmate, PEG-4 rapeseedamide, PEG-40 hydrogenated castor oil, trideceth-9, and/or sodium lauroyl sarcosinate,
(ii) optionally water,
(iii) a fatty acid ester or a mixture of two or more fatty acid esters or a mixture comprising one or more fatty acid esters as defined herein,
optionally
(iv) one or more fragrance(s),
(v) one or more plant oil(s) selected from the group consisting of *Persea gratissima* (avocado) oil, *Olea europaea* (olive) oil, *Prunus amygdalus dulcis* (sweet almond) oil, *Helianthus annuus* (sunflower) seed oil, *Simmondsia chinensis* (jojoba) seed oil, *Mauritia flexuosa* fruit oil, *Calophyllum inophyllum* seed oil and *Triticum vulgare* (wheat) germ oil,
(vi) one or more preservative(s) selected from the group consisting of 2-phenoxyethanol, benzyl alcohol, dehydroacetic acid, methyl paraben, sorbic acid and benzoic acid, and
(vii) one or more active ingredient(s) selected from the group consisting of 4-hydroxyacetophenone, 1,2-pentanediol, 1,2-hexanediol, 1,2-octanediol, 1,2-decanediol, caprylhydroxamic acid, sorbitan caprylate and ethylhexylglycerine.

According to a preferred embodiment, the shampoo according to the invention comprises said components in the following amounts:
(ii) 0.5 to 80 wt.-%, preferably 0.5 to 20 wt.-%, of one or more surfactant(s),
(iii) 0.01 to 5 wt.-%, more preferably 0.05 to 2 wt.-%, most preferably 0.1 to 1 wt.-% of fatty acid ester or a mixture of two or more fatty acid esters or a mixture comprising one or more fatty acid esters as defined herein,
optionally
(iv) 0 to 2 wt.-%, preferably 0.05 to 1 wt.-%, of one or more fragrance(s),
(v) 0 to 20 wt.-%, preferably 0.1 to 10 wt.-%, of one or more plant oil(s),
(vi) 0.01 to 1 wt.-%, preferably 0.1 to 1 wt.-%, of one or more preservative(s),
(vii) 0.01 to 5 wt.-%, preferably 0.1 to 3 wt.-%, of one or more active ingredient(s),
whereby said amounts add up—together with water and optionally with any additional ingredients present—to 100 wt.-%.

A preferred embodiment of the present invention relates to a shampoo as defined herein, wherein the fatty acid ester or one or two, preferably all, of the fatty acid ester(s) of component (iii) is/are selected from the group consisting of 3-hydroxypropyl caprylate and 3-hydroxypropyl undecylenate.

Another preferred embodiment of the present invention relates to a shampoo as defined herein, wherein the fatty acid ester or one, two or three, preferably all, of the fatty acid ester(s) of component (iii) is/are selected from the group consisting of 3-hydroxypropyl caprylate, 3-hydroxypropyl undecylenate and glyceryl monoundecylenate.

Another preferred embodiment of the present invention relates to a shampoo as defined herein, wherein the fatty acid ester or one or two, preferably all, of the fatty acid ester(s) of component (iii) is/are selected from the group consisting of 3-hydroxypropyl caprylate and 3-hydroxypropyl undecylenate.

Another preferred embodiment of the present invention relates to a shampoo as defined herein, wherein the fatty acid ester of component (iii) is 3-hydroxypropyl or 3-hydroxypropyl undecylenate or glyceryl monoundecylenate.

Another preferred embodiment of the present invention relates to a shampoo as defined herein, wherein the mixture comprising one or more fatty acid esters of component (iii) comprises 3-hydroxypropyl caprylate or 3-hydroxypropyl undecylenate or glyceryl monoundecylenate.

Another preferred embodiment of the present invention relates to a shampoo as defined herein, wherein the mixture of two or more fatty acid esters of component (iii) is a mixture of 3-hydroxypropyl caprylate and 3-hydroxypropyl undecylenate, or of glyceryl monocaprylate and 3-hydroxypropyl undecylenate, or of 3-hydroxypropyl caprylate and glyceryl monoundecylenate, or of glyceryl monocaprylate and glyceryl monoundecylenate, or of 3-hydroxypropyl caprylate and glyceryl monocaprylate.

Another preferred embodiment of the present invention relates to a shampoo as defined herein, wherein the mixture comprising one or more fatty acid esters of component (iii) comprises 3-hydroxypropyl caprylate and 3-hydroxypropyl undecylenate, or glyceryl monocaprylate and 3-hydroxypropyl undecylenate, or 3-hydroxypropyl caprylate and glyceryl monoundecylenate, or glyceryl monocaprylate and glyceryl monoundecylenate, or 3-hydroxypropyl caprylate and glyceryl monocaprylate.

Another preferred embodiment of the present invention relates to a shampoo as defined herein, wherein the mixture of two or more fatty acid esters of component (iii) is a mixture of 3-hydroxypropyl caprylate, glyceryl monocaprylate and 3-hydroxypropyl undecylenate.

Another preferred embodiment of the present invention relates to a shampoo as defined herein, wherein the mixture comprising one or more fatty acid esters of component (iii) comprises 3-hydroxypropyl caprylate, glyceryl monocaprylate and 3-hydroxypropyl undecylenate.

Another preferred embodiment of the present invention relates to a shampoo as defined herein, wherein the mixture of two or more fatty acid esters of component (iii) is a mixture of 3-hydroxypropyl caprylate, glyceryl monocaprylate, 3-hydroxypropyl undecylenate and glyceryl monoundecylenate.

Another preferred embodiment of the present invention relates to a shampoo as defined herein, wherein the mixture comprising one or more fatty acid esters of component (iii) comprises 3-hydroxypropyl caprylate, glyceryl monocaprylate, 3-hydroxypropyl undecylenate and glyceryl monoundecylenate.

Another preferred embodiment of the present invention relates to a shampoo as defined herein, wherein the shampoo is sulfate-free and/or comprises sodium cocoyl isethionate, sodium cocoamphoacetate, sodium cocoyl glutamate, sodium methyl cocoyl taurate, sodium cocoyl isethionate, sodium cocoamphoacetate, sodium cocoyl glutamate, and sodium methyl cocoyl taurate, cocamide MIPA, disodium cocoyl glutamate, disodium lauryl sulfosuccinate, lauroyl/myristoyl methyl glucamide, sodium C14-C16 olefin sulfonate, sodium cocoamphoacetate, sodium cocoyl alaninate, sodium cocoyl glutamate, sodium cocoyl glycinate, sodium cocoyl isethionate, sodium laureth-5 carboxylate, sodium laureth-6 carboxylate, sodium lauroyl glutamate, sodium lauroyl lactylate, sodium lauroyl methyl isethionate, coco-glucoside, decyl glucoside, lauryl glucoside, cocamide MEA, cocoamidopropyl betaine, coco betaine, glycol distearate, laureth-4, isostearamide MIPA, lauryl hydroxysultaine, PEG-200 hydrogenated glyceryl palmate, PEG-7 glyceryl cocoate, PEG-4 rapeseedamide, PEG-40 hydrogenated castor oil, trideceth-9, and/or sodium lauroyl sarcosinate.

Another aspect of the present invention relates to a hair or body cream, preferably manufactured according to a method as defined herein, comprising or consisting of
(i) water,
(ii) one or more emulsifying agent(s) selected from the group consisting of PEG-100 stearate, cetearyl glycoside, distearyldimonium chloride, palmitamidopropyltrimonium chloride, glyceryl caprylate, glyceryl stearate citrate, glyceryl oleate citrate, polyglyceryl-3 methylglucose distearate, cetearyl alcohol, potassium cetyl phosphate, sodium cetyl phosphate, acrylates/C10-alkyl acrylate cross-polymer (polymeric emulsifier), ammonium acryloyldimethyltaurate/Beheneth-25 methacrylate crosspolymer (polymeric emulsifier), polyglyceryl-4 caprate, polyglyceryl-4 caprylate/caprate, cetyl PEG/PPG-10/1, dimethicone, polyglycer-yl-6 dioleate, polyglyceryl-2 stearate, PEG-30 dipoly-hydroxystearate, sodium stearoyl lactylate, xanthan gum, dehydro xanthan gum, hydrogenated palm glycerides, polyglyerol-3 oleate, polyglyceryl-3 polyricinoleate, sodium caproyl/lauroyl lactylate, glyceryl stearate se, polyglyceryl-3 dicitrate/stearate and PEG-40 hydrogenated castor oil,
(iii) one or more oil body/bodies selected from the group consisting of caprylic capric triglycerides, mineral oil, *Simmondsia chinensis* (jojoba) seed oil, *Butyrospermum parkii* (shea) butter, dicaprylyl ether, cyclomethicone, dimethicone, C12-15 alkyl benzoate, isopropyl palmitate, isopropyl myristate, octyldodecanol, cetearyl ethylhexanoate, cetearyl nonanoate, ethylhexyl isononanoate, propylene glycol dicaprylate/dicaprate, propylheptyl caprylate, decyl oleate, hexyl laurate, ethylhexyl stearate, triisononanoin, iso-adipate, stearyl heptanoate and stearyl caprylate,
(iv) a fatty acid ester or a mixture of two or more fatty acid esters or a mixture comprising one or more fatty acid esters as defined herein,
(v) one or more fragrance(s),
optionally
(vi) one or more preservative(s) selected from the group consisting of 2-phenoxyethanol, benzyl alcohol, dehydroacetic acid, methyl paraben, sorbic acid and benzoic acid (and/or their salts), and
(vii) one or more active ingredient(s) selected from the group consisting of 4-hydroxyacetophenone, 1,2-pentanediol, 1,2-hexanediol, 1,2-octanediol, 1,2-decanediol, caprylhydroxamic acid, sorbitan caprylate and ethylhexylglycerine.

According to a preferred embodiment, the hair or body cream according to the invention comprises said components in the following amounts:
(ii) 0.1 to 5 wt.-% of one or more emulsifying agent(s),
(iii) 0.5 to about 40 wt.-% of one or more oil body/bodies,
(iv) 0.01 to 5 wt.-%, preferably 0.05 to 2 wt.-%, more preferably 0.1 to 1 wt.-% of a fatty acid ester or a mixture of two or more fatty acid esters or a mixture comprising one or more fatty acid esters as defined herein,
(v) 0 to 2 wt.-% of one or more fragrance(s),
optionally
(vi) 0.05 to 1 wt.-% of one or more preservative(s),
(vii) 0.05 to 5 wt.-% of one or more active ingredient(s),
whereby said amounts add up—together with water and optionally with any additional ingredients present—to 100 wt.-%.

A preferred embodiment of the present invention relates to a hair or body cream as defined herein, wherein the fatty acid ester or one or two, preferably all, of the fatty acid ester(s) of component (iv) is/are selected from the group consisting of 3-hydroxypropyl caprylate and 3-hydroxypropyl undecylenate.

Another preferred embodiment of the present invention relates to a hair or body cream as defined herein, wherein the fatty acid ester or one, two or three, preferably all, of the fatty acid ester(s) of component (iv) is/are selected from the group consisting of 3-hydroxypropyl caprylate, 3-hydroxypropyl undecylenate and glyceryl monoundecylenate.

Another preferred embodiment of the present invention relates to a hair or body cream as defined herein, wherein the fatty acid ester or one or two, preferably all, of the fatty acid ester(s) of component (iv) is/are selected from the group consisting of 3-hydroxypropyl caprylate and 3-hydroxypropyl undecylenate.

Another preferred embodiment of the present invention relates to a hair or body cream as defined herein, wherein the fatty acid ester of component (iv) is 3-hydroxypropyl caprylate or 3-hydroxypropyl undecylenate or glyceryl monoundecylenate.

Another preferred embodiment of the present invention relates to a hair or body cream as defined herein, wherein the mixture comprising one or more fatty acid esters of component (iv) comprises 3-hydroxypropyl caprylate or 3-hydroxypropyl undecylenate or glyceryl monoundecylenate.

Another preferred embodiment of the present invention relates to a hair or body cream as defined herein, wherein the mixture of two or more fatty acid esters of component (iv) is a mixture of 3-hydroxypropyl caprylate and 3-hydroxypropyl undecylenate, or of glyceryl monocaprylate and 3-hydroxypropyl undecylenate, or of 3-hydroxypropyl caprylate and glyceryl monoundecylenate, or of glyceryl monocaprylate and glyceryl monoundecylenate, or of 3-hydroxypropyl caprylate and glyceryl monocaprylate.

Another preferred embodiment of the present invention relates to a hair or body cream as defined herein, wherein the mixture comprising one or more fatty acid esters of component (iv) comprises 3-hydroxypropyl caprylate and 3-hydroxypropyl undecylenate, or glyceryl monocaprylate and 3-hydroxypropyl undecylenate, or 3-hydroxypropyl caprylate and glyceryl monoundecylenate, or glyceryl monocaprylate and glyceryl monoundecylenate, or 3-hydroxypropyl caprylate and glyceryl monocaprylate.

Another preferred embodiment of the present invention relates to a hair or body cream as defined herein, wherein the mixture of two or more fatty acid esters of component (iv) is a mixture of 3-hydroxypropyl caprylate, glyceryl monocaprylate and 3-hydroxypropyl undecylenate.

Another preferred embodiment of the present invention relates to a hair or body cream as defined herein, wherein the mixture comprising one or more fatty acid esters of component (iv) comprises 3-hydroxypropyl caprylate, glyceryl monocaprylate and 3-hydroxypropyl undecylenate.

Another preferred embodiment of the present invention relates to a hair or body cream as defined herein, wherein the mixture of two or more fatty acid esters of component (iv) is a mixture of 3-hydroxypropyl caprylate, glyceryl monocaprylate, 3-hydroxypropyl undecylenate and glyceryl monoundecylenate.

Another preferred embodiment of the present invention relates to a hair or body cream as defined herein, wherein the mixture comprising one or more fatty acid esters of component (iv) comprises 3-hydroxypropyl caprylate, glyceryl monocaprylate, 3-hydroxypropyl undecylenate and glyceryl monoundecylenate.

In certain embodiments, a hair or body cream as disclosed herein may be sulfate-free and/or may comprise sodium cocoyl isethionate, sodium cocoamphoacetate, sodium cocoyl glutamate, and sodium methyl cocoyl taurate, cocamide MIPA, disodium cocoyl glutamate, disodium lauryl sulfosuccinate, lauroyl/myristoyl methyl glucamide, sodium C14-C16 olefin sulfonate, sodium cocoamphoacetate, sodium cocoyl alaninate, sodium cocoyl glutamate, sodium cocoyl glycinate, sodium cocoyl isethionate, sodium laureth-5 carboxylate, sodium laureth-6 carboxylate, sodium lauroyl glutamate, sodium lauroyl lactylate, sodium lauroyl methyl isethionate, coco-glucoside, decyl glucoside, lauryl glucoside, cocamide MEA, cocoamidopropyl betaine, coco betaine, glycol distearate, laureth-4, isostearamide MIPA, lauryl hydroxysultaine, PEG-200 hydrogenated glyceryl palmate, PEG-7 glyceryl cocoate, PEG-4 rapeseedamide, PEG-40 hydrogenated castor oil, trideceth-9 and/or sodium lauroyl sarcosinate.

Preferred bar soaps as disclosed herein are fatty acid soaps. Fatty acid soaps are alkali metal soaps of fatty acids having alkyl chain lengths of about $C_8$-$C_{22}$, preferably about $C_{12}$-$C_{18}$, and especially those of about $C_{12}$-$C_{14}$ chain lengths. They are important in producing lather rapidly and of good, highly acceptable quality. Preferred soaps include those made from fatty acids derived from natural sources such as plant or animal-derived glycerides, e.g., coconut oil, tallow, palm kernel oil, babassu oil, soybean oil, castor oil, whale oil, fish oil, grease, lard, palm stearin oil and mixtures thereof. The ph value of these bar soaps is alkaline due to the saponification process.

Typical bar soap ingredients include sodium cocoate, sodium stearate, sodium oleate, sodium palmitate, sodium linoleate, sodium laurate, sodium linoleate, sodium myristate, sodium isethionate, sodium C14-16 olefin sulfonate, sodium lauroyl isethionate, stearic acid, sodium palmitate, lauric acid, aqua, sodium isethionate, sodium stearate, cocamidopropyl betaine, sodium palm kernelate, glycerin, parfum, sodium chloride, zinc oxide, tetrasodium EDTA, tetrasodium etidronate, alumina, alpha-isomethyl ionone, benzyl alcohol, butylphenyl methylpropionalsodium isethionate, cocamidopropyl betaine, sodium palm kernelate, potassium palm kernelate, sodium palmate, potassium palmate, sodium castorate, sodium carbonate, sodium isostearoyl lactylate, sodium dodecylbenzenesulfonate sodium palm kernelate, lanolin, lecithin, silica, talc, glycerin, sodium C14-16 olefin sulfonate, sodium lauroyl isethionate, sodium sulfate, sodium laureth sulfate, sodium oleate, glycerin, sodium tallowate, stearic acid, palm acid, palm kernel acid, coconut acid, lauric acid, PEG-4, PEG-20 and further additives like dyes, pigments, sequestrants, moisturizers, emollients, plant oils, plant extracts, fatty acid esters, fatty alcohols, antimicrobials, vitamins, antioxidants, solubilizers, fragrances, starch, clay minerals, abrasives, acids & alkalis, aqua.

Syndet (bar) soaps (Syn=synthetic, det=detergents) are an alternative to traditional bar soaps. The basis surfactants are mostly synthetic. They are very mild to the skin and have a neutral or slightly acidic pH value.

Typical syndet soap ingredients are: sodium lauryl sulfate, alpha olefin sulfonate, glycerol monostearate, cetostearyl alcohol, paraffin wax, cocoamidopropyl betaine, decyl glucoside, coco-glucoside, sodium cocoamphoacetate, sodium cocoyl isethionate, disodium lauryl sulfosuccinate, sodium laureth-5 carboxylate, cetearyl alcohol, glyceryl stearate, paraffin, cocamidopropyl betaine, disodium lauryl sulfosuccinate, glyceryl stearate, disodium lauryl sulfosuccinate, palmitic acid, stearic acid, lanolin, lecithin, sodium lauroyl sarcosinate, cetyl palmitate and further additives like dyes, pigments, sequestrants, moisturizers, emollients, plant oils, plant extracts, fatty acid esters, fatty alcohols, antimicrobials, vitamins, antioxidants, solubilizers, fragrances, starch, clay minerals, acids & alkalis, aqua.

A syndet soap as disclosed herein may also be a so-called combo soap. Combo soaps combine ingredients from syndet soap and traditional saponified soaps.

Another aspect of the present invention relates to a soap, preferably bar soap or syndet soap, preferably manufactured according to a method as defined herein, comprising or consisting of
  (i) one or more surfactant(s) selected from the group consisting of sodium lauryl ether sulfate, cocamidopropyl betaine, lauryl glucoside, caprylyl/capryl glucoside, sodium lauryl sulfate, disodium laureth sulfosuccinate, sodium lauryl sulfoacetate, decyl glucoside, glycol distearate, coco-betaine, PPG-5-ceteth-20, coco-glucoside, diethylhexyl sodium sulfosuccinate, ammonium cocoyl isethionate, ammonium cocoyl sarcosinate, diethylhexyl sodium sulfosuccinate, cocamide-MEA, PEG-7 glyceryl cocoate, glycol/distearate, sodium oleoyl sarcosinate, sodium cocoyl isethionate, sodium cocoamphoacetate, sodium cocoyl glutamate, sodium methyl cocoyl taurate, sodium cocoyl isethionate, sodium cocoamphoacetate, sodium cocoyl glutamate, and sodium methyl cocoyl taurate, cocamide MIPA, disodium cocoyl glutamate, disodium lauryl sulfosuccinate, lauroyl/myristoyl methyl glucamide, sodium C14-C16 olefin sulfonate, sodium cocoamphoacetate, sodium cocoyl alaninate, sodium cocoyl glutamate, sodium cocoyl glycinate, sodium cocoyl isethionate, sodium laureth-5 carboxylate, sodium laureth-6 carboxylate, sodium lauroyl glutamate, sodium lauroyl lactylate, sodium lauroyl methyl isethionate, laureth-4, isostearamide MIPA, lauryl hydroxysultaine, PEG-200 hydrogenated glyceryl palmate, PEG-4 rapeseedamide, PEG-40 hydrogenated castor oil, trideceth-9, sodium cocoate, sodium stearate, sodium oleate, sodium palmitate, sodium linoleate, sodium laurate, sodium linoleate, sodium myristate, sodium isethionate, potassium palm kernelate, sodium palmate, potassium palmate, sodium castorate, sodium carbonate, sodium isostearoyl lactylate, sodium dodecylbenzenesulfonate, sodium palm kernelate, lanolin, lecithin, silica, talc, glycerin, sodium lauroyl isethionate, sodium sulfate, sodium laureth sulfate, glycerin, sodium tallowate, stearic acid, palm acid, palm kernel acid, coconut acid, lauric acid, PEG-4, PEG-20, alpha olefin sulfonate, glycerol monostearate, cetostearyl alcohol, paraffin wax, sodium cocoamphoacetate, sodium cocoyl isethionate, disodium lauryl sulfosuccinate, sodium laureth-5 carboxylate, cetearyl alcohol, glyceryl stearate, paraffin, disodium lauryl sulfosuccinate, glyceryl stearate, palmitic acid, stearic acid, lanolin, lecithin, cetyl palmitate and sodium lauroyl sarcosinate,
  (ii) optionally water,
  (iii) a fatty acid ester or a mixture of two or more fatty acid esters or a mixture comprising one or more fatty acid esters as defined herein,
  optionally
  (iv) one or more fragrance(s), (v) one or more plant oil(s) selected from the group consisting of *Persea gratissima* (avocado) oil, *Olea europaea* (olive) oil, *Prunus amygdalus dulcis* (sweet almond) oil, *Helianthus annuus* (sunflower) seed oil, *Simmondsia chinensis* (jojoba) seed oil, *Mauritia flexuosa* fruit oil, *Calophyllum inophyllum* seed oil and *Triticum vulgare* (wheat) germ oil, (vi) one or more preservative(s) selected from the group consisting of 2-phenoxyethanol, benzyl alcohol, dehydroacetic acid, methyl paraben, sorbic acid, benzoic acid, and other classes of compounds listed in Appendix 6, Parts A and B of the Kosmetikverordnung ("Cosmetics Directive").

and (vii) one or more active ingredient(s) selected from the group consisting of 4-hydroxyacetophenone, 1,2-pentanediol, 1,2-hexanediol, 1,2-octanediol, 1,2-decanediol, caprylhydroxamic acid, sorbitan caprylate and ethylhexylglycerine.

The phrase "optionally water" refers to a soap as disclosed herein, which in some embodiments contains water and in other embodiments is free, or substantially free, of water.

According to a preferred embodiment, the soap according to the invention comprises said components in the following amounts:

(ii) 0.5 to 80 wt.-%, preferably 0.5 to 20 wt.-%, of one or more surfactant(s), (iii) 0.01 to 5 wt.-%, more preferably 0.05 to 2 wt.-%, most preferably 0.1 to 1 wt.-% of fatty acid ester or a mixture of two or more fatty acid esters or a mixture comprising one or more fatty acid esters as defined herein, optionally (iv) 0 to 2 wt.-%, preferably 0.05 to 1 wt.-%, of one or more fragrance(s), (v) 0.01 to 20 wt.-%, preferably 0.1 to 10 wt.-%, of one or more plant oil(s), (vi) 0 to 1 wt.-%, preferably 0.1 to 1 wt.-%, of one or more preservative(s), (vii) 0.01 to 5 wt.-%, preferably 0.1 to 3 wt.-%, of one or more active ingredient(s), whereby said amounts add up—together with water and optionally with any additional ingredients present—to 100 wt.-%.

A preferred embodiment of the present invention relates to a soap, preferably bar soap or syndet soap, as defined herein, wherein the fatty acid ester or one or two, preferably all, of the fatty acid ester(s) of component (iii) is/are selected from the group consisting of 3-hydroxypropyl caprylate and 3-hydroxypropyl undecylenate.

Another preferred embodiment of the present invention relates to a soap, preferably bar soap or syndet soap, as defined herein, wherein the fatty acid ester or one, two or three, preferably all, of the fatty acid ester(s) of component (iii) is/are selected from the group consisting of 3-hydroxypropyl caprylate, 3-hydroxypropyl undecylenate and glyceryl monoundecylenate.

Another preferred embodiment of the present invention relates to a soap, preferably bar soap or syndet soap, as defined herein, wherein the fatty acid ester or one or two, preferably all, of the fatty acid ester(s) of component (iii) is/are selected from the group consisting of 3-hydroxypropyl caprylate and 3-hydroxypropyl undecylenate.

Another preferred embodiment of the present invention relates to a soap, preferably bar soap or syndet soap, as defined herein, wherein the fatty acid ester of component (iii) is 3-hydroxypropyl caprylate or 3-hydroxypropyl undecylenate or glyceryl monoundecylenate.

Another preferred embodiment of the present invention relates to a soap, preferably bar soap or syndet soap, as defined herein, wherein the mixture comprising one or more fatty acid esters of component (iii) comprises 3-hydroxypropyl caprylate or 3-hydroxypropyl undecylenate or glyceryl monoundecylenate.

Another preferred embodiment of the present invention relates to a soap, preferably bar soap or syndet soap, as defined herein, wherein the mixture of two or more fatty acid esters of component (iii) is a mixture of 3-hydroxypropyl caprylate and 3-hydroxypropyl undecylenate, or of glyceryl monocaprylate and 3-hydroxypropyl undecylenate, or of 3-hydroxypropyl caprylate and glyceryl monoundecylenate, or of glyceryl monocaprylate and glyceryl monoundecylenate, or of 3-hydroxypropyl caprylate and glyceryl monocaprylate.

Another preferred embodiment of the present invention relates to a soap, preferably bar soap or syndet soap, as defined herein, wherein the mixture comprising one or more fatty acid esters of component (iii) comprises 3-hydroxypropyl caprylate and 3-hydroxypropyl undecylenate, or glyceryl monocaprylate and 3-hydroxypropyl undecylenate, or 3-hydroxypropyl caprylate and glyceryl monoundecylenate, or glyceryl monocaprylate and glyceryl monoundecylenate, or 3-hydroxypropyl caprylate and glyceryl monocaprylate.

Another preferred embodiment of the present invention relates to a soap, preferably bar soap or syndet soap, as defined herein, wherein the mixture of two or more fatty acid esters of component (iii) is a mixture of 3-hydroxypropyl caprylate, glyceryl monocaprylate and 3-hydroxypropyl undecylenate.

Another preferred embodiment of the present invention relates to a soap, preferably bar soap or syndet soap, as defined herein, wherein the mixture comprising one or more fatty acid esters of component (iii) comprises 3-hydroxypropyl caprylate, glyceryl monocaprylate and 3-hydroxypropyl undecylenate.

Another preferred embodiment of the present invention relates to a soap, preferably bar soap or syndet soap, as defined herein, wherein the mixture of two or more fatty acid esters of component (iii) is a mixture of 3-hydroxypropyl caprylate, glyceryl monocaprylate, 3-hydroxypropyl undecylenate and glyceryl monoundecylenate.

Another preferred embodiment of the present invention relates to a soap, preferably bar soap or syndet soap, as defined herein, wherein the mixture comprising one or more fatty acid esters of component (iii) comprises 3-hydroxypropyl caprylate, glyceryl monocaprylate, 3-hydroxypropyl undecylenate and glyceryl monoundecylenate.

Another preferred embodiment of the present invention relates to a soap, preferably bar soap or syndet soap, as defined herein, wherein the soap is sulfate-free and/or comprises sodium cocoyl isethionate, sodium cocoamphoacetate, sodium cocoyl glutamate, sodium methyl cocoyl taurate, sodium cocoyl isethionate, sodium cocoamphoacetate, sodium cocoyl glutamate, and sodium methyl cocoyl taurate, cocamide MIPA, disodium cocoyl glutamate, disodium lauryl sulfosuccinate, lauroyl/myristoyl methyl glucamide, sodium C14-C16 olefin sulfonate, sodium cocoamphoacetate, sodium cocoyl alaninate, sodium cocoyl glutamate, sodium cocoyl glycinate, sodium cocoyl isethionate, sodium laureth-5 carboxylate, sodium laureth-6 carboxylate, sodium lauroyl glutamate, sodium lauroyl lactylate, sodium lauroyl methyl isethionate, coco-glucoside, decyl glucoside, lauryl glucoside, cocamide MEA, cocoamidopropyl betaine, coco betaine, glycol distearate, laureth-4, isostearamide MIPA, lauryl hydroxysultaine, PEG-200 hydrogenated glyceryl palmate, PEG-7 glyceryl cocoate, PEG-4 rapeseedamide, PEG-40 hydrogenated castor oil, trideceth-9, and/or sodium lauroyl sarcosinate.

(Preferred) embodiments of the use according to the invention correspond to or can be derived from the (preferred) embodiments of the methods or products according to the invention, which are explained above, or vice versa.

The present disclosure also relates to a skin care product as disclosed herein, wherein the fatty acid ester is glyceryl monocaprylate in place of 3-hydroxypropyl caprylate, 3-hydroxypropyl undecylenate and/or glyceryl monoundecylenate. Glyceryl monocaprylate refers to a monoester of (mono)glycerol (CAS Registry Number: 56-81-5; also known as 1,2,3-propanetriol) with caprylic acid and glyceryl monoundecylenate refers to a monoester of (mono)glycerol with undecylenic acid.

The invention will now be described in more detail hereinafter with references to the examples.

EXAMPLES

1.) Viscosity in Hair and Body Wash Formulation
1.1) Formulations with 3-hydroxypropyl Caprylate or 3-hydroxypropyl Undecylenate

TABLE 1.1

Hair & body wash formulation with 3-hydroxypropy caprylate and 3-hydroxypropyl undecylenate (w/w %)

|  | INCI | Placebo 1 | 2 | 3 | 4 | 5 | 6 | 7 |
|---|---|---|---|---|---|---|---|---|
| A. | Sodium Laureth Sulfate, Lauryl Glycoside (Plantacare PS 10) | 17.0 | 17.0 | 17.0 | 17.0 | 17.0 | 17.0 | 17.0 |
|  | Citric Acid | 0.15 | 0.15 | 0.15 | 0.15 | 0.15 | 0.15 | 0.15 |
|  | 1,2-Hexanediol, Caprylyl Glycol (Symdiol 68) | 1.0 | 1.0 | 1.0 | 1.0 | 1.0 | 1.0 | 1.0 |
|  | Disodium EDTA | 0.1 | 0.1 | 0.1 | 0.1 | 0.1 | 0.1 | 0.1 |
|  | Sodium Chloride | 0.4 | 0.4 | 0.4 | 0.4 | 0.4 | 0.4 | 0.4 |
| B. | Water (Aqua) | 76.0 | 75.7 | 75.5 | 75.0 | 75.7 | 75.5 | 75.0 |
|  | Polyquaternium-10 | 0.2 | 0.2 | 0.2 | 0.2 | 0.2 | 0.2 | 0.2 |
| C. | Potassium Sorbate | 0.15 | 0.15 | 0.15 | 0.15 | 0.15 | 0.15 | 0.15 |
| D. | Cocoannidopropyl Betaine (Tego Betain F50) | 5.0 | 5.0 | 5.0 | 5.0 | 5.0 | 5.0 | 5.0 |
| E. | 3-Hydroxypropyl Caprylate | — | 0.3 | 0.5 | 1.0 | — | — | — |
|  | 3-Hydroxypropyl Undecylenate | — | — | — | — | 0.3 | 0.5 | 1.0 |
|  | SUM |  |  |  | 100.0 |  |  |  |

Production Method:
Blend phase A by stirring slowly with a vane stirrer, stop the process when foaming starts.

Swell 0.2 wt-% Ucare Polymer JR-400 (INCI: Polyquaternium-10, cf. Table 1.1) in water by stirring and warming up to 50° C. (the dispersion becomes clear and slightly viscous when swelling process is completed). Add phases B, C, D and E to A one after the other by stirring with a vane stirrer (pH value 5.7).

3-Hydroxypropyl caprylate or 3-hydroxypropyl undecylenate were incorporated into the shampoo formulations according to Table 1.1 with a concentration of 0.3, 0.5 or 1.0 wt.-%, respectively (trial 2-7). The viscosity η [mPas] of these samples was determined by using a rheometer.

Equipment and Method:
Rheometer HAAKE rheostress1; cone and plate measurement system, CP 60/1°
Method: Flow Curve CR (controlled rate)
T: 23° C.
Shear rate ẏ (1/s): 5

TABLE 1.2

Results of viscosity measurements in η [mPas] in shampoo (trials 1-7)

|  | Placebo, without active | with 3-hydroxypropyl caprylate | | | with 3-hydroxypropyl undecylenate | | |
|---|---|---|---|---|---|---|---|
| Trial no. | 1 | 2 | 3 | 4 | 5 | 6 | 7 |
| Dosage (%) | 0 | 0.3 | 0.5 | 1.0 | 0.3 | 0.5 | 1.0 |

TABLE 1.2-continued

Results of viscosity measurements
in η [mPas] in shampoo (trials 1-7)

|  | Placebo, without active | with 3-hydroxypropyl caprylate | | | with 3-hydroxypropyl undecylenate | | |
|---|---|---|---|---|---|---|---|
| Trial no. | 1 | 2 | 3 | 4 | 5 | 6 | 7 |
| Viscosity (mPas) | 1397.3 | 3095.1 | 4144.7 | 4741.1 | 3834.6 | 6178.5 | 7818.1 |

FIG. 1 shows the viscosity in η [mPas] (y-axis) of the shampoos comprising 0, 0.3, 0.5 or 1.0 wt.-% of 3-hydroxypropyl caprylate (trials 1-4).

Figure 2:
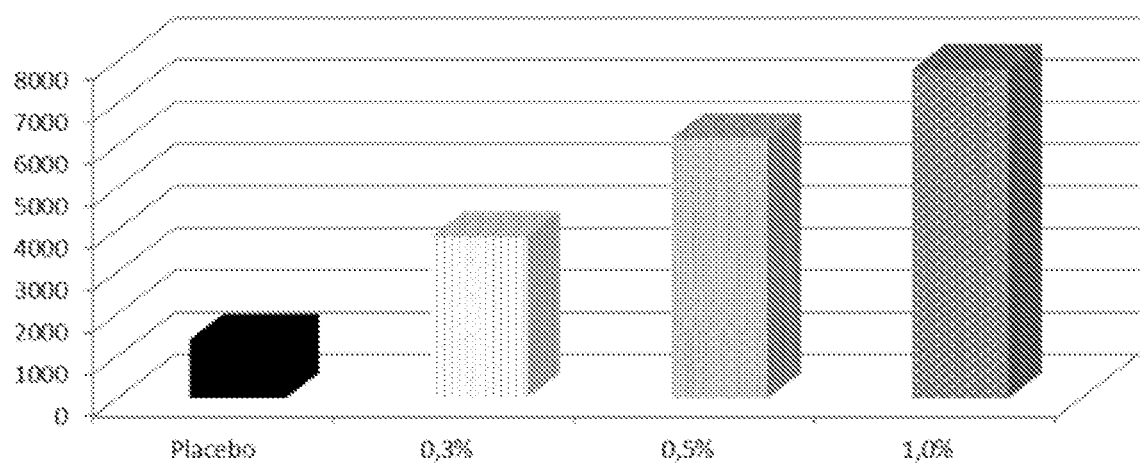
FIG. 2 shows the viscosity in η [mPas] (y-axis) of shampoos comprising 0, 0.3, 0.5 or 1.0 wt.-% of 3-hydroxypropyl undecylenate versus placebo.

FIG. 2 shows the viscosity in η [mPas] (y-axis) of the shampoos comprising 0, 0.3, 0.5 or 1.0 wt.-% of 3-hydroxypropyl undecylenate (trials 1 and 5-7).

It could be clearly demonstrated that the addition of 3-hydroxypropyl caprylate or 3-hydroxypropyl undecylenate leads to an increase of viscosity in shampoo. By increasing the concentration of 3-hydroxypropyl caprylate or 3-hydroxypropyl undecylenate, a dose dependent increase of viscosity could be observed versus shampoo without any active ingredient (placebo, trial 1).

1.2) Formulations with Glyceryl Monocaprylate

In a second experiment, the influence of glyceryl monocaprylate on viscosity was tested according to the procedure described in the preceding section 1.1.

TABLE 1.3

Hair & body wash formulation

| INCI | Placebo A | B | C | D |
|---|---|---|---|---|
| A. Sodium Laureth Sulfate, Lauryl Glycoside (Plantacare PS 10) | 17.0 | 17.0 | 17.0 | 17.0 |
| Citric Acid | 0.15 | 0.15 | 0.15 | 0.15 |
| 1,2-Hexanediol, Caprylyl Glycol (Symdiol 68) | 1.0 | 1.0 | 1.0 | 1.0 |
| Disodium EDTA | 0.1 | 0.1 | 0.1 | 0.1 |
| Sodium Chloride | 0.4 | 0.4 | 0.4 | 0.4 |
| B. Water (Aqua) | 76.0 | 75.7 | 75.5 | 75.0 |
| Polyquaternium-10 | 0.2 | 0.2 | 0.2 | 0.2 |
| C. Potassium Sorbate | 0.15 | 0.15 | 0.15 | 0.15 |
| D. Cocoamidopropyl Betaine (Tego Betain F50) | 5.0 | 5.0 | 5.0 | 5.0 |
| E. Glyceryl Monocaprylate | — | 0.3 | 0.5 | 1.0 |
| SUM | | 100.0 | | |

Production Method:

Blend phase A by stirring slowly with a vane stirrer, stop the process when foaming starts.

Swell 0.3 wt.-% Ucare Polymer JR-400 (INCI: Polyquaternium-10, cf. Table 1.3) in water by stirring and warming up to 50° C. (the dispersion becomes clear and slightly viscous, when swelling process is completed). Add phases B, C, D and E to A one after the other by stirring with a vane stirrer (pH value 5.8).

TABLE 1.4

Results of viscosity measurements in η [mPas] in shampoo (trials A-D)

|  | Placebo without active | with Glyceryl Monocaprylate | | |
|---|---|---|---|---|
| Trial no. | A | B | C | D |
| Dosage (%) | 0 | 0.3 | 0.5 | 1.0 |
| Viscosity (mPas) | 2837.3 | 3541.6 | 3605.0 | 3760.6 |

Figure 3:
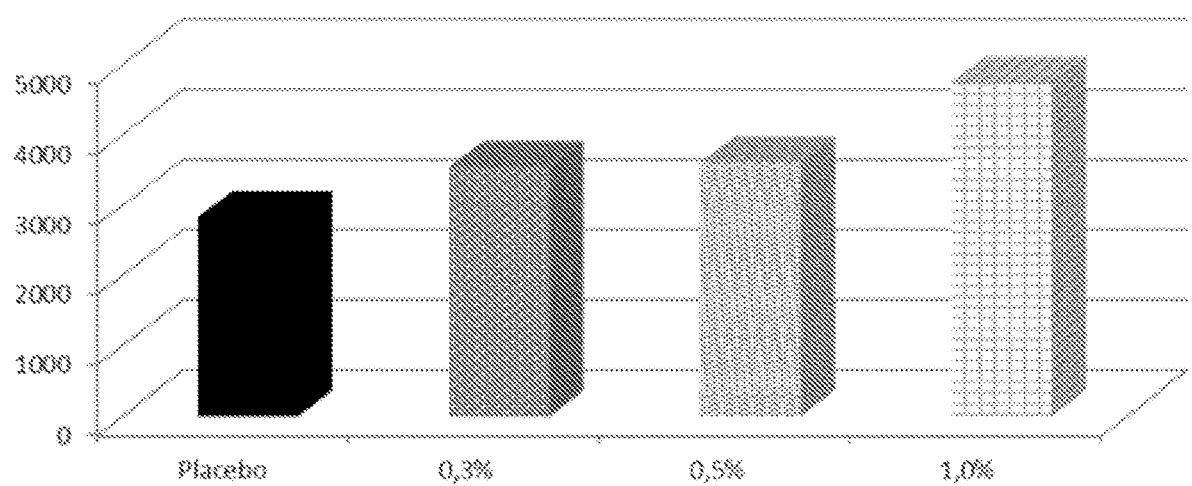
FIG. 3 shows the viscosity in η [mPas] (y-axis) of shampoos comprising 0.3, 0.5 or 1.0 wt.-% of glyceryl monocaprylate versus placebo.

FIG. 3 and Table 1.4 show the viscosity in η [mPas] (y-axis) of shampoos with 0.3, 0.5 or 1.0 wt.-% of glyceryl monocaprylate (trials B-D) versus placebo (without active, trial A).

The addition of glyceryl monocaprylate leads to an increase of viscosity in shampoo. By increasing the concentration of glyceryl monocaprylate, a dose dependent increase of viscosity could be observed versus shampoo without any active ingredient (placebo).

2.) Foam Volume in Hair & Body Wash Formulation

3-Hydroxypropyl caprylate and 3-hydroxypropyl undecylenate were incorporated into the shampoo formulation according to Table 1.1 above with a concentration of 1.0 wt.-% each (trials 4 and 7, Table 1.1).

In a second experiment, glyceryl monocaprylate was incorporated into the shampoo formulation according to Table 1.3 above with a concentration of 1 wt.-% (trial D, Table 1.3).

Figure 4:
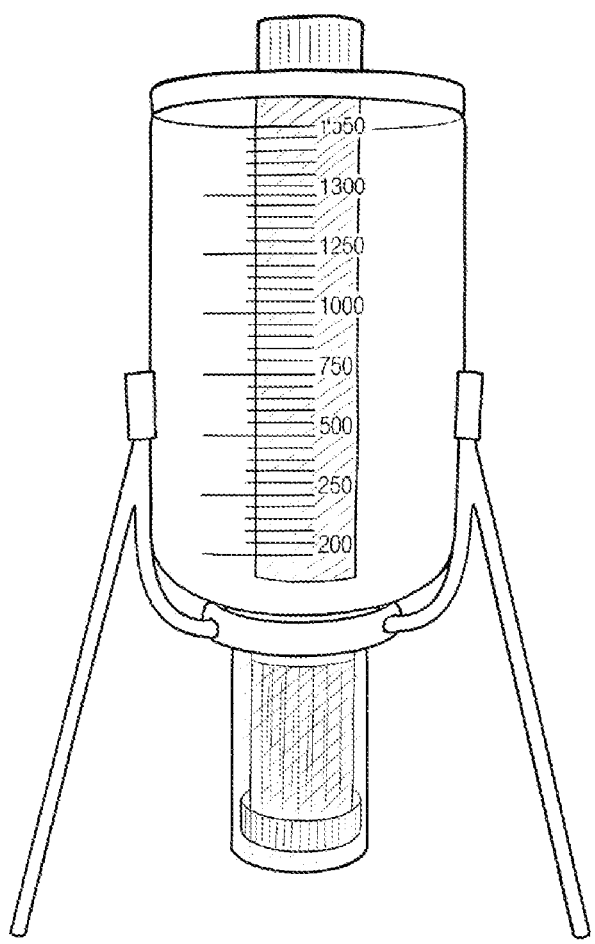
FIG. 4 shows an Ernst Haage foam volume measurement apparatus.

The foam volume of said formulations was determined by using an Ernst Haage foam volume measurement equipment (cf. FIG. 4). 200 ml of a 1 wt.-% solution of said formulations in demineralized water were prepared, respectively.

These solutions were poured into the glass beaker of the foam measurement apparatus. The stamp was pulled up and down for 2 minutes in a regular cycle. Subsequently, the foam volume was read off.

TABLE 1.5

Foam volume (ml) of shampoo trials 4 and 7 versus placebo (trial 1 without active) in 1 wt.-% solution

| | Placebo (trial 1) | 1% of 3-Hydroxypropyl caprylate (trial 4) | 1% of 3-Hydroxypropyl undecylenate (trial 7) |
|---|---|---|---|
| Foam volume (ml) | 950 | 1700 | 1325 |

Figure 5:
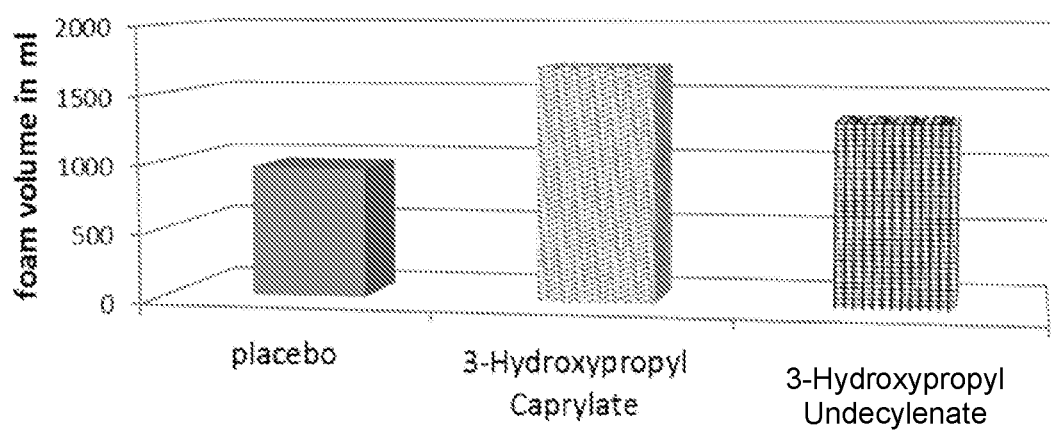
FIG. 5 shows foam volume in milimeters for shampoos comprising 3-hydroxypropyl caprylate and 3-hydroxypropyl undecylenate versus placebo.

It could be observed that the addition of formulations comprising 3-hydroxypropyl caprylate or 3-hydroxypropyl undecylenate (trials 4 and 7) leads to significantly higher foam volume versus the addition of the same formulation without active (placebo, trial 1). See also FIG. 5.

TABLE 1.6

Foam volume (ml) of shampoo trial D versus placebo (trial A without active) in 1 wt.-% solution

| | Placebo (trial A) | 1% of Glyceryl monocaprylate (trial D) |
|---|---|---|
| Foam volume (ml) | 1600 | 1850 |

Figure 6:
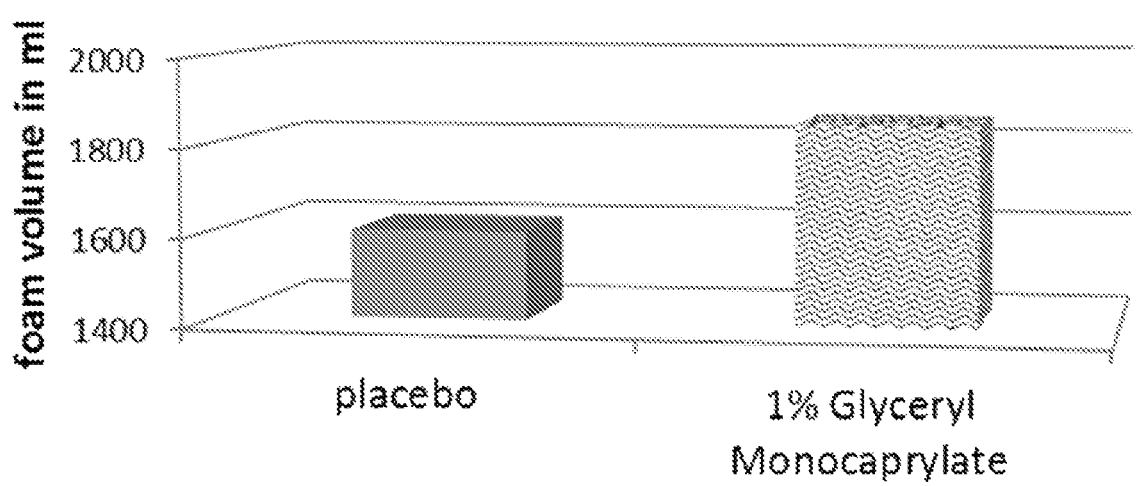
FIG. 6 shows that 1 wt.-% glyceryl monocaprylate (trial D) leads to significantly higher foam volume versus the addition of the same formulation without active (placebo, trial A).

It was observed that the addition of a formulation with 1 wt.-% glyceryl monocaprylate (trial D) leads to significantly higher foam volume versus the addition of the same formulation without active (placebo, trial A). See also FIG. 6.

3.) Formulation Examples

TABLE 2

Composition of perfume oil 1 (PO1, amounts in ‰ b.w.)

| Ingredients | Amount |
|---|---|
| ALDEHYDE C14 SO-CALLED | 2 |
| ALLYL AMYL GLYCOLATE 10% DPG | 5 |
| ANISIC ALDEHYDE PURE | 5 |
| APPLE OLIFFAC TYPE | 10 |
| Benzylacetat | 50 |
| BERGAMOT IDENTOIL ® COLOURLESS | 15 |
| CANTHOXAL | 5 |
| CETALOX 10% IPM | 3 |
| CITRONELLOL 950 | 40 |
| DAMASCENONE TOTAL 1% DPG | 5 |
| DAMASCONE ALPHA 10% DPG | 5 |
| DAMASCONE DELTA 10% DPG | 2 |
| DIMETHYL BENZYL CARBINYL BUTYRATE | 2 |
| DIPROPYLENE GLYCOL | 178 |
| EBANOL | 2 |
| ETHYL DECADIENOATE TRANS CIS-2.4 10% IPM | 2 |
| FLOROSA | 5 |
| FRAMBINON ® 10% DPG | 7 |
| GALAXOLIDE 50% IN IPM | 100 |
| GALBEX TYPE BASE | 1 |
| GERANYL ACETATE PURE | 2 |
| HEDIONE | 30 |
| HELIOTROPIN | 10 |
| HEXENYL ACETATE CIS-3 10% DPG | 1 |
| HEXENYL SALICYLATE CIS-3 | 5 |
| HEXYL CINNAMIC ALDEHYDE ALPHA | 70 |
| HEXYL SALICYLATE | 50 |
| HYDROXY CITRONELLAL | 10 |
| ISO E SUPER | 15 |
| ISORALDEINE 70 | 20 |
| LEAFOVERT ® | 1 |

TABLE 2-continued

Composition of perfume oil 1 (PO1, amounts in ‰ b.w.)

| Ingredients | Amount |
|---|---|
| LILIAL | 60 |
| LINALOOL | 60 |
| LINALYL ACETATE | 20 |
| LYRAL | 7 |
| MANZANATE | 2 |
| PHENOXANOL | 7 |
| PHENYLETHYL ALCOHOL | 120 |
| SANDAL MYSORE CORE | 2 |
| SANDRANOL ® | 7 |
| STYRALYL ACETATE | 3 |
| TAGETES RCO 10% TEC | 2 |
| TERPINEOL PURE | 20 |
| TETRAHYDROGERANIOL 10% DPG | 5 |
| TONALIDE | 7 |
| VERTOCITRAL 10% DPG | 5 |
| VERTOFIX | 15 |
| Total | 1000 |

TABLE 3

Composition of perfume oil 2 (PO2, amounts in ‰ b.w.)

| Ingredients | Amount |
|---|---|
| Acetophenone, 10% in DPG | 10 |
| n-Undecanal | 5 |
| Aldehyde C14, so-called (peach aldehyde) | 15 |
| Allylamyl glycolate. 10% in DPG | 20 |
| Amyl salicylate | 25 |
| Benzyl acetate | 60 |
| Citronellol | 80 |
| d-Limonene | 50 |
| Decenol trans-9 | 15 |
| Dihydromyrcenol | 50 |
| Dinnethylbenzylcarbinyl acetate | 30 |
| Diphenyloxide | 5 |
| Eucalyptol | 10 |
| Geraniol | 40 |
| Nerol | 20 |
| Geranium oil | 15 |
| Hexenol cis-3, 10% in DPG | 5 |
| Hexenyl salicylate cis-3 | 20 |
| Indole, 10% in DPG | 10 |
| Alpha-ionone | 15 |
| Beta-ionone | 5 |
| Lilial ® (2-methyl-3-(4-tert-butyl-phenyl)propanal) | 60 |
| Linalool | 40 |
| Methylphenyl acetate | 10 |
| Phenylethyl alcohol | 275 |
| Styrolyl acetate | 20 |
| Terpineol | 30 |
| Tetrahydrolinalool | 50 |
| Cinnamyl alcohol | 10 |
| Total: | 1000 |

TABLE 4

Composition of perfume oil 3 (PO3, amounts in ‰ b.w.)

| Ingredients | Amount |
|---|---|
| Benzyl acetate | 60 |
| Citronellyl acetate | 60 |
| Cyclamenaldehyde (2-methyl-3-(4-isopropylphenyl)propanal | 20 |
| Dipropylene glycol (DPG) | 60 |
| Ethyllinalool | 40 |
| Florol (2-isobutyl-4-methyltetrahydro-2H-pyran-4-ol) | 30 |
| Globanone ® [(E/Z)-8-cyclohexadecen-1-one] | 180 |
| Hedione ® (methyldihydrojasmonate) | 140 |

TABLE 4-continued

Composition of perfume oil 3 (PO3, amounts in ‰ b.w.)

| Ingredients | Amount |
| --- | --- |
| Hexenyl salicylate, cis-3 | 10 |
| Vertocitral (2.4-dimethyl-3-cyclohexenecarboxaldehyde) | 5 |
| Hydratropaldehyde, 10% in DPG | 5 |
| Isodamascone (1-(2.4.4-trimethyl-2-cyclohexen-1-yl)-2-buten-1-one. 10% in DPG | 5 |
| Isomuscone (cyclohexadecanone) | 40 |
| Jacinthaflor (2-methyl-4-phenyl-1.3-dioxolane) | 10 |
| Cis-jasmone, 10% in DPG | 20 |
| Linalool | 50 |
| Linalyl acetate | 30 |
| Methyl benzoate, 10% in DPG | 25 |
| para-Methyl cresol, 10% in DPG | 10 |
| Nerol | 20 |
| Phenylpropylaldehyde | 5 |
| 2-Phenylethyl alcohol | 82 |
| Tetrahydrogeraniol | 13 |
| 2.2-Dimethyl-3-cyclohexyl-1-propanol | 80 |
| Total: | 1000 |

TABLE 5

Composition of perfume oil 4 (PO4, amounts in ‰ b.w.)

| Ingredients | Amount |
| --- | --- |
| AMBRETTOLIDE (MACRO) | 10 |
| AMBROXIDE 10% in IPM | 10 |
| BENZYL ACETATE | 20 |
| BENZYL SALICYLATE | 15 |
| BERGAMOT OIL. bergapten-free | 60 |
| CALONE ® 1951 10% in DPG | 15 |
| COUMARIN | 5 |
| CYCLOGALBANATE ® 10% in DPG | 10 |
| ALPHA-DAMASCONE 1% in DPG | 20 |
| DIHYDROMYRCENOL | 10 |
| ETHYL LINALOOL | 75 |
| ETHYL LINALYLACETATE | 50 |
| ETHYL MALTOL 1% in DEP | 10 |
| ETHYLENE BRASSYLATE (MACRO) | 80 |
| FLOROSA | 40 |
| GERANYLACETATE | 10 |
| HEDIONE ® HC/30 | 35 |
| HEDIONE ® | 210 |
| HELIONAL ® | 15 |
| HELVETOLIDE ® (ALICYC) | 30 |
| HEXENYLSALICYLATE CIS-3 | 20 |
| ISO E SUPER ® | 40 |
| LEAFOVERT ® 10% in DEP | 10 |
| LILIAL ® | 80 |
| LYRAL ® | 20 |
| MANDARIN OIL | 10 |
| STYRALYL ACETATE | 5 |
| SYMROSE ® | 15 |
| VANILLIN 10% in DEP | 20 |
| DIPROPYLENE GLYCOL (DPG) | 50 |
| TOTAL | 1000 |

TABLE 6

Composition of perfume oil 5 (PO5, amounts in ‰ b.w.)

| Ingredients | Amount |
| --- | --- |
| AMAROCITE ® | 10 |
| AMBROCENIDE ® 10% in DPG | 5 |
| AMBROXIDE | 15 |
| AURELIONE ® (7/8-Cyclohexadecenone) (MACRO) | 70 |
| BERGAMOT OIL, bergapten-free | 90 |
| CALONE ® 1951 10% in DPG | 20 |
| CARAWAY OIL | 10 |
| CITRAL | 20 |
| COUMARIN | 10 |
| ALPHA-DAMASCONE 1% in DPG | 15 |
| DIHYDROMYRCENOL | 70 |
| ESTRAGON OIL | 10 |
| ETHYL LINALOOL | 100 |
| ETHYL LINALYLACETATE | 90 |
| EUGENOL | 10 |
| EVERNYL ® | 5 |
| FRUCTATE ® | 5 |
| GERANIUM OIL | 5 |
| HEDIONE ® HC/30 | 100 |
| HELIONAL ® | 10 |
| INDOLE 10% in DPG | 5 |
| ISO E SUPER ® | 100 |
| KEPHALIS ® | 5 |
| LAVENDER OIL | 40 |
| CITRUS OIL | 80 |
| LILIAL ® | 30 |
| MANDARIN OIL | 20 |
| MUSCENONE (MACRO) | 5 |
| SANDRANOL ® | 10 |
| VANILLIN 10% in DPG | 5 |
| DIPROPYLENE GLYCOL | 30 |
| TOTAL | 1000 |

The perfume oils PO1, PO2, PO3, PO4, or PO5 from the above examples were worked separately in each case into the formulations presented below.

Cosmetic formulations (compositions)—amounts are indicated as % by weight for all formulations.

TABLE 7

Cream o/w

| Ingredients | INCI | Amount |
| --- | --- | --- |
| Dracorin ® CE | Glyceryl Stearate Citrate | 1.0 |
| Lanette ® O | Cetearyl Alcohol | 2.0 |
| Cutina ® GMS-V | Glyceryl Stearate | 1.0 |
| Tegosoft ® MM | Myristyl Myristate | 1.0 |
| Xiameter ® PMX-0246, | Cyclohexasiloxane, Cyclopentasiloxane | 0.5 |
| Dragoxat ® 89 | Ethylhexyl Isononanoate | 2.0 |
| PCL-Liquid 100 | Cetearyl Ethylhexanoate | 4.0 |
| Neutral Oil | Caprylic/Capric Triglyceride | 4.0 |
| Carbopol ® Ultrez 21 | Acrylates/C10-30 Alkyl Acrylate Crosspolymer | 0.2 |
| Keltrol ® CG-T | Xanthan Gum | 0.1 |
| Water | Water (Aqua) | ad 100 |
| Glycerol 99.5 P. | Glycerol | 3.0 |
| Hydrolite CG | Caprylyl Glycol | 0.2 |
| 1.2-Propylene Glycol 99 P GC | Propylene Glycol | 2.0 |
| Sodium Benzoate | Sodium Benzoate | 0.1 |
| Sodium Hydroxide 10% solution | Sodium Hydroxide | 0.5 |
| Perfume oil PO1, PO2, PO3, PO4, or PO5 | Perfume | 0.3 |
| Euxyl ® K702 | Dehydroacetic Acid, Benzoic Acid. Phenoxyethanol, Polyaminopropyl Biguanide, Ethylhexylglycerin | 0.3 |
| 3-Hydroxypropyl caprylate | Propanediol Caprylate | 0.3 |
| 3-Hydroxypropyl undecylenate | Hydroxypropyl undecylenate | 0.1 |

TABLE 8

Hand and body cream

| Ingredients | INCI | Amount |
|---|---|---|
| Dracorin ® GOC | Glyceryl Oleate Citrate, Caprylic/Capric Triglyceride | 2.0 |
| PCL-Solid | Stearyl Heptanoate, Stearyl Caprylate | 2.5 |
| Lanette ® O | Cetearyl Alcohol | 1.5 |
| Cutina ® GMS-V | Glyceryl Stearate | 1.0 |
| Dragoxat ® 89 | Ethylhexyl Isononanoate | 3.0 |
| PCL-Liquid 100 | Cetearyl Ethylhexanoate | 7.0 |
| Isodragol ® | Triisononanoin | 4.0 |
| Xiameter ® PMX-0345 Cyclosiloxane | Cyclopentasiloxane (and) Cyclohexasiloxane | 0.5 |
| Water | Water (Aqua) | ad 100 |
| Carbopol ® Ultrez 21 | Acrylates/C10-30 Alkyl Acrylate Crosspolymer | 0.2 |
| Keltrol ® CG-RD | Xanthan Gum | 0.1 |
| Glycerol 85 P, | Glycerol | 3.0 |
| DragoBetaGlucan | Water (Aqua), Butylene Glycol, Glycerol, Avena Sativa (Oat) Kernel Extract | 1.5 |
| Potassium Sorbate | Potassium Sorbate | 0.1 |
| Hydrolite-6 | 1,2 Hexanediol | 1.0 |
| Sodium Hydroxide 10% solution | Sodium Hydroxide | 0.5 |
| Perfume oil PO1, PO2, PO3, PO4, or PO5 | Fragrance | 0.2 |
| 3-Hydroxypropyl caprylate | Propanediol Caprylate | 0.2 |
| Glyceryl monocaprylate | Glyceryl caprylate | 0.05 |

TABLE 9

Daily face cream SPF 20

| Ingredients | Amount |
|---|---|
| SymOcide PH | 1 |
| Phenoxyethanol, Hydroxyacetophenone, Caprylyl Glycol, Water (Aqua) | |
| Ascorbyl Palmitate | 0.1 |
| Ascorbyl Palmitate | |
| Biotive L-Arginine | 0.2 |
| Arginine | |
| Buriti oil | 1 |
| Mauritia Flexuosa Fruit Oil | |
| Cocoa butter | 2 |
| Theobroma Cacao (Cocoa) Seed Butter | |
| Dimethicone | 0.5 |
| Dimethicone | |
| Disodium EDTA | 0.1 |
| Disodium EDTA | |
| Dragosantol 100 | 0.1 |
| Bisabolol | |
| Dragoxat 89 | 5 |
| Ethylhexyl Isononanoate | |
| Emulsiphos | 2 |
| Potassium Cetyl Phosphate, Hydrogenated Palm Glycerides | |
| Extrapone Corail | 1 |
| Glycerin, Aqua, Hydrolyzed Corallina Officinalis | |
| Glycerin | 3 |
| Glycerin | |
| Isoadipate | 5 |
| Diisopropyl Adipate | |
| Jojoba Wax Flakes | 1 |
| Hydrogenated Jojoba Oil | |
| Keltrol CG-T | 0.1 |
| Xanthan Gum | |
| Lanette O | 5 |
| Cetearyl Alcohol | |
| Lanette 16 | 1 |
| Cetyl Alcohol | |
| Lanette 22 | 1 |
| Behenyl Alcohol | |
| Neo Heliopan 357 | 3 |
| Butyl Methoxydibenzoylmethane | |

TABLE 9-continued

Daily face cream SPF 20

| Ingredients | Amount |
|---|---|
| Neo Heliopan HMS | 10 |
| Homosalate | |
| Neo Heliopan Hydro used as a 25% aq, Solution neutralized by arginine | 8 |
| Phenylbenzimidazole Sulfonic Acid | |
| Neo Heliopan OS | 5 |
| Ethylhexyl Salicylate | |
| Orgasol Caresse | 1 |
| Polyamide-5 | |
| Perfume oil PO1, PO2, PO3, PO4, or PO5 | 0.1 |
| Shea butter | 3 |
| Butyrospermum Parkii (Shea) Butter | |
| Simugel EG | 1 |
| Sodium Acrylate/Sodium Acryloyldimethyl Taurate Copolymer. Isohexadecane. Polysorbate 80 | |
| SymFinity 1298 | 0.1 |
| Echinacea Purpurea Extract | |
| SymDiol 68 | 0.5 |
| 1.2 Hexanediol. Caprylyl Glycol | |
| SymMatrix | 0.1 |
| Maltodextrin, Rubus Fructicosus (Blackberry) Leaf Extract | |
| SymSitive 1609 | 1 |
| Pentylene Glycol, 4-t-Butylcyclohexanol | |
| Tegosoft TN | 4 |
| C12-15 Alkyl Benzoate | |
| 3-Hydroxypropyl caprylate | 0.3 |
| Glyceryl monoundecylenate | 0.1 |
| Water | ad 100 |
| Aqua | |

TABLE 10 w/o night cream

| Ingredients | INCI | Amount |
|---|---|---|
| 3-Hydroxypropyl caprylate | Propanediol Caprylate | 0.15 |
| Glyceryl monocaprylate | Glyceryl caprylate | 0.15 |
| 3-Hydroxypropyl undecylenate | Hydroxypropyl undecylenate | 0.1 |
| Aloe Vera Gel Concentrate 10/1 | Water (Aqua), Aloe Barbadensis Leaf Juice | 3.0 |
| Alugel 34 TH | Aluminium Stearate | 1.0 |
| Dragosan W/O P | Sorbitan Isostearate, Hydrogenated Castor Oil, Ceresin, Beeswax (Cera Alba) | 6.0 |
| Dragosantol ® 100 | Bisabolol | 0.2 |
| Extrapone ® Witch Hazel Distillate colourless | Propylene Glycol, Hamamelis Virginiana (Witch Hazel) Water, Water (Aqua), Hamamelis Virginiana (Witch Hazel) Extract | 1.0 |
| Perfume oil PO1, PO2, PO3, PO4, or PO5 | Fragrance | 0.4 |
| Glycerol 85% | Glycerin | 2.0 |
| Hydrolite-5 | Pentylene Glycol | 0.5 |
| Karion F | Sorbitol | 2.0 |
| Magnesium Chloride | Magnesium Chloride | 0.7 |
| PCL Liquid 100 | Cetearyl Ethylhexoate | 12.0 |
| Retinyl Palmitate in Oil | Retinyl Palmitate | 0.2 |
| Sun Flower Oil | Helianthus Annuus (Sunflower) Seed Oil | 5.0 |
| Sweet Almond Oil | Prunus dulcis | 5.0 |
| SymMatrix ® | Maltodextrin, Rubus Fruticosus (Blackberry) Leaf Extract | 1.0 |
| SymOcide PS | Phenoxyethanol, Decylene glycol, 1,2-Hexanediol | 1.0 |
| SymVital ® AgeRepair | Zingiber Officinale (Ginger) Root Extract | 0.1 |
| Tocopherol Acetate | Tocopheryl Acetate | 3.0 |
| Water (demineralized) | Water (Aqua) | ad 100 |

TABLE 11

Body lotion

| Ingredients | Amount |
| --- | --- |
| Cetearyl Alcohol | 2.0 |
| Ethylhexyl Isononanoate | 5.0 |
| Cetearyl Ethylhexanoate, Isopropyl Myristate | 3.0 |
| Glyceryl Oleate Citrate, Caprylic/Capric Triglyceride | 4.0 |
| Water (Aqua) | ad 100 |
| Pentylene Glycol | 3.0 |
| Carbomer | 0.3 |
| Sodium Benzoate | 0.1 |
| Propylene Glycol | 5.0 |
| Sodium Hydroxide 30% solution | 0.3 |
| Perfume oil PO1, PO2, PO3, PO4, or PO5 | 0.3 |
| Triethylene Glycol, Imidazolidinyl Urea, Methylparaben, Propylparaben, Dehydroacetic Acid | 0.3 |
| 3-Hydroxypropyl caprylate | 0.2 |
| 3-Hydroxypropyl undecylenate | 0.2 |

TABLE 12

Antibacterial body lotion, sprayable

| Ingredients | INCI | Amount |
| --- | --- | --- |
| 3-Hydroxypropyl caprylate | Propanediol Caprylate | 0.15 |
| Glyceryl monocaprylate | Glyceryl caprylate | 0.15 |
| 3-Hydroxypropyl undecylenate | Hydroxypropyl undecylenate | 0.05 |
| Glyceryl monoundecylenate | Glyceryl undecylenate | 0.05 |
| Triethyl Citrate | Triethyl Citrate | 0.2 |
| 2,4-Hexadienoic acid, potassium salt | Sorbic acid, potassium salt | 0.2 |
| Dow Corning 345 Fluid | Cyclomethicone | 0.5 |
| Dracorin ® GOC | Glyceryl Oleate Citrate, Caprylic/Capric Triglyceride | 2.0 |
| Drago-Calm | Water, Glycerin, Avena Sativa (Oat) Kernel Extract | 1.0 |
| Dragosantol ® 100* | Bisabolol | 0.1 |
| Perfume oil PO1, PO2, PO3, PO4, or PO5 | Fragrance | 0.3 |
| Hydrolite ® -5 | Pentylene Glycol | 5.0 |
| Neutral Oil | Caprylic/Capric Triglyceride | 4.0 |
| Paraffin Oil | Mineral Oil | 4.0 |
| PCL Liquid 100 | Cetearyl Ethylhexoate | 7.0 |
| Pemulen TR-2 | Acrylates/C10-30 Alkyl Acrylate Crosspolymer | 0.2 |
| Sodium Hydroxide (10% sol,) | Sodium Hydroxide | 0.4 |
| SymDeo ® MPP | Dimethyl Phenylbutanol | 0.5 |
| SymRelief ® 100 | Bisabolol, Zingiber Officinale (Ginger) Root Extract | 0.1 |
| Water (demineralized) | Water (Aqua) | ad 100 |

TABLE 13

Aseptic wound cream

| Ingredients | Amount |
| --- | --- |
| Sorbitan Isostearate, Hydrogenated Castor Oil, Ceresin, Beeswax (Cera Alba) | 6.0 |
| Petrolatum | 21.0 |
| Cera Alba | 5.0 |
| Cetearyl Alcohol | 7.0 |
| Prunus Dulcis | 7.0 |
| Lanolin | 5.0 |
| Paraffinum Liquidum | 12.0 |
| Perfume oil PO1, PO2, PO3, PO4 or PO5 | 0.3 |
| Water (Aqua) | ad 100 |
| Panthenol | 7.0 |
| Magnesium Sulfate | 0.7 |
| Pentylene Glycol | 1.0 |
| Tocopheryl Acetate | 1.0 |
| Octenidine dihydrochloride | 0.1 |
| Phenoxyethanol | 0.5 |
| 3-Hydroxypropyl caprylate | 0.4 |
| Glyceryl monocaprylate | 0.2 |

TABLE 14

Anti acne balm

| Ingredients | INCI | Amount |
| --- | --- | --- |
| 3-Hydroxypropyl caprylate | Propanediol Caprylate | 0.3 |
| 3-Hydroxypropyl undecylenate | Hydroxypropyl undecylenate | 0.2 |
| Abil 350 | Dimethicone | 1.0 |
| Allantoin | Allantoin | 0.1 |
| Aloe Vera Gel Concentrate 10/1 * | Water (Aqua), Aloe Barbadensis Leaf Juice | 3.0 |
| Azelaic Acid | Azelaic Acid | 5.0 |
| Cetiol OE | Dicaprylyl Ether | 4.0 |
| Cetiol SB 45 | Butyrospermum Parkii (Shea Butter) | 1.0 |
| D-Panthenol | Panthenol | 1.0 |
| SymClariol | Decylene Glycol | 0.1 |
| Emulsiphos ® | Potassium Cetyl Phosphate, Hydrogenated Palm Glycerides | 2.0 |
| Perfume oil PO1, PO2, PO3, PO4, or PO5 | Fragrance | 0.2 |
| Frescolat ® ML cryst, | Menthyl Lactate | 0.8 |
| Glycerol 85% | Glycerin | 4.0 |
| Hydroviton ® PLUS | Water, Pentylene Glycol, Glycerin, Fructose, Urea, Citric Acid, Sodium Hydroxide, Maltose, Sodium PCA, Sodium Chloride, Sodium Lactate, Trehalose, Allantoin, Sodium hyaluronate, Glucose | 1.0 |
| Lara Care A-200 | Galactoarabinan | 0.3 |
| Pemulen TR-2 | Acrylates/C10-30 Alkyl Acrylate Crosspolymer | 0.2 |
| Sodium Hydroxide (10% aqueous sol.) | Sodium Hydroxide | 0.4 |
| SymOcide PH | Hydroxyacetophenone, Phenoxyethanol, Caprylyl glycol, Aqua | 1.0 |
| Tegosoft TN | C12-15 Alkyl Benzoate | 5.0 |
| Tocopherol Acetate | Tocopheryl Acetate | 0.5 |
| Water (demineralized) | Water (Aqua) | ad 100 |

TABLE 15

Barrier repair cream

| Ingredients | INCI | Amount |
| --- | --- | --- |
| 3-Hydroxypropyl caprylate | Propanediol Caprylate | 0.1 |
| Glyceryl monocaprylate | Glyceryl caprylate | 0.1 |
| 3-Hydroxypropyl undecylenate | Hydroxypropyl undecylenate | 0.1 |
| Glyceryl monoundecylenate | Glyceryl undecylenate | 0.1 |
| Abil 350 | Dimethicone | 0.5 |
| Allantoin | Allantoin | 0.25 |
| Ceramide BIO* | Cetylhydroxyproline Palmitamide | 0.5 |
| Dracorin ® CE | Glyceryl Stearate Citrate | 1.5 |
| Dragoxat ® 89 | Ethylhexyl Ethylisononan-oate | 2.0 |
| Emulsiphos ® | Potassium Cetyl Phosphate, Hydrogenated Palm Glycerides | 2.0 |
| Extrapone ® Rosemary GW | Glycerin, Water (Aqua), Rosmarinus officinalis (Rosemary) Leaf Extract | 0.5 |
| Perfume oil PO1, PO2, PO3, PO4, or PO5 | Fragrance | 0.1 |

TABLE 15-continued

Barrier repair cream

| Ingredients | INCI | Amount |
|---|---|---|
| Glycerol 85% | Glycerin | 3.0 |
| Glyceryl Stearate | Glyceryl Stearate | 2.0 |
| Hydroviton ® 24 | Water, Glycerin, Sodium Lactate, TEA Lactate, Serine, Lactic Acid, Urea, Sorbitol, Sodium Chloride, Lauryl Diethylenedi-aminoglycine, Lauryl Aminopropyl-glycine, Allantoin | 1.0 |
| Hydrolite-5 Green | Pentylene Glycol | 1.0 |
| Isodragol ® | Triisononanoin | 3.0 |
| Lanette O | Cetearyl Alcohol | 2.0 |
| NaOH 10% sol. | Sodium Hydroxide | 0.3 |
| Neutral Oil | Caprylic/Capric Triglyceride | 10.0 |
| SymCalmin ® | Pentylene Glycol, Butylene Glycol, Hydroxyphenyl Propamidobenzoic Acid | 1.0 |
| SymRepair ® 100 | Hexyldecanol, Bisabolol, Cetylhydroxyproline, Palmitamide, Stearic Acid, Brassica Campestris (Rapeseed) Sterols | 2.0 |
| SymTriol | Caprylyl glycol, 1,2-Hexanediol, Methylbenzyl alcohol | 1.0 |
| Tegosoft PC 31 | Polyglyceryl 3-Caprate | 0.3 |
| Tocopherol Acetate | Tocopheryl Acetate | 0.3 |
| Water (demineralized) | Water (Aqua) | ad 100 |

TABLE 16

Skin soothing lotion

| Ingredients | INCI | Amount |
|---|---|---|
| 3-Hydroxypropyl caprylate | Propanediol Caprylate | 0.3 |
| Glyceryl monocaprylate | Glyceryl caprylate | 0.05 |
| 3-Hydroxypropyl undecylenate | Hydroxypropyl undecylenate | 0.2 |
| Glyceryl monoundecylenate | Glyceryl undecylenate | 0.05 |
| Abil 350 | Dimethicone | 2.0 |
| Allantoin | Allantoin | 0.2 |
| Carbopol Ultrez-10 | Carbomer | 0.1 |
| Ceramide BIO* | Cetylhydroxyproline Palmitamide | 0.1 |
| Citric Acid 10% sol. | Citric Acid | 0.4 |
| Emulsiphos ® | Potassium Cetyl Phosphate, Hydrogenated Palm Glycerides | 2.0 |
| Extrapone ® Green Tea GW | Glycerin, Water (Aqua), Camellia Sinensis Leaf Extract | 0.2 |
| Extrapone ® Rosemary GW | Glycerin, Water (Aqua), Rosmarinus officinalis (Rosemary) Leaf Extract | 0.3 |
| Perfume oil PO1, PO2, PO3, PO4, or PO5 | Fragrance | 0.3 |
| Glycerol 85% | Glycerin | 2.0 |
| Glyceryl Stearate | Glyceryl Stearate | 2.0 |
| Isodragol ® | Triisononanoin | 2.0 |
| Keltrol RD | Xanthan Gum | 0.1 |
| Lanette O | Cetearyl Alcohol | 3.0 |
| Neo PCL wssl. N | Trideceth-9, PEG-5 Ethylhexanoate, Water | 1.0 |
| PCL Liquid 100 | Cetearyl Ethylhexanoate | 5.0 |
| PCL Solid | Stearyl Heptanoate, Stearyl Caprylate | 2.0 |
| Propylene Glycol | Propylene Glycol | 5.0 |
| Sodium Hydroxide (10% aqueous sol.) | Sodium Hydroxide | 0.3 |
| SymCalmin ® | Pentylene Glycol, Butylene Glycol, Hydroxyphenyl Propamidobenzoic Acid | 2.0 |
| SymMatrix ® | Maltodextrin, Rubus Fruticosus (Blackberry) Leaf Extract | 0.1 |
| SymSave H | Hydroxyacetophenone | 0.4 |
| 2-Phenoxyethyl Alcohol | Phenoxyethanol | 0.4 |

TABLE 16-continued

Skin soothing lotion

| Ingredients | INCI | Amount |
|---|---|---|
| SymSitive ®1609 | Pentylene Glycol, 4-t-Butylcyclohexanol | 1.5 |
| Water (demineralized) | Water (Aqua) | ad 100 |

TABLE 17

Baby Nappy Rash Cream w/o

| Ingredients | Amount |
|---|---|
| SymOcide PH<br>Phenoxyethanol, Hydroxyacetophenone, Caprylyl Glycol, Water (Aqua) | 1 |
| Cupuaçu butter<br>Theobroma Grandiflorum Seed Butter | 1 |
| Cutina HR Powder<br>Hydrogenated Castor Oil | 1.5 |
| Dehymuls PGPH<br>Polyglyceryl-2 Dipolyhydroxystearate | 5 |
| Glycerin<br>Glycerin | 5 |
| Jojoba oil<br>Simmondsia Chinensis (Jojoba) Seed Oil | 5 |
| Magnesium Sulfate Hepta Hydrate<br>Magnesium Sulfate | 0.5 |
| Monomuls 90-O18<br>Glyceryl Oleate | 1 |
| Neutral oil<br>Caprylic/capric triglyceride | 8 |
| PCL Liquid 100<br>Cetearyl Ethylhexanoate | 5 |
| SymCalmin<br>Butylene Glycol, Pentylene Glycol, Hydroxyphenyl Propamidobenzoic Acid | 1 |
| Tamanu oil<br>Calophyllum Inophyllum Seed Oil | 0.2 |
| Tetrasodium EDTA<br>Tetrasodium EDTA | 0.1 |
| Titan dioxide<br>Titan dioxide | 4 |
| Water<br>Aqua | ad 100 |
| Wheat germ oil<br>Triticum Vulgare (Wheat) Germ Oil | 2 |
| Zinc oxide<br>Zinc oxide | 10 |
| 3-Hydroxypropyl caprylate | 0.3 |
| 3-Hydroxypropyl undecylenate | 0.15 |

TABLE 18

Skin lightening day cream o/w

| Ingredients | INCI | Amount |
|---|---|---|
| 3-Hydroxypropyl caprylate | Propanediol Caprylate | 0.1 |
| Glyceryl monocaprylate | Glyceryl caprylate | 0.1 |
| 3-Hydroxypropyl undecylenate | Hydroxypropyl undecylenate | 0.05 |
| Glyceryl monoundecylenate | Glyceryl undecylenate | 0.05 |
| Abil 350 | Dimethicone | 0.5 |
| Dracorin ® CE | Glyceryl Stearate Citrate | 2.5 |
| Dracorin ® GOC | Glyceryl Oleate Citrate, Caprylic/Capric Triglyceride | 0.5 |
| Drago-Beta-Glucan | Water (Aqua), Butylene Glycol, Glycerin, Avena Sativa (Oat), Kernel Extract | 0.3 |
| Dragosantol ® 100 | Bisabolol | 0.2 |

TABLE 18-continued

Skin lightening day cream o/w

| Ingredients | INCI | Amount |
|---|---|---|
| Perfume oil PO1, PO2, PO3, PO4, or PO5 | Fragrance | 0.1 |
| Frescolat ® MGA | Menthone Glycerol Acetal | 0.5 |
| Glycerol 85% | Glycerin | 3.0 |
| Isopropyl Palmitate | Isopropyl Palmitate | 4.0 |
| Keltrol RD | Xanthan Gum | 0.2 |
| Lanette 16 | Cetyl Alcohol | 1.0 |
| Neo Heliopan ® AV | Ethylhexyl Methoxy-cinnamate | 5.0 |
| Neutral Oil | Caprylic/Capric Triglyceride | 6.0 |
| PCL Liquid 100 | Cetearyl Ethylhexoate | 3.0 |
| Sodium Benzoate | Sodium Benzoate | 0.1 |
| Symdiol ® 68T | 1,2-Hexanediol, Caprylylglycol, Tropolone | 0.5 |
| SymVital ® AgeRepair | Zingiber Officinale (Ginger) Root Extract | 0.1 |
| SymWhite ® 377 | Phenylethyl Resorcinol | 0.5 |
| Water (demineralized) | Water (Aqua) | ad 100 |

TABLE 19

Shampoo

| Ingredients | Amount |
|---|---|
| 4-Hydroxyacetophenone (SymSave H) Hydroxyacetophenone | 0.3 |
| Antil 127 PEG-120 Methyl Glucose Dioleate | 0.5 |
| Brazilian nut oil Bertholletia Excelsa Seed Oil | 0.5 |
| Cocamidopropyl Betaine 38% Cocamidopropyl Betaine | 5 |
| Octopirox Piroctone olamine | 0.3 |
| Dragoderm Glycerin, Triticum Vulgare Gluten. Aqua | 0.5 |
| Fragrance Perfum | 0.5 |
| Glycerin Glycerin | 0.5 |
| Jojoba oil Simmondsia Chinensis (Jojoba) Seed Oil | 0.5 |
| Marlinat 242/90 M MIPA Laureth Sulfate, Propylene Glycol | 15 |
| Marlowet CG PEG-18 Castor Oil Dioleate | 2 |
| Plantacare 1200 UP Lauryl Glucoside | 0.5 |
| Polyquaternium-10 Polyquaternium-10 | 0.3 |
| Sodium Chloride Sodium Chloride | 1.5 |
| SymCalmin Butylene Glycol, Pentylene Glycol, Hydroxyphenyl Propamidobenzoic Acid | 1 |
| SymOcide PS Phenoxyethanol, Decylene Glycol, 1,2-Hexanediol | 0.8 |
| 3-Hydroxypropyl caprylate | 0.4 |
| 3-Hydroxypropyl undecylenate | 0.2 |
| Water Aqua | ad 100 |

TABLE 20

Anti dandruff shampoo

| Ingredients | INCI | Amount |
|---|---|---|
| 3-Hydroxypropyl caprylate | Propanediol Caprylate | 0.3 |
| 3-Hydroxypropyl undecylenate | Hydroxypropyl undecylenate | 0.15 |
| Aloe Vera Gel Concentrate 10/1 | Water (Aqua), Aloe Barbadensis Leaf Juice | 0.5 |
| Abrasive/Exfoliant | Perlite | 0.3 |
| Cellulose fibre | Microcrystalline Cellulose | 0.1 |
| Avocado oil | Persea Gratissima (Avocado) Oil | 0.5 |
| Citric Acid 10% sol. | Citric Acid | 0.3 |
| Comperlan 100 | Cocamide MEA | 0.5 |
| Crinipan AD | Climbazole | 0.2 |
| Dragoderm ® | Glycerin, Triticum Vulgare (Wheat) Gluten, Water (Aqua) | 2.0 |
| Perfume oil PO1, PO2, PO3, PO4, or PO5 | Fragrance | 0.5 |
| Genapol LRO liquid | Sodium Laureth Sulfate | 37.0 |
| Merquat 550 | Polyquaternium-7 | 0.5 |
| Xylityl Caprylate | Xylityl Caprylate | 0.5 |
| Sodium Chloride | Sodium Chloride | 1.0 |
| Hydrolite-5 Green | Pentylene Glycol | 0.5 |
| SymSave ® H | Hydroxyacetophenone | 0.8 |
| Tego Betain L7 | Cocamidopropyl Betaine | 6.0 |
| Water (demineralized) | Water (Aqua) | ad 100 |

TABLE 21

2-in-1 Shampoo

| Ingredients | INCI Name | Amount |
|---|---|---|
| Deionized water | Water | ad 100 |
| Shea butter | Butyrospermum Parkii (Shea) Butter | 0.1 |
| SymSave H | Hydroxyacetophenone | 0.5 |
| SymDiol 68 | 1.2 Hexanediol, Caprylyl Glycol | 0.5 |
| Plantacare PS 10 | Sodium Laureth Sulfate, Lauryl Glucoside | 20.0 |
| Euperlan PK 771 | Glycol Distearate, Sodium Lauryl Sulfate, Cocamide MEA, Laureth-10 | 6.0 |
| Sodium chloride | Sodium Chloride | 1.4 |
| Citric acid monohydrate crystalline | Citric acid | 0.1 |
| Perfume oil PO1, PO2, PO3, PO4, or PO5 | Fragrance | 0.5 |
| Zinc Omadine | Zinc pyrithione | 0.10 |
| 3-Hydroxypropyl caprylate | Propanediol Caprylate | 0.3 |
| 3-Hydroxypropyl undecylenate | Hydroxypropyl undecylenate | 0.15 |

TABLE 22

Body wash

| Ingredients | INCI | Amount |
|---|---|---|
| Lumerol K 28 | Disodium Laureth Sulfosuccinate, Cocamidopropyl Betaine, Magnesium Lauryl Sulfate | 33.0 |
| Amphotensid B 4 | Cocamidopropyl Betaine | 10.0 |
| Pearly Gloss | MIPA-Pareth-25 Sulfate, Glycol Stearate | 4.0 |
| Sodium Chloride | Sodium Chloride | 2.0 |
| Avocado oil | Persea Gratissima (Avocado) Oil | 3.0 |
| SymSave H | Hydroxyacetophenone | 0.8 |
| Hydrolite-5 Green | Pentylene Glycol | 1.0 |
| Water | Water | ad 100 |
| Perfume oil PO1, PO2, PO3, PO4, or PO5 | Fragrance | 0.5 |
| 3-Hydroxypropyl caprylate | Propanediol Caprylate | 0.15 |
| Glyceryl monocaprylate | Glyceryl caprylate | 0.15 |
| 3-Hydroxypropyl undecylenate | Hydroxypropyl undecylenate | 0.1 |
| Glyceryl monoundecylenate | Glyceryl undecylenate | 0.1 |

TABLE 23

Shower gel

| Ingredients | INCI | Amount |
|---|---|---|
| Deionized water | Water | ad 100 |
| Shea butter | Butyrospermum Parkii (Shea) Butter | 1.0 |
| Plantacare PS 10 | Sodium Laureth Sulfate, Lauryl Glucoside | 20.0 |
| Hydrolite-6 | 1.2 Hexanediol | 0.5 |
| Dehydroacetic acid | Dehydroacetic acid | 0.2 |
| SymSave H | Hydroxyacetophenone | 0.3 |
| Sodium chloride | Sodium Chloride | 1.4 |
| Citric acid monohydrate crystalline | Citric Acid | 1.3 |
| Perfume oil PO1, PO2, PO3, PO4, or PO5 | Fragrance | 0.6 |
| 3-Hydroxypropyl caprylate | Propanediol Caprylate | 0.1 |
| Glyceryl monocaprylate | Glyceryl caprylate | 0.3 |
| 3-Hydroxypropyl undecylenate | Hydroxypropyl undecylenate | 0.2 |

TABLE 24

Intimate wash

| Ingredients | INCI | Amount |
|---|---|---|
| Tegobetaine HS | Cocamidopropyl Betaine, Glyceryl Laurate | 15.0 |
| Tagat L 2 | PEG-20 Glyceryl Laurate | 2.0 |
| Arlacide G | Chlorhexidine Digluconate | 0.1 |
| Rewoquat B 50 | Benzalkonium Chloride | 0.1 |
| Lactic Acid. 80% | Lactic Acid | 0.1 |
| euxyl ® K700 | Potassium Sorbate, Benzyl Alcohol. Phenoxyethanol | 0.3 |
| Water | Water | ad 100 |
| Perfume oil PO1, PO2, PO3, PO4, or PO5 | Fragrance | 0.2 |
| 3-Hydroxypropyl caprylate | Propanediol Caprylate | 0.3 |
| Hydrolite-5 Green | Pentylene Glycol | 0.3 |
| Glyceryl monocaprylate | Glyceryl caprylate | 0.1 |
| 3-Hydroxypropyl undecylenate | Hydroxypropyl undecylenate | 0.1 |
| Glyceryl monoundecylenate | Glyceryl undecylenate | 0.05 |

TABLE 25

Liquid soap. transparent

| Ingredients | INCI | Amount |
|---|---|---|
| Tagat O 2 | PEG-20 Glyceryl Oleate | 2.5 |
| Coconut oil diethanolamine condensate | Cocamide DEA | 5.0 |
| Abil B 8842 | Cyclomethicone | 0.5 |
| Sodium laurylethersulfate, 28% | Sodium Laureth Sulfate | 35.0 |
| Tego-Betaine L7 | Cocamidopropyl Betaine | 5.0 |
| Soap, 25% | Coconut acid, Potassium salt, Potassium Oleate | 20.0 |
| Perfume oil PO1, PO2, PO3, PO4, or PO5 | Fragrance | 0.4 |
| Preservative | DMDM Hydantoin | 0.2 |
| 3-Hydroxypropyl caprylate | Hydroxypropyl caprylate | 0.15 |
| Glyceryl monocaprylate | Glyceryl caprylate | 0.15 |
| Water | Water | ad 100 |

TABLE 26

Syndet soap, liquid

| Ingredients | INCI | Amount |
|---|---|---|
| Elfan OS 46 | Sodium Olefin C14-C16 Sulfonate | 35.5 |
| Armoteric LB | Lauryl Betaine | 8.0 |
| Euperlan PK 3000 OK | Glycol Distearate, Glycerin, Laureth-4, Cocamidopropyl Betaine | 10.0 |
| Elfacos GT 282 L | Talloweth-60 Myristyl Glycol | 3.0 |
| PCL-Liquid 100 | Cetearyl Ethylhexanoate | 4.0 |
| Perfume oil PO1, PO2, PO3, PO4, or PO5 | Fragrance | 0.4 |
| SymSave H | 4-Hydroxyacetophenone | 0.6 |
| 3-Hydroxypropyl caprylate | Propanediol Caprylate | 0.15 |
| 3-Hydroxypropyl undecylenate | Hydroxypropyl undecylenate | 0.25 |
| Water | Water | ad 100 |

TABLE 27

Anti-acne wash

| Ingredients | Amount |
|---|---|
| Water (Aqua) | ad 100 |
| Polyquaternium-7 | 0.5 |
| Cocamidopropyl Betaine | 9.0 |
| Coco Glucoside | 2.0 |
| Polysorbate 80, Glycerol, Gossypium Herbaceum (Cotton) Seed Oil, Water (Aqua) | 1.0 |
| Trideceth-9, PEG-5 Ethylhexanoate, Water (Aqua) | 1.0 |
| Glycereth-90 Isostearate, Laureth-2 | 0.5 |
| Sodium Laureth Sulfate | 37.0 |
| Glycerol, Triticum Vulgare (Wheat) Gluten, Water (Aqua) | 1.0 |
| Sodium Chloride | 0.3 |
| Perfume oil PO1, PO2, PO3, PO4, or PO5 | 1.0 |
| SymOcide BHO (Hydroxyacetophenone, Benzyl alcohol, Caprylyl glycol, Water) | 1.0 |
| 3-Hydroxypropyl caprylate | 0.25 |
| 3-Hydroxypropyl undecylenate | 0.15 |

TABLE 28

Mineral wash and cleaning gel

| Ingredients | INCI | Amount |
|---|---|---|
| Water | Water (Aqua) | ad 100 |
| Pionier ® NP 37 G | Sodium Carbomer | 1.5 |
| SymSol ® PF-3 | Water (Aqua), Pentylene Glycol, Sodium Lauryl Sulfoacetate, Sodium Oleoyl Sarcosinate, Sodium Chloride, Disodium Sulfoacetate, Sodium Oleate, Sodium Sulfate | 5.0 |
| Hydroviton ® 24 | Water (Aqua), Pentylene Glycol. Glycerol, Sodium Lactate, Lactic Acid, Serine, Urea, Sorbitol, Sodium Chloride, Allantoin | 1.0 |
| Extrapone ® Silk GW | Water (Aqua), Glycerol, Hydrolyzed Silk | 1.0 |
| Hydrolite ® 5 | Pentylene Glycol | 4.0 |
| Actipearls Red Star # DH10402/6 | Water (Aqua), Propylene Glycol, Algin, Gellan Gum, Xanthan Gum, CalciumChloride, CI 12490 (Pigment Red 5), Mica (CI 77019), Titanium Dioxide (CI 77891) | 1.0 |
| Perfume oil PO1, PO2, PO3, PO4, or PO5 | Fragrance | 0.5 |
| SymGuard CD | Phenylpropanol, o-cymen-5-ol, Decylene glycol | 0.3 |
| 3-Hydroxypropyl caprylate | Propanediol Caprylate | 0.2 |

TABLE 28-continued

Mineral wash and cleaning gel

| Ingredients | INCI | Amount |
|---|---|---|
| 3-Hydroxypropyl undecylenate | Hydroxypropyl undecylenate | 0.1 |

TABLE 29

After Shave Tonic

| Ingredients | INCI | Amount |
|---|---|---|
| SymSol ® PF-3 | Water (Aqua), Pentylene Glycol, Sodium Lauryl Sulfoacetate, Sodium Oleoyl Sarcosinate, Sodium Chloride, Disodium Sulfoacetate, SodiumOleate, Sodium Sulfate | 3.0 |
| SymSitive ® 1609 | Pentylene Glycol, 4-t-Butylcyclohexanol | 1.0 |
| Frescolat ® ML | Menthyl Lactate | 0.3 |
| Glycerol 99.5 P. | Glycerol | 5.0 |
| Water | Water (Aqua) | ad 100 |
| Extrapone ® Glacier Water GW | Glycerol, Water (Aqua) | 1.0 |
| SymCalmin ® | Butylene Glycol, Pentylene Glycol, Hydroxyphenyl Propamidobenzoic Acid | 0.5 |
| Dragosine ® | Carnosine | 0.1 |
| Hydrolite ® 5 | Pentylene Glycol | 5.0 |
| Ethanol 96% | Alcohol Denat. | 5.0 |
| Colour Pigment | Colour Pigment | 0.05 |
| Perfume oil PO1, PO2, PO3, PO4, or PO5 | Fragrance | 0.15 |
| 3-Hydroxypropyl caprylate | Propanediol Caprylate | 0.1 |
| 3-Hydroxypropyl undecylenate | Hydroxypropyl undecylenate | 0.05 |

TABLE 30

Hair conditioner with Crinipan, rinse-off

| Ingredients | INCI | Amount |
|---|---|---|
| Lanette ® O | Cetearyl Alcohol | 4.0 |
| Dragoxat 89 | Ethylhexyl Isononanoate | 2.0 |
| Genamin ® KDM-P | Behentrimonium Chloride | 1.0 |
| SymClariol | Decylene Glycol | 0.1 |
| SF 1550 | Phenyl Trimethicone | 0.1 |
| Neo Heliopan ® BB | Benzophenone-3 | 0.1 |
| Crinipan ® AD | Climbazole | 0.4 |
| Glycerol 99.5 P. | Glycerol | 6.0 |
| Water | Water (Aqua) | ad 100 |
| Actipone ® Alpha Pulp | Water (Aqua), Butylene Glycol, Malic Acid, Actinidia Chinensis (Kiwi) Fruit Juice, Citrus Aurantium Dulcis (Orange) Juice, Citrus Paradisi (Grapefruit) Juice, Pyrus Malus (Apple) Juice, Trideceth-9, Prunus Amygdalus Dulcis (Sweet Almond) Seed Extract | 0.5 |
| Extrapone ® Bamboo P | Propylene Glycol, Water (Aqua), Butylene Glycol, Bambusa Vulgaris Shoot Extract | 0.5 |
| Sodium Hydroxide 10% solution | Sodium Hydroxide | 0.4 |
| Colour I | Colour | 0.6 |
| Colour II | Colour | 0.3 |
| Perfume oil PO1, PO2, PO3, PO4, or PO5 | Fragrance | 0.4 |
| Preservative | Methylparaben | 0.3 |

TABLE 30-continued

Hair conditioner with Crinipan, rinse-off

| Ingredients | INCI | Amount |
|---|---|---|
| 3-Hydroxypropyl caprylate | Propanediol Caprylate | 0.15 |
| Glyceryl monocaprylate | Glyceryl caprylate | 0.15 |
| 3-Hydroxypropyl undecylenate | Hydroxypropyl undecylenate | 0.15 |

TABLE 31

Scalp soothing hair conditioner with UV-B/UV-A protection, rinse off

| Ingredients | INCI | Amount |
|---|---|---|
| 3-Hydroxypropyl caprylate | Propanediol Caprylate | 0.2 |
| Glyceryl monocaprylate | Glyceryl caprylate | 0.2 |
| 3-Hydroxypropyl undecylenate | Hydroxypropyl undecylenate | 0.1 |
| Glyceryl monoundecylenate | Glyceryl undecylenate | 0.1 |
| Abil 350 | Dimethicone | 0.1 |
| Dehyquart A CA | Cetrimonium Chloride | 0.5 |
| Dehyquart SP | Quaternium-52 | 4.0 |
| Dracorin ® CE | Glyceryl Stearate Citrate | 1.0 |
| EDETA BD | Disodium EDTA | 0.1 |
| Extrapone ® Green Tea GW | Glycerin, Water (Aqua), Camellia Sinensis Leaf Extract | 0.7 |
| Perfume oil PO1, PO2, PO3, PO4, or PO5 | Fragrance | 0.5 |
| Lara Care A-200 | Galactoarabinan | 0.5 |
| Neutral Oil | Caprylic/Capric Triglyceride | 1.0 |
| PCL Liquid 100 | Cetearyl Ethylhexoate | 0.3 |
| PCL Solid | Stearyl Heptanoate, Stearyl Caprylate | 3.0 |
| SymOcide ® PS | Phenoxyethanol, Decylene Glycol, 1,2-Hexanediol | 1.0 |
| Water (demineralized) | Water (Aqua) | ad 100 |

TABLE 32

Hair conditioner with UV protection

| Ingredients | INCI | Amount |
|---|---|---|
| Renex PEG 6000 | PEG-150 | 2.5 |
| Hair Conditioner Base | Cetyl alcohol, Behentrimonium chloride, Triticum Vulgare (Wheat) bran extract, Linoleic acid | 3.0 |
| PCL-Solid | Stearyl heptanoate, stearyl caprylate | 0.5 |
| Dow Corning 5200 | Laurylmethicone copolyol | 0.5 |
| Natrosol 250 HR | Hydroxyethylcellulose | 0.5 |
| Benzophenone-4 | Benzophenone-4 | 1.0 |
| Neo Heliopan AP | Disodiumphenyldibenz-imidazole tetrasulphonate | 1.0 |
| Amino methyl propanol | Amino methyl propanol | 2.0 |
| Dow Corning 949 cationic emulsion | Amodimethicone, Cetrimonium chloride, Trideceth-12 | 2.0 |
| Perfume oil PO1, PO2, PO3, PO4, or PO5 | Fragrance | 0.8 |
| 1.2-Hexanediol | 1.2-Hexanediol | 0.5 |
| 3-Hydroxypropyl caprylate | Propanediol Caprylate | 0.2 |
| 3-Hydroxypropyl undecylenate | Hydroxypropyl undecylenate | 0.1 |
| Water | Water (Aqua) | ad 100 |

TABLE 33

Hair conditioner, leave on

| Ingredients | INCI | Amount |
|---|---|---|
| 3-Hydroxypropyl caprylate | Propanediol Caprylate | 0.15 |
| Glyceryl monocaprylate | Glyceryl caprylate | 0.2 |
| 3-Hydroxypropyl undecylenate | Hydroxypropyl undecylenate | 0.1 |
| Glyceryl monoundecylenate | Glyceryl undecylenate | 0.05 |
| Dehyquart A CA | Cetrimonium Chloride | 0.2 |
| Dehyquart SP | Quaternium-52 | 2.0 |
| Dracorin ® CE | Glyceryl Stearate Citrate | 1.0 |
| Drago-Calm | Water, Glycerin, Avena Sativa (Oat) Kernel Extract | 2.0 |
| Farnesol | Farnesol | |
| Perfume oil PO1, PO2, PO3, PO4, or PO5 | Fragrance | 0.5 |
| Lara Care A-200 | Galactoarabinan | 0.1 |
| Polymer JR 400 | Polyquaternium-10 | 0.1 |
| Propylene Glycol | Propylene Glycol | 0.8 |
| SymMollient ® WS | Trideceth-9. PEG-5 Isononanoate. Water | 1.0 |
| SymSol ®PF3 | Water, Pentylene Glycol, Sodium Lauryl Sulfoacetate, Sodium Oleoyl Sarcosinate, Sodium Chloride, Disodium Sulfoacetate, Sodium Oleate, Sodium Sulfate | 1.5 |
| SymTriol ® | Caprylyl Glycol, 1.2-Hexanediol, Methylbenzyl Alcohol | 1.0 |
| Water (demineralized) | Water (Aqua) | ad 100 |

TABLE 34

Anti-itch hair conditioner, leave on

| Ingredients | INCI | Amount |
|---|---|---|
| 3-Hydroxypropyl caprylate | Propanediol Caprylate | 0.15 |
| Glyceryl monocaprylate | Glyceryl caprylate | 0.15 |
| 3-Hydroxypropyl undecylenate | Hydroxypropyl undecylenate | 0.1 |
| (-)-alpha Bisabolol | Bisabolol | 0.1 |
| Dehyquart A CA | Cetrimonium Chloride | 0.5 |
| Dehyquart SP | Quaternium-52 | 4.0 |
| Dracorin ® CE* | Glyceryl Stearate Citrate | 1.0 |
| Drago-Oat-Active | Water (Aqua), Butylene Glycol, Avena Sativa (Oat) Kernel Extract | 2.0 |
| Perfume oil PO1, PO2, PO3, PO4, or PO5 | Fragrance | 0.1 |
| Lara Care A-200 | Galactoarabinan | 1.5 |
| Neutral Oil | Caprylic/Capric Triglyceride | 1.0 |
| PCL Liquid 100 | Cetearyl Ethylhexoate | 0.3 |
| Polymer JR 400 | Polyquaternium-10 | 0.1 |
| Propylene Glycol | Propylene Glycol | 0.8 |
| SymGlucan ® | Aqua, Glycerin, 1,2-Hexandiol, Caprylyl Glycol, Beta-Glucan | 5 |
| SymMollient ® W/S | Trideceth-9, PEG-5 Isononanoate, Water (Aqua) | 2.0 |
| SymOcide ® PH | Phenoxyethanol, Hydroxyacetophenone, Caprylyl Glycol, Aqua | 1.2 |
| SymSol ®PF3 | Water, Pentylene Glycol, Sodium Lauryl Sulfoacetate, Sodium Oleoyl Sarcosinate, Sodium Chloride, Disodium Sulfoacetate, Sodium Oleate, Sodium Sulfate | 1.5 |
| Water, demineralized | Water (Aqua) | ad 100 |

TABLE 35

Sprayable hair conditioner with zinc pyrithrione, leave-on

| Ingredients | INCI | Amount |
|---|---|---|
| Monomuls 60-35 C | Hydrogenated Palm Glycerides | 1.7 |
| Cetiol OE | Dicaprylyl Ether | 7.2 |
| Abil 100 | Dimethicone | 3.6 |
| Dehyquart F 75 | Distearoylethyl Hydroxyethylmonium Methosulfate, Cetearyl Alcohol | 4.0 |
| Eumulgin B1 | Ceteareth-12 | 3.5 |
| Cetiol S | Diethylhexylcyclohexane | 7.2 |
| D-Panthenol | Panthenol | 0.1 |
| Glycerol 99.5 P. | Glycerol | 1.5 |
| Water | Water (Aqua) | ad 100 |
| Actipone ® Rosemary | Water (Aqua), PropyleneGlycol, Rosmarinus Officinalis (Rosemary) Leaf Extract | 0.1 |
| Frescolat ® ML Cryst. | Menthyl Lactate | 0.5 |
| Dragosantol100 | Bisabolol | 0.1 |
| Zinc Omadine | Zinc pyrithione | 0.1 |
| Perfume oil PO1, PO2, PO3, PO4, or PO5 | Fragrance | 0.4 |
| 2-Phenoxyethyl alcohol | Phenoxyethanol | 0.4 |
| SymSave H | Hydroxyacetophenone | 0.3 |
| SymDiol 68 | 1,2-Hexanediol, Caprylyl glycol | 0.3 |
| 3-Hydroxypropyl caprylate | Propanediol Caprylate | 0.4 |
| 3-Hydroxypropyl undecylenate | Hydroxypropyl undecylenate | 0.1 |

TABLE 36

Hair styling gel

| Ingredients | Amount |
|---|---|
| Water | ad 100 |
| PVM/MA Decadiene Crosspolymer | 0.6 |
| PVP | 3.0 |
| Isocetyl Stearate | 4.0 |
| Ethylhexyl Methoxycinnamate | 0.5 |
| Hydrolite-5 Green (Pentylene Glycol) | 0.5 |
| Aminomethyl Propanol | 0.4 |
| Perfume oil PO1, PO2, PO3, PO4, or PO5 | 0.6 |
| SymDiol ® 68T (1,2-Hexanediol, 1,2-Octanediol, Tropolone) | 0.4 |
| Phenoxyethanol | 0.3 |
| 3-Hydroxypropyl caprylate | 0.2 |
| 3-Hydroxypropyl undecylenate | 0.1 |

TABLE 37

Deodorant stick

| Ingredients | Amount |
|---|---|
| Sodium stearate | 8.0 |
| PPG-3 Myristyl ether | 70.0 |
| 1.2-propylene glycol | 10.0 |
| 1.1-dimethyl-3-phenylpropanol | 0.2 |
| 2-butyloctanoic acid | 0.2 |
| Perfume oil PO1, PO2, PO3, PO4, or PO5 | 0.6 |
| Water | ad 100 |
| SymDeo Plus (Jasmol (2-benzlheptanol), 1-Dodecanol (Lauryl Alcohol), 1,2-Decanediol (Decylene Glycol), 2-Phenoxyethyl Alcohol (Phenoxyethanol)) | 0.5 |
| 3-Hydroxypropyl caprylate | 0.15 |
| Glyceryl monocaprylate | 0.15 |
| 3-Hydroxypropyl undecylenate | 0.1 |

TABLE 38

Zirconium suspensoid antiperspirant stick

| Ingredients | INCI | Amount |
|---|---|---|
| PCL Liquid 100 | Cetearyl ethylhexanonate | ad 100 |
| Silicone Fluid 345 | Cyclomethicone | 10.0 |
| CRODACOL C90 | Cetyl Alcohol | 8.0 |
| SYNCROWAX HGLC | C18-36 Triglyceride | 8.0 |
| CRODAMOL PTC | Pentaerythritol Tetracaprylate/Caprate | 5.0 |
| SymDeo MPP | Dimethyl Phenylbutanol | 0.3 |
| SYNCROWAX HRC | Tribehenin | 4.0 |
| VOLPO N5 | Oleth-5 | 1.0 |
| Titanium Dioxide | | 1.0 |
| Rezal 36GP | Aluminium Tetrachlorohydrex GLY | 20.0 |
| Dry Flo C | Aluminium Starch Octenyl Succinate | 22.5 |
| Preservative | Phenoxyethanol | 0.8 |
| Perfume oil PO1, PO2, PO3, PO4, or PO5 | Fragrance | 0.6 |
| 3-Hydroxypropyl caprylate | Propanediol Caprylate | 0.15 |
| Glyceryl monocaprylate | Glyceryl caprylate | 0.15 |
| 3-Hydroxypropyl undecylenate | Hydroxypropyl undecylenate | 0.1 |
| Glyceryl monoundecylenate | Glyceryl undecylenate | 0.1 |

TABLE 39

Antiperspirant/deodorant roll-on

| Ingredients | INCI | Amount |
|---|---|---|
| 3-Hydroxypropyl caprylate | Propanediol Caprylate | 0.15 |
| Glyceryl monocaprylate | Glyceryl caprylate | 0.15 |
| 3-Hydroxypropyl undecylenate | Hydroxypropyl undecylenate | 0.1 |
| Dragosantol ® 100 | Bisabolol | 0.1 |
| Ethanol 96% | Ethanol | 30.0 |
| Farnesol | Farnesol | 0.5 |
| Perfume oil PO1, PO2, PO3, PO4, or PO5 | Fragrance | 1.5 |
| Frescolat ®ML cryst, | Menthyl Lactate | 0.2 |
| Irgasan DP 300 | Triclosan | 0.3 |
| Natrosol 250 HHR | Hydroxyethyl-cellulose | 0.3 |
| Solubilizer 611674 | PEG-40 Hydrogenated Castor Oil, Trideceth-9, Water (Aqua) | 2.0 |
| SymDeo ® B125 | 2-Methyl 5-Cyclohexylpentanol | 0.5 |
| Water (demineralized) | Water (Aqua) | ad 100 |
| Zirkonal L 450 | Aluminium Zirconium Pentachlorohydrate (40% aqueous solution) | 37.0 |

TABLE 40

Deodorant formulation in the form of a roll-on gel

| Ingredients | Amount |
|---|---|
| 1.3-butylene glycol | 2.0 |
| 2-Methyl 5-cyclohexylpentanol | 0.1 |
| PEG-40-hydrogenated castor oil | 2.0 |
| Hydroxyethylcellulose | 0.5 |
| Pentylene Glycol | 1.0 |
| Perfume oil PO1, PO2, PO3, PO4, or PO5 | 0.3 |
| 1,3-propanediol | 0.5 |
| SymGuard CD (3-Phenylpropanol, o-cymen-3-ol, Decylene glycol) | 0.4 |
| Ethylhexyl glycerin | 0.1 |
| 3-Hydroxypropyl caprylate | 0.3 |
| Glyceryl monocaprylate | 0.15 |
| 3-Hydroxypropyl undecylenate | 0.1 |
| Water | ad 100 |

TABLE 41

Clear deo anti-perspirant roll-on

| Ingredients | INCI | Amount |
|---|---|---|
| Methocel E4M Premium | Hydroxypropyl Methylcellulose | 0.5 |
| Water | Water (Aqua) | ad 100 |
| Neo-PCL Water Soluble N | Trideceth-9, PEG-5 Ethylhexanoate, Water (Aqua) | 1.0 |
| Solubilizer | PEG-40 Hydrogenated Castor Oil, Trideceth-9, Propylene Glycol, Water (Aqua) | 3.0 |
| Deolite | Dimethyl Phenylpropanol, Pentylene Glycol | 0.5 |
| Locron LW | Aluminium Chlorohydrate | 25.0 |
| Aloe Vera Gel Concentrate 10/1 | Aloe Barbadensis Leaf Juice | 1.0 |
| 1.2-Propylene Glycol 99 P GC | Propylene Glycol | 4.0 |
| Ethanol 96% | Alcohol Denat. | 30.0 |
| Perfume oil PO1, PO2, PO3, PO4, or PO5 | Fragrance | 1.0 |
| 3-Hydroxypropyl caprylate | Propanediol Caprylate | 0.3 |
| 3-Hydroxypropyl undecylenate | Hydroxypropyl undecylenate | 0.15 |

TABLE 42

Deodorant pump spray with SymClariol

| Ingredients | INCI | Amount |
|---|---|---|
| SymClariol ® | Decylene Glycol | 0.2 |
| Solubilizer | PEG-40 Hydrogenated Castor Oil, Trideceth-9, Propylene Glycol, Water (Aqua) | 4.0 |
| Neo-PCL Water Soluble N | Trideceth-9, PEG-5 Ethylhexanoate, Aqua | 1.5 |
| SymRelief ® | Bisabolol, Zingiber Officinale (Ginger) Root Extract | 0.1 |
| Water | Water (Aqua) | ad 100 |
| 1,2-Propylene Glycol | Propylene Glycol | 6.0 |
| Perfume oil PO1, PO2, PO3, PO4, or PO5 | Perfume | 0.4 |
| SymDiol ® 68 | 1,2-Hexanediol, Caprylyl Glycol | 0.2 |
| 3-Hydroxypropyl caprylate | Propanediol Caprylate | 0.2 |
| 3-Hydroxypropyl undecylenate | Hydroxypropyl undecylenate | 0.1 |

TABLE 43

Whitening deodorant spray

| Ingredients | Amount |
|---|---|
| PEG-40-hydrogenated castor oil | 3.0 |
| Ethylhexylglycerol (Octoxyglycerol) | 0.2 |
| Symbright 2036 (Sclareolide) | 0.1 |
| Ethanol | 40.0 |
| Citrate buffer | 0.5 |
| 1.2-Hexanediol, 1.2-Octanediol (SymDiol 68) | 0.3 |
| SymOcide C (o-cymen-5-ol) | 0.05 |
| 2-Benzylheptan-1-ol (Jasmol) | 0.1 |
| Perfume oil PO1, PO2, PO3, PO4, or PO5 | 0.75 |
| Phenoxyethanol | 0.4 |
| 3-Hydroxypropyl caprylate | 0.2 |
| Glyceryl monoundecylenate | 0.1 |
| Water | ad 100 |

TABLE 44

Deodorant Aerosol Spray

| Ingredients | Amount |
|---|---|
| Perfume oil PO1, PO2, PO3, PO4, or PO5 | 0.75 |
| 3-Hydroxypropyl caprylate | 0.2 |
| Disiloxane | Ad 100 |
| Isoadipate | 5.0 |
| C12-C15 Alkyl Benzoate | 10.0 |
| Tocopheryl Acetate | 0.5 |
| Farnesol | 0.3 |

40% bulk, charged with 60% Propane/Butane

TABLE 45

Sunscreen lotion (o/w, broadband protection)

| Ingredients | INCI | Amount |
|---|---|---|
| 3-Hydroxypropyl caprylate | Propanediol Caprylate | 0.15 |
| Glyceryl monocaprylate | Glyceryl caprylate | 0.15 |
| 3-Hydroxypropyl undecylenate | Hydroxypropyl undecylenate | 0.1 |
| Glyceryl monoundecylenate | Glyceryl undecylenate | 0.1 |
| Carbopol Ultrez-10 | Carbomer | 0.2 |
| Dow Corning 246 Fluid | Cyclohexasiloxane and Cyclopentasiloxane | 2.0 |
| Dragosantol ® 100* | Bisabolol | 0.3 |
| EDETA BD | Disodium EDTA | 0.1 |
| Emulsiphos ® | Potassium Cetyl Phosphate, Hydrogenated Palm Glycerides | 1.5 |
| Perfume oil PO1, PO2, PO3, PO4, or PO5 | Fragrance | 0.4 |
| Frescolat ®MGA | Menthone Glycerol Acetal | 0.3 |
| Glycerol 85% | Glycerin | 4.7 |
| Keltrol RD | Xanthan Gum | 0.2 |
| Lanette O | Cetearyl Alcohol | 1.0 |
| Neo Heliopan ® 357 | Butyl Methoxy-dibenzoyl-methane | 1.0 |
| Neo Heliopan ® AP (10% as sodium salt) | Disodium Phenyl Dibenzimidazole Tetrasulfonate | 10.0 |
| Neo Heliopan ® AV | Ethylhexyl Methoxy-cinnamate | 3.0 |
| Neo Heliopan ® Hydro (15% as sodium salt) | Phenylbenz-imidazole Sulfonic Acid | 6.7 |
| Neo Heliopan ® MBC | 4-Methylbenzyl-idene Camphor | 1.5 |
| Neo Heliopan ® OS | Ethylhexyl Salicylate | 5.0 |
| Neutral Oil | Caprylic/Capric Triglyceride | 2.0 |
| SymMatrix ® | Maltodextrin, Rubus Fruticosus (Blackberry) Leaf Extract | 0.3 |
| SymOcide ® BHO | Hydroxyacetophenone, Benzyl alcohol, Caprylyl glycol, Aqua | 1.5 |
| Tegosoft TN | C12-15 Alkyl Benzoate | 5.0 |
| Tocopherol Acetate | Tocopheryl Acetate | 0.5 |
| Triethanolamine, 99% | Triethanolamine | 0.5 |
| Water (demineralized) | Water (Aqua) | ad 100 |

TABLE 46

Emulsion with UV-A/B-broadband protection

| Ingredients | INCI | Amount |
|---|---|---|
| 3-Hydroxypropyl caprylate | Propanediol Caprylate | 0.1 |
| Glyceryl monocaprylate | Glyceryl caprylate | 0.1 |
| 3-Hydroxypropyl undecylenate | Hydroxypropyl undecylenate | 0.05 |
| Glyceryl monoundecylenate | Glyceryl undecylenate | 0.05 |
| Abil 350 | Dimethicone | 0.3 |
| Butylene Glycol | Butylene Glycol | 3.0 |
| Carbopol Ultrez-10 | Carbomer | 0.2 |
| Citric Acid 10% sol. | Citric Acid | 0.3 |
| Dragosantol ® 100* | Bisabolol | 0.1 |
| EDETA BD | Disodium EDTA | 0.1 |
| Emulsiphos ® | Potassium Cetyl Phosphate, Hydrogenated Palm Glycerides | 1.5 |
| Perfume oil PO1, PO2, PO3, PO4, or PO5 | Fragrance | 0.1 |
| Frescolat ®X-COOL | Menthyl Ethylamido Oxalate | 1.0 |
| Glyceryl Stearate | Glyceryl Stearate | 2.0 |
| Keltrol RD | Xanthan Gum | 0.2 |
| Lanette 16 | Cetyl Alcohol | 1.2 |
| Lanette E | Sodium Cetearyl Sulfate | 0.7 |
| Neo Heliopan ® AP (10% as sodium salt) | Disodium Phenyl Dibenzimidazole Tetrasulfonate | 22.0 |
| Neo Heliopan ® HMS | Homosalate | 5.0 |
| Neutral Oil | Caprylic/Capric Triglyceride | 2.0 |
| PCL Liquid 100 | Cetearyl Ethylhexoate | 3.0 |
| Sodium Hydroxide (10% sol.) | Sodium Hydroxide | 2.8 |
| Symdiol ®68 | 1,2-Hexanediol, Caprylylglycol | 0.5 |
| SymMollient ®S | Cetearyl Nonanoate | 1.5 |
| SymSitive ® 1609 | Pentylene Glycol, 4-t-Butylcyclohexanol | 0.5 |
| SymWhite ®377 | Phenylethyl Resorcinol | 0.5 |
| Tocopherol Acetate | Tocopheryl Acetate | 0.5 |
| Water (demineralized) | Water (Aqua) | ad 100 |

TABLE 47

Sun protection soft cream (w/o). SPF 40

| Ingredients | INCI | Amount |
|---|---|---|
| Dehymuls PGPH | Polyglyceryl-2 dipolyhydroxystearate | 5.0 |
| Copherol 1250 | Tocopheryl acetate | 0.5 |
| Permulgin 3220 | Ozocerite | 0.5 |
| Zinc stearate | Zinc stearate | 0.5 |
| Tegosoft TN | C12-15 Alkyl benzoate | 10.0 |
| Neo Heliopan ® E1000 | Isoamyl-p-methoxycinnamate | 2.0 |
| Neo Heliopan ® 303 | Octocrylene | 5.0 |
| Neo Heliopan ® MBC | 4-Methylbenzylidene camphor | 3.0 |
| Zinc oxide. neutral | Zinc oxide | 5.0 |
| Water, distilled | Water (aqua) | ad 100 |
| EDETA BD | Disodium EDTA | 0.1 |
| Glycerol | Glycerol | 4.0 |
| Magnesium sulfate | Magnesium sulfate | 0.5 |
| Perfume oil PO1, PO2, PO3, PO4, or PO5 | Fragrance | 0.3 |
| Symdiol ® 68 | 1,2-Hexanediol, Caprylylglycol | 0.3 |
| 3-Hydroxypropyl caprylate | Propanediol Caprylate | 0.15 |
| Glyceryl monocaprylate | Glyceryl caprylate | 0.15 |

TABLE 48

Sun protection milk (w/o)

| Ingredients | INCI | Amount |
|---|---|---|
| Dehymuls PGPH | Polyglyceryl-2 dipolyhydroxystearate | 3.0 |
| Beeswax 8100 | Beeswax | 1.0 |
| Monomuls 90-0-18 | Glyceryl oleate | 1.0 |
| Zinc stearate | Zinc stearate | 1.0 |
| Hydrolite-8 | Caprylyl Glycol | 0.3 |
| Cetiol SN | Cetearyl isononanoate | 5.0 |
| Cetiol OE | Dicaprylyl ether | 5.0 |
| Tegosoft TN | C12-15 alkyl benzoate | 4.0 |
| Vitamin E | Tocopherol | 0.5 |
| Neo Heliopan ® OS | Ethylhexyl salicylate | 5.0 |
| Neo Heliopan ® AV | Ethylhexyl methoxycinnamate | 7.5 |
| Uvinul T150 | Ethylhexyl triazone | 1.5 |
| Water. distilled | Water (Aqua) | ad 100 |
| Trilon BD | Disodium EDTA | 0.1 |
| Glycerol | Glycerol | 5.0 |
| Neo Heliopan ® AP 10% solution. neutralized with NaOH | Disodium phenyl dibenzimidazole tetrasulfonate | 15.0 |

TABLE 48-continued

Sun protection milk (w/o)

| Ingredients | INCI | Amount |
|---|---|---|
| Perfume oil PO1, PO2, PO3, PO4, or PO5 | Fragrance | 0.25 |
| Alpha bisabolol | Bisabolol | 0.1 |
| SymOcide ® PT | Phenoxyethanol. Tropolone | 0.25 |
| 3-Hydroxypropyl caprylate | Propanediol Caprylate | 0.2 |
| 3-Hydroxypropyl undecylenate | Hydroxypropyl undecylenate | 0.1 |

TABLE 49

Sun spray with UV-A/B-broadband protection with low oil content

| Ingredients | INCI | Amount |
|---|---|---|
| 3-Hydroxypropyl caprylate | Propanediol Caprylate | 0.15 |
| Glyceryl monocaprylate | Glyceryl caprylate | 0.15 |
| 3-Hydroxypropyl undecylenate | Hydroxypropyl undecylenate | 0.05 |
| Glyceryl monoundecylenate | Glyceryl undecylenate | 0.05 |
| Ethanol 96% | Ethanol | 13.0 |
| Perfume oil PO1, PO2, PO3, PO4, or PO5 | Fragrance | 0.5 |
| Glyceryl Stearate | Glyceryl Stearate | 4.0 |
| Hydroviton ® PLUS | Water, Pentylene Glycol, Glycerin, Fructose, Urea, Citric Acid, Sodium Hydroxide, Maltose, Sodium PCA, Sodium Chloride, Sodium Lactate, Trehalose, Allantoin, Sodium hyaluronate, Glucose | 1.0 |
| Isoadipate ® | Diisopropyl Adipate | 1.0 |
| Neo Heliopan ® AV | Ethylhexyl Methoxy-cinnamate | 25.0 |
| Neo Heliopan ® MBC | 4-Methylbenzyl-idene Camphor | 33.3 |
| Propylene Glycol | Propylene Glycol | 0.8 |
| Tego Betain L7 | Cocamidopropyl Betaine | 1.0 |
| Water (demineralized) | Water (Aqua) | ad 100 |

TABLE 50

Sunscreen spray o/w, SPF 15-20

| Ingredients | INCI | Amount |
|---|---|---|
| Dracorin ® GOC | Glyceryl Oleate Citrate, Caprylic/Capric Triglyceride | 2.0 |
| Corapan ® TQ | Diethylhexyl 2,6-Naphthalate | 3.0 |
| Neo Heliopan ® HMS | Homosalate | 7.0 |
| Neo Heliopan ® OS | Ethylhexyl Salicylate | 5.0 |
| Neo Heliopan ® 357 | Butyl Methoxydibenzoylmethane | 3.0 |
| Isoadipate | Diisopropyl Adipate | 6.0 |
| Baysilone ® Oil M10 | Dimethicone | 1.0 |
| Edeta ® BD | Disodium EDTA | 0.1 |
| Vitamin E Acetate | Tocopheryl Acetate | 0.5 |
| Dragosantol ® 100 | Bisabolol | 0.1 |
| Pemulen ® TR-2 | Acrylates/C10-30 Alkyl Acrylate Crosspolymer | 0.25 |
| Water | Water (Aqua) | ad 100 |
| Glycerol 99, 5 P, | Glycerol | 4.0 |
| Butylene Glycol | Butylene Glycol | 5.0 |
| Neo Heliopan ® Hydro (103089), used as 25% aq, solution neutralized with Biotive ® L-Arginine | Phenylbenzimidazole Sulfonic Acid | 8.0 |
| Biotive ® L-Arginine | Arginine | 0.55 |
| Perfume oil PO1, PO2, PO3, PO4, or PO5 | Fragrance | 0.4 |
| SymOcide PS | Phenoxyethanol, 1,2-Hexanediol, Decylene glycol | 0.8 |
| 3-Hydroxypropyl caprylate | Propanediol Caprylate | 0.2 |
| 3-Hydroxypropyl undecylenate | Hydroxypropyl undecylenate | 0.1 |

TABLE 51

After sun gel

| Ingredients | INCI | Amount |
|---|---|---|
| SymSol ® PF-3 | Water (Aqua), Pentylene Glycol, Sodium Lauryl Sulfoacetate, Sodium Oleoyl Sarcosinate, Sodium Chloride, Disodium Sulfoacetate, Sodium Oleate, Sodium Sulfate | 3.0 |
| Glycerol 99, 5 P, | Glycerol | 5.0 |
| SymHelios ® 1031 | Benzylidene Dimethoxydimethylin danone | 0.1 |
| Water | Water (Aqua) | ad 100 |
| Pemulen ® TR-2 | Acrylates/C10-30 Alkyl Acrylate Crosspolymer | 1.0 |
| D-Panthenol 75 W | Panthenol | 0.5 |
| SymFinity ® 1298 | Echinacea Purpurea Extract | 0.1 |
| Extrapone ® Pearl GW | Water (Aqua), Glycerol, Hydrolyzed Pearl, Xanthan Gum | 1.0 |
| Sodium Hydroxide 10% solution | Sodium Hydroxide | 2.5 |
| Ethanol 96% | Alcohol Denat, | 15.0 |
| Perfume oil PO1, PO2, PO3, PO4, or PO5 | Fragrance | 0.2 |
| SymOcide ® PS | Phenoxyethanol, 1,2-Hexanediol, Decyleneglycol | 0.8 |
| 3-Hydroxypropyl caprylate | Propanediol Caprylate | 0.15 |
| 3-Hydroxypropyl undecylenate | Hydroxypropyl undecylenate | 0.05 |

TABLE 52

After sun lotion

| Ingredients | Amount |
|---|---|
| Acrylate/C10-30 alkylacrylate crosspolymer | 0.4 |
| Cetearylethyl hexanoate | 15.0 |
| Bisabolol | 0.2 |
| Tocopheryl acetate | 1.0 |
| Panthenol | 1.0 |
| Alcohol | 15.0 |
| Glycerol | 3.0 |
| Perfume oil PO1, PO2, PO3, PO4, or PO5 | 0.30 |
| 1.2-Hexanediol (Hydrolite-6) | 1.0 |
| 4-Hydroxyacetophenone (SymSave H) | 0.3 |
| Pentylene glycol (Hydrolite-5 Green) | 4.0 |
| Aqua dem. | ad 100 |
| Triethanolamine | 0.2 |
| 3-Hydroxypropyl caprylate | 0.2 |
| 3-Hydroxypropyl undecylenate | 0.1 |

TABLE 53

Syndet antimicrobial soap bar

| Ingredients | INCI | Amount |
|---|---|---|
| Zetesap 813 A | Disodium Lauryl Sulfosuccinate, Sodium Lauryl Sulfate, Corn Starch, Cetearyl Alcohol, Paraffin, Titanium Dioxide | ad 100 |
| Amphotensid GB 2009 | Disodium Cocoamphodiacetate | 6.0 |
| Allantoin | Allantoin | 1.0 |
| Perfume oil PO1, PO2, PO3, PO4, or PO5 | Fragrance | 1.0 |
| SymOcide C | o-cymen-5-ol | 0.1 |
| 3-Hydroxypropyl caprylate | Propanediol Caprylate | 0.1 |
| Glyceryl monocaprylate | Glyceryl caprylate | 0.1 |
| 3-Hydroxypropyl undecylenate | Hydroxypropyl undecylenate | 0.05 |

TABLE 53-continued

Syndet antimicrobial soap bar

| Ingredients | INCI | Amount |
|---|---|---|
| Glyceryl monoundecylenate | Glyceryl undecylenate | 0.05 |

TABLE 54

Syndet soap bar

| Ingredients | INCI | Amount |
|---|---|---|
| Fenopon AC-78 | Sodium Cocoyl Isethionate | 20.0 |
| Natriumlauryl-sulfoacetate | Sodium Lauryl Sulfoacetate | 16.0 |
| Paraffin | Paraffin | 19.0 |
| Wax. microcrystalline | Microcrystalline Wax | 1.0 |
| Corn Starch | Corn Starch | 8.0 |
| Coconut acid | Coconut acid | 2.0 |
| Lauric acid diethanol amide | Lauramide DEA | 2.0 |
| Dextrin | Dextrin | 21.0 |
| Lactic acid, 88% | Lactic Acid | 1.0 |
| SymGuard CD | 3-Phenylpropanol, o-cymen-5-ol, Decylene glycol | 0.3 |
| Thymol | Thymol | 0.05 |
| Water | Water | ad 100 |
| Perfume oil PO1, PO2, PO3, PO4, or PO5 | Fragrance | 1.0 |
| 3-Hydroxypropyl caprylate | Propanediol Caprylate | 0.15 |
| Glyceryl monocaprylate | Glyceryl caprylate | 0.15 |
| 3-Hydroxypropyl undecylenate | Hydroxypropyl undecylenate | 0.05 |
| Glyceryl monoundecylenate | Glyceryl undecylenate | 0.05 |

TABLE 55

Antimicrobial toilet soap bar

| Ingredients | Amount |
|---|---|
| Sodium soap from tallow | 60.0 |
| Sodium soap from palm oil | 27.0 |
| Pentylene Glycol | 0.5 |
| Glycerol | 2.0 |
| Sodium Chloride | 0.5 |
| 1-Hydroxyethane-1,1-diphosphonic acid, tetrasodium salt | 0.3 |
| Alpha-Tocopherol | 0.1 |
| Pigment Yellow 1 | 0.02 |
| Water | ad 100 |
| Perfume oil PO1, PO2, PO3, PO4, or PO5 | 3.0 |
| Farnesol | 0.2 |
| 3-Hydroxypropyl caprylate | 0.1 |
| Glyceryl nnonocaprylate | 0.1 |
| 3-Hydroxypropyl undecylenate | 0.05 |
| Glyceryl nnonoundecylenate | 0.05 |

TABLE 56

Shaving foam

| Ingredients | Amount |
|---|---|
| Dem. Water | ad 100 |
| Triethanolamine | 4.0 |
| Edenor L2 SM (Stearinic acid, Palmitinic acid) (Cognis) | 5.3 |

TABLE 56-continued

Shaving foam

| Ingredients | Amount |
|---|---|
| Laureth-23 | 3.0 |
| Stearylalcohol | 0.5 |
| SymOcide BHO (Hydroxacetophenone, Benzyl alcohol, Caprylyl glycol, Water) | 1.0 |
| 3-Hydroxypropyl caprylate | 0.2 |
| Glyceryl monocaprylate | 0.1 |
| 3-Hydroxypropyl undecylenate | 0.1 |
| Glyceryl monoundecylenate | 0.05 |
| Sodium lauryl sulfate | 3.0 |
| Extrapone Seaweed (Water, Propylene glycol, Potassium iodide, Fucus Vesiculosus Extract) | 1.0 |
| Dragosantol (Bisabolol, Farnesol) | 0.1 |
| Perfume oil PO1, PO2, PO3, PO4, or PO5 | 1.0 |
| Propane, butane 4,2 Bar | 4.0 |

TABLE 57

Sprayable disinfecting gel

| Ingredients | INCI | Amount |
|---|---|---|
| Water | Water (Aqua) | ad 100 |
| Stabileze QM | PVM/Ma Decadiene Crosspolymer | 0.25 |
| Sodium Hydroxide 10% solution | Sodium Hydroxide | 0.4 |
| Coffein pure | Caffeine | 0.5 |
| Extrapone ® Horse Chestnut | Propylene Glycol, Water (Aqua), Glucose, Aesculus Hippocastanum (Horse Chestnut) Seed Extract, Lactic Acid | 1.0 |
| Hydrolite ® 5 | Pentylene Glycol | 3.0 |
| Xylityl Sesquicaprylate | Xylityl Sesquicaprylate | |
| 1,3 Butylene Glycol | Butylene Glycol | 5.0 |
| Biotive ® Esculin Sesquihydrate | Esculin | 0.3 |
| Ethanol 96% | Alcohol Denat. | 10.0 |
| Solubilizer | PEG-40 Hydrogenated Castor Oil, Trideceth-9, Water (Aqua) | 0.5 |
| Perfume oil PO1, PO2, PO3, PO4, or PO5 | Fragrance | 0.2 |
| Octenidine dihydrochloride | Octenidine dihydrochloride | 0.1 |
| Preservative | Phenoxyethanol | 0.7 |
| 3-Hydroxypropyl caprylate | Propanediol Caprylate | 0.15 |
| Glyceryl monocaprylate | Glyceryl caprylate | 0.15 |
| 3-Hydroxypropyl undecylenate | Hydroxypropyl undecylenate | 0.05 |
| Glyceryl monoundecylenate | Glyceryl undecylenate | 0.05 |

TABLE 58

Solution for wet wipes

| Ingredients | INCI | Amount |
|---|---|---|
| SymSol ® PF-3 | Water (Aqua), Pentylene Glycol, Sodium Lauryl Sulfoacetate, SodiumOleoyl Sarcosinate, Sodium Chloride, Disodium Sulfoacetate, SodiumOleate, Sodium Sulfate | 2.0 |

TABLE 58-continued

Solution for wet wipes

| Ingredients | INCI | Amount |
|---|---|---|
| Dragosantol ® 100 | Bisabolol | 0.1 |
| Glycerol 99.5 P, | Glycerol | 5.0 |
| Water | Water (Aqua) | ad 100 |
| Hydrolite ® 5 | Pentylene Glycol | 5.0 |
| D-Panthenol 75 W | Panthenol | 0.8 |
| DragoCalm ® | Water (Aqua), Glycerol, Avena Sativa (Oat) Kernel Extract | 1.0 |
| Witch Hazel-Distillate | Hamamelis Virginiana (Witch Hazel) Water, Water (Aqua), Alcohol | 1.0 |
| Allplant Essence ® Org. Rose Geranium P | Pelargonium Graveolens Flower/Leaf/Stem Water | 1,0 |
| Perfume oil PO1, PO2, PO3, PO4, or PO5 | Fragrance | 0.1 |
| SymOcide BHO | Benzyl alcohol, Hydroxyacetophenone, Caprylyl glycol, Water | 0.8 |
| 3-Hydroxypropyl caprylate | Propanediol Caprylate | 0.2 |
| Glyceryl monocaprylate | Glyceryl caprylate | 0.2 |
| 3-Hydroxypropyl undecylenate | Hydroxypropyl undecylenate | 0.1 |
| Glyceryl monoundecylenate | Glyceryl undecylenate | 0.1 |

TABLE 59

(in w/w %) Further preferred cleansing formulations without sodium lauryl ether sulfate (SLES).
1: Mild Hair & Body Wash; 2: Shampoo; 3: Anti Acne Face Wash; 4: Color Care Shampoo; 5: Feminine Wash; 6: Micellar Water; 7: Liquid soap; 8: Antidandruff Shampoo; 9: Baby Shampoo; 10: Solid shampoo.

| INCI | 1 | 2 | 3 | 4 | 5 | 6 | 7 | 8 | 9 | 10 |
|---|---|---|---|---|---|---|---|---|---|---|
| 3-Hydroxypropyl caprylate (Propanediol Caprylate) | 0,5 | 1,0 | 0,3 | 0,1 | 0,2 | 0,5 | 0,5 | 0,5 | 0,5 | — |
| 3-Hydroxypropyl undecylenate | — | — | 0,1 | — | — | — | — | — | 0,05 | — |
| Glyceryl mnonoundecylenate | — | — | — | 0,1 | — | — | — | — | — | — |
| 1,2 Hexanediol, Caprylyl Glycol (Synndiol 68) | 0,5 | 0,5 | — | — | 1,0 | 0,5 | — | 0,5 | 0,5 | — |
| 1,2 Hexanediol, Caprylyl Glycol, Tropolone (Synndiol 68 T) | — | — | 0,7 | — | — | 0,7 | — | — | — | — |
| Ammonium Lauryl Sulfate (Stepanol AM) | — | 5,0 | — | — | — | — | — | — | — | — |
| Aqua, Glycerin, Echinacea Purpurea Extract (Extrapone Echinacea) | — | — | — | — | — | 0,3 | — | — | — | — |
| Aqua, Pentylene Glycol, Sodium Lauryl Sulfoacetate, Sodium Oleoyl Sarcosinate, Sodium Chloride, Sodium Oleate (SynnSol PF3) | — | — | — | — | — | 3,0 | — | — | — | — |
| Bisabolol (Dragosantol 100) | — | — | — | — | 0,1 | — | — | — | — | — |
| Butyrospermum Parkii Butter (Cetiol SB 45) | — | — | — | — | — | — | — | — | — | 13,0 |
| Caprylic/Capric Triglyceride | — | — | — | — | — | — | — | — | — | 2,0 |
| Hydroxynnethoxyphenyl Decanone (Synndecanox HA) | — | — | — | — | — | — | — | — | — | — |
| Caprylyl Glycol, 1,2 Hexanediol, Methylbenzyl Alcohol | — | — | — | — | — | 0,8 | — | — | 0,8 | — |
| Citric Acid 30% aqueous sol. | — | — | — | 3,0 | — | — | — | — | — | — |
| Clinnbazole (Crinipan AD) | — | — | — | — | — | — | — | 0,5 | — | — |
| Cocannide MEA (Mackannide CMA) | — | — | — | — | — | — | — | 3,0 | — | — |
| Cocannide MIPA | 0,5 | — | — | — | — | — | — | — | — | — |
| Cocoannidopropyl Betaine (Tego Betain F50) | 15,0 | 5,0 | 3,0 | 6,0 | 14,0 | — | 15,0 | 17,0 | — | — |
| Coco Betaine (Dehyton AB30) | — | — | — | — | — | 2,0 | — | — | — | — |
| Coco-Glucoside (Plantacare 818 UP) | — | 10,0 | — | — | — | — | — | — | — | — |
| Decyl Glycoside (Ecosense 3000) | — | — | — | — | 2,0 | — | — | — | — | — |
| Disodiunn Cocoyl Glutamate (Plantapon ACGLC) | — | 3,0 | — | — | — | — | — | — | — | — |
| Disodiunn EDTA (EDTABD) | — | — | — | — | — | — | — | 0,1 | — | — |

TABLE 59-continued (in w/w %) Further preferred cleansing formulations without sodium lauryl ether sulfate (SLES).
1: Mild Hair & Body Wash; 2: Shampoo; 3: Anti Acne Face Wash; 4: Color Care Shampoo; 5: Feminine Wash; 6: Micellar Water; 7: Liquid soap; 8: Antidandruff Shampoo; 9: Baby Shampoo; 10: Solid shampoo.

| INCI | 1 | 2 | 3 | 4 | 5 | 6 | 7 | 8 | 9 | 10 |
|---|---|---|---|---|---|---|---|---|---|---|
| Disodiunn Lauryl Sulfosuccinate (Setacin F spezial) | — | — | 2,0 | 2,0 | — | — | — | — | — | — |
| Fragrance PO1, PO2, PO3, PO4, or PO5 | 1,0 | 0,5 | 0,1 | 0,3 | 0,1 | 0,3 | 0,5 | 0,3 | 0,05 | — |
| Glycerin 99% | — | — | 0,5 | — | 3,0 | — | — | — | — | — |
| Glycerin, Aqua, Hamamelis Virginia Bark/Leaf/Twig Extract (Extrapone Witch Hazel GVV) | — | — | — | — | 1,0 | — | — | — | — | — |
| Glyceryl Caprylate (Synnlite G8) | 0,1 | 0,5 | 0,2 | 0,3 | 0,5 | 0,1 | — | — | — | — |
| Glycol Distearate, Laureth-4, Cocoannidopropyl Betaine (Quickpearl PK3) | — | — | — | 2,0 | — | — | — | 3,0 | — | — |
| Hydroxyacetophenone (Synnsave H) | 0,5 | 0,6 | — | — | — | 0,5 | — | 0,5 | — | — |
| Isostearannide MIPA, Glyceryl Laurate (Antil SPA80) | — | — | — | 1,0 | — | — | — | — | — | — |
| Kaolin (ImerCaree 02K-S) | — | — | — | — | — | — | — | — | — | 18,8 |
| Lactic Acid 90% aqueous sol. | — | — | — | — | 0,3 | — | — | — | — | — |
| Lauroyl /Myristoyl Methyl Glucamide (Glucotain Clean) | 12,0 | — | — | — | — | — | — | — | — | — |
| Lauryl Hydroxysultaine (45% AS) | — | — | — | — | — | — | 11,0 | — | — | — |
| Lauryl Lactate (Schercennol LL Ester) | — | — | — | — | — | — | 0,3 | — | — | — |
| Maltodextrin, Lactobacillus Ferment (SymReboot L19) | — | — | — | — | — | — | — | — | — | 0,5 |
| Menthyl Lactate (Frescolat ML) | — | — | — | — | — | — | — | 0,2 | — | — |
| PEG-200 Hydrogenated Glyceryl Palmate, PEG-7 Glyceryl Cocoate (Antil 200) | — | — | — | 4,5 | — | — | — | — | — | — |
| PEG-4 Rapeseedannide (92% AS) | — | — | — | — | — | — | 2,0 | — | 2,8 | — |
| PEG-40 Hydrogenated Castor Oil, Trideceth-9, Propylene Glycol, Aqua (Solubilizer Synnrise) | — | — | — | — | 1,5 | — | — | 0,9 | — | — |
| PEG-45 M (PolyoxWSR N60K) | — | — | — | — | — | — | — | 0,15 | — | — |
| Pentylene Glycol (Hydrolite-5 Green) | — | — | — | — | — | 2,0 | — | — | — | 1,5 |
| Pentylene Glycol, 4-t-Butylcyclohexanol (Symsitive 1609) | — | — | — | — | 1,0 | — | — | — | — | — |
| Pentylene Glycol, Butylene Glycol, Hydroxyphenyl Propannidobenzoic Acid (SynnCalmin) | — | — | — | — | 1,0 | — | — | 2,0 | — | — |
| Phenyl Propanol, O-Cynnen-5-ol, Decylene Glycol (Synnguard CD) | — | — | — | — | 0,5 | — | — | — | — | — |
| Piroctone Olamine (Octopirox) | 0,1 | — | 0,5 | — | — | — | — | — | — | — |
| Polyacrylate 33 (Rheonner33T) | — | — | — | — | — | — | — | 6,5 | — | — |
| Polyguaterniunn-10 (Polymer JR 400) | — | — | — | 0,3 | — | — | — | 0,2 | — | — |
| Polyguaterniunn-7 (Dehyguart CC7) | 0,4 | — | — | — | — | — | — | — | — | — |
| Polysilicone-19 (Abil UV Quat 50) | — | — | — | 2,0 | — | — | — | — | — | — |
| Potassium Sorbate | — | — | 0,3 | 0,4 | — | 0,5 | — | — | — | 0,3 |
| Propylene Glycol | — | — | — | — | 3,0 | — | — | — | — | — |
| Rhannnose | — | — | — | — | 0,5 | — | — | — | — | — |

TABLE 59-continued (in w/w %) Further preferred cleansing formulations without sodium lauryl ether sulfate (SLES).
1: Mild Hair & Body Wash; 2: Shampoo; 3: Anti Acne Face Wash; 4: Color Care Shampoo; 5: Feminine Wash; 6: Micellar Water; 7: Liquid soap; 8: Antidandruff Shampoo; 9: Baby Shampoo; 10: Solid shampoo.

| INCI | 1 | 2 | 3 | 4 | 5 | 6 | 7 | 8 | 9 | 10 |
|---|---|---|---|---|---|---|---|---|---|---|
| Sodium C14-C16 Olefin Sulfonate (38% AS) | — | — | — | — | — | — | 27,0 | — | — | — |
| Sodium Chloride | 0,5 | — | — | — | — | — | — | — | — | — |
| Sodium Cocoannphoacetate (Rewoteric AMC) | — | — | — | 6,0 | — | — | — | — | — | — |
| Sodium Cocoyl Alaninate (Annilite ACS 12) | — | — | — | — | 2,0 | — | — | — | — | — |
| Sodium Cocoyl Glutamate (Hostapon CCG) | — | 5,0 | 3,0 | — | — | — | — | — | — | — |
| Sodium Cocoyl Glycinate (Hostapon SG) | 10,0 | — | — | — | — | — | — | — | — | — |
| Sodium Cocoyl Isethionate (ELFAN @AT 84) | 4,5 | — | — | — | — | — | — | — | — | 15,0 |
| Sodium Hydroxide (50% aqueous sol.) | — | — | — | — | — | — | — | 0,5 | — | — |
| Sodium Laureth-5 Carboxylate (Akypo Foam RL 40) | — | — | — | — | — | — | — | — | 8,0 | — |
| Sodium Laureth-6 Carboxylate (Akypo SOFT 45 HP) | — | — | — | — | 1,0 | — | — | — | — | — |
| Sodium Lauroyl Glutamate (Hostapon CLG) | 3,0 | — | — | — | — | — | — | — | — | — |
| Sodium Lauroyl Lactylate (Dermnosoft SLL) | — | — | — | — | 2,0 | — | — | — | — | — |
| Sodium Lauroyl Methyl Isethionate (Iselux LQ-CLRSB) | — | — | — | 22,0 | — | — | — | — | — | — |
| Sodium Lauroyl Sarcosinate (Protelan LS9011) | — | 3,0 | — | 3,0 | — | — | — | — | — | — |
| Sodium Lauryl Glucose Carboxylate Lauryl Glucoside (Plantapon LGC Sorb) | — | — | — | — | — | — | — | 6,0 | — | — |
| Sodium Myristoyl Glutamate (Annisoft MS11) | — | — | — | — | — | — | — | — | — | 30,0 |
| Sodium Salicylate (Seboclear) | — | — | 0,3 | — | — | — | — | — | — | — |
| Sorbitol | 1,0 | — | — | — | — | — | — | — | — | — |
| Trideceth-9, PEG-5 Isononanoate, Water (Aqua) | — | — | — | — | — | — | — | 2,0 | — | — |
| Water (Aqua), Glycerin, Tetraselnnis Suecica Extract (SynnControl Care) | — | — | 1,0 | — | — | — | — | — | — | — |
| Xanthan Gum (Keltrol RD) | — | 0,5 | — | — | 0,5 | — | — | — | — | — |
| Water (Aqua) | | | | | Ad 100 | | | | | |

Example: Influence of 3-Hydroxypropyl Caprylate on Foam Properties in Bar Soap & Shampoo Formulations Example 1 vs Comparable Placebo Sample 2

3-Hydroxypropyl caprylate was incorporated with 0.5; 1.0 and 2.0 w/w % into a commercially available bar soap (Soap Base Hirtler*, INCI: Sodium Tallowate, Sodium Cocoate, Sodium Palm Kernelate, Aqua, Glycerin, Sodium Chloride, Tetrasodium Etidronate).

Examples A2; A3 and A4 are in accordance with the invention, example A1 is the soap base without active and serves for comparison (cf, Table 60).

TABLE 60

| Bar soaps | A1 | A2 | A3 | A4 |
|---|---|---|---|---|
| Soap Base Hirtler* | 100.0 | — | — | — |
| 3-Hydroxypropyl Caprylate | | 0.5 | 1.0 | 2.0 |
| sum | | 100.0 | | |

Production Method Bar Soap Solutions 200 ml of the corresponding bar soap solutions were prepared by stirring with a vane stirrer (0.2 w/w % bar soap A1, A2, A3 and A4, according to table 1 in water demineralized). The solutions were transferred (each by each) into the foam volume and drainage measuring instrument (Ernst Haage; cf. FIG. 4). Then, the stamp is pulled up and pushed down in constant intervals (40 swings). The volume of the foam and the drainage formation was recorded (cf. Table 61).

TABLE 61

| Bar soap solutions | A1S | A2S | A3S | A4S |
|---|---|---|---|---|
| Bar soap A1 | 0.2 | — | — | — |
| Bar soap A2 | — | 0.2 | — | — |
| Bar soap A3 | — | — | 0.2 | — |
| Bar soap A4 | — | — | — | 0.2 |
| sum | | 100.0 | | |

Results Foam Volume

The results of foam volume measurements after 40 swings treatment of solutions A1S, A2S, A3S and A4S are included in Table 62 (double determination).

TABLE 62

| | | Conc. 3-Hydroxypropyl Caprylate | 40 swings | MW |
|---|---|---|---|---|
| Foam volume [ml] | 1. Measurement | Placebo (A1S) | 500 | 450 |
| | 2. Measurement | | 400 | |
| | 1. Measurement | 0.5% (A2S) | 600 | 550 |
| | 2. Measurement | | 500 | |
| | 1. Measurement | 1% (A3S) | 700 | 700 |
| | 2. Measurement | | 700 | |
| | 1. Measurement | 2% (A4S) | 900 | 800 |
| | 2. Measurement | | 700 | |

It could be clearly demonstrated that the increasing concentration of 3-Hydroxypropyl caprylate leads to a higher foam volume.

Results of Drainage Liquid Determination

After evaluating the foam volume, the formation of drainage liquid in the drainage measurement device (cf. FIG. 4) was observed after 0, 15, 30, 60 and 180 seconds (cf. Table 63). The formation of drainage liquid corresponds directly to the breaking of the foam bubbles. High volume of drainage liquid corresponds to quick breaking foam and therefore less foam stability.

TABLE 63

| | Conc. 3-Hydroxypropyl Caprylate | Drainage liquid [ml] | | | | | | MW (300 s) |
|---|---|---|---|---|---|---|---|---|
| | | 0 s | 15 s | 30 s | 60 s | 180 s | 300 s | |
| 1. Measurement | Placebo | 0 | 5 | 10 | 25 | 40 | 80 | 77, 5 |
| 2. Measurement | (A1S) | 5 | 5 | 15 | 25 | 50 | 75 | |
| 1. Measurement | 0,5% | 0 | 0 | 0 | 0 | 10 | 25 | 27, 5 |
| 2. Measurement | (A2S) | 0 | 0 | 0 | 5 | 15 | 30 | |
| 1. Measurement | 1% | 0 | 0 | 0 | 15 | 25 | 50 | 45, 0 |
| 2. Measurement | (A3S) | 0 | 0 | 0 | 5 | 20 | 40 | |
| 1. Measurement | 2% | 0 | 0 | 0 | 0 | 25 | 40 | 35, 0 |
| 2. Measurement | (A4S) | 0 | 0 | 0 | 0 | 20 | 30 | |

It could be clearly demonstrated that with increasing concentration of 3-Hydroxypropyl caprylate less drainage liquid was formed. Less drainage liquid indicates better foam stability.

Sulfate Free Shampoos

The most commonly used sulfate compounds within the cosmetic industry are sodium laureth sulfate, sodium lauryl sulfate, and ammonium laureth sulfate. They are widely used in combinations with other surfactants to reduce irritation. Especially for color-treated, dry hair & dry scalp there is a tendency to use mild sulfate free formulations.

Very often these formulations tend to poor foaming properties vs sulfate based formulations. Additionally, sulfate based shampoos can easily thickened by sodium chloride, which does not work well with sulfate free surfactants. Increasing the viscosity is therefore a further challenge for sulfate free formulations.

Formulations were prepared by blending all ingredients (cf. Table 64) through warming up to 40° C. The stirring was continued until the blend was clear. The pH value was adjusted to pH 5.5 to 5.8.

TABLE 64

(amounts given in w/w %)

| | INCI | Placebo 01_A | 1% 3-Hydroxypropyl Caprylate 01_B |
|---|---|---|---|
| Phase A | | | |
| Plantacare 1200 UP (AS 52%) | Lauryl Glucoside | 11.4 | 11.4 |
| Phase B | | | |
| Plantacare 818 (AS 52%) | Coco Glucoside | 5.6 | 5.6 |
| Water | Water (Aqua) | Ad 100 | Ad 100 |
| TEGOSOFT ® LSE 65 K Soft (AS 65%) | Sucrose Cocoate | 1.5 | 1.5 |
| TEGO ® Betain F 50 (AS 38%) | Cocamido-propyl Betaine | 18.0 | 18.0 |
| 3-Hydroxypropyl Caprylate | Propanediol Caprylate | — | 1.0 |
| SUM | | | 100.0 |

The results are summarized in Table 65. As can be gathered from this table, an increased foam volume was obtained with shampoo containing 3-Hydroxypropyl caprylate.

TABLE 65

| | | Conc. 3-Hydroxy-propyl Caprylate | 60 swings | MW |
|---|---|---|---|---|
| foam volume [ml] | 1. Measurement | Placebo 01_A | 800 | 800 |
| | 2. Measurement | | 800 | |
| | 1. Measurement | 1% 3-Hydroxy-propyl Caprylate 01_B | 850 | 850 |
| | 2. Measurement | | 850 | |

In another round of experiments, the formulations as shown in Table 66 were prepared by blending all ingredients using the same methodology as before.

TABLE 66

(w/w %)

| | INCI | Placebo 02_A | 0.5% 3-Hydroxypropyl Caprylate 02_B |
|---|---|---|---|
| Phase A | | | |
| Plantacare 1200 UP (AS 52%) | Lauryl Glucoside | 5.7 | 5.7 |
| Phase B | | | |
| Plantacare 818 (AS 52%) | Coco Glucoside | 2.8 | 2.8 |
| Water | Water (Aqua) | 55.5 | 55.0 |
| Plantapon SF (AS 30%) | Sodium Cocoamphoacetate (and) Glycerin (and) Lauryl Glucoside (and) Sodium Cocoyl Glutamate (and) Sodium Lauryl GlucoseCarboxylate | 18.0 | 18.0 |
| TEGO ® Betain F 50 (AS 38%) | Cocannidopropyl Betaine | 18.0 | 18.0 |
| 3-Hydroxypropyl Caprylate | Propanediol Caprylate | — | 0.5 |
| SUM | | | 100.0 |

The results are summarized in Table 67. As can be gathered from this table, an increased foam volume was obtained with shampoo containing 3-Hydroxypropyl caprylate.

TABLE 67

| | | Conc. 3-Hydroxypropyl Caprylate | 60 swings | MW |
|---|---|---|---|---|
| foam volume [ml] | 1. Measurement | Placebo 02_A | 1000 | 1000 |
| | 2. Measurement | | 1000 | |
| | 1.Measurement | 0.5% 3-Hydroxypropyl Caprylate 02_B | 1100 | 1150 |
| | 2. Measurement | | 1200 | |

In yet another round of experiments, the formulations as shown in Table 68 were prepared by blending all ingredients using the same methodology as before.

TABLE 68

(w/w %): Sulfate free shampoo/evaluation of viscosity

| | INCI | Placebo 03_A | 0.5% 3-Hydroxypropyl Caprylate 03_B |
|---|---|---|---|
| Phase A | | | |
| Plantacare 1200 UP (AS 52%) | Lauryl Glucoside | 10.2 | 10.2 |
| Hostapon CT Paste ex Clariant (AS 30%) | Sodium Cocoyl Taurate | 6.5 | 6.5 |
| Phase B | | | |
| Plantacare 818 (AS 52%) | Coco Glucoside | 5.0 | 5.0 |

TABLE 68-continued (w/w %): Sulfate free shampoo/evaluation of viscosity

| | INCI | Placebo 03_A | 0.5% 3-Hydroxypropyl Caprylate 03_B |
|---|---|---|---|
| Water demin. | Water (Aqua) | 60.3 | 59.8 |
| TEGO ® Betain F 50 (AS 38%) | Cocamidopropyl Betaine | 18.0 | 18.0 |
| 3-Hydroxypropyl Caprylate | Propanediol Caprylate | — | 0.5 |
| SUM | | | 100.0 |

The viscosity was determined using the following parameters:

Rheostress1

C60/1° Ti L L12096; 0.05 mm crack

Shear frequency ý [1/s]: 5

The results of viscosity measurements are summarized in Table 70. It could be clearly demonstrated that a significant increased viscosity was obtained with 3-Hydroxypropyl caprylate vs placebo.

TABLE 69

(results of viscosity measurements)

| | Viscosity η [mPas] | | |
|---|---|---|---|
| Substance | 1 | 2 | MW |
| Placebo (03_A) | 2269 | 2234 | 2252 |
| 0.5% 3-Hydroxypropyl Caprylate 0,3_B | 7449 | 7430 | 7410 |

The invention claimed is:

1. A skin or hair care product comprising one or more fatty acid esters that increase viscosity, foam stability, or foam volume of the product, wherein the one or more fatty esters are chosen from 3-hydroxypropyl caprylate and 3-hydroxypropyl undecylenate and are in an amount sufficient to increase the viscosity, the foam stability, or the foam volume.

2. The product according to claim 1, wherein the product is a leave-on product or.

3. The product according to claim 1, wherein the one or more fatty acid esters prevent and/or reduce dandruff, and are in an amount sufficient to prevent and/or reduce the dandruff.

4. A method for increasing viscosity, foam stability, or foam volume of a skin or hair care product comprising:
   (i) providing the ingredients of a skin or hair care product,
   (ii) providing one or more fatty acid esters chosen from 3-hydroxypropyl caprylate and 3-hydroxypropyl undecylenate
   (iii) mixing the components of (i) and (ii).

5. The method according to claim 4, wherein the product is a rinse-off product.

6. The method according to claim 4, wherein the product is an anti-dandruff shampoo and the one or more fatty acid esters are in an amount sufficient to prevent and/or reduce dandruff.

7. A method for manufacturing a skin or hair care product comprising:

(i) providing ingredients of a skin or hair care product,
(ii) providing one or more fatty acid esters chosen from 3-hydroxypropyl caprylate and 3-hydroxypropyl undecylenate, and
(iii) mixing the ingredients of (i) with the one or more fatty acid esters of (ii).

8. The method according to claim 7, wherein the product is an anti-dandruff shampoo and the one or more fatty acid esters are in an amount sufficient to prevent and/or reduce dandruff.

9. The product according to claim 1, wherein the product is sulfate-free.

10. The product according to claim 1, wherein the product is a shampoo comprising:
(i) one or more surfactant(s) chosen from sodium lauryl ether sulfate, cocamidopropyl betaine, lauryl glucoside, caprylyl/capryl glucoside, sodium lauryl sulfate, disodium laureth sulfosuccinate, sodium lauryl sulfoacetate, decyl glucoside, sodium lauroyl sarcosinate, glycol distearate, coco-betaine, PPG-5-ceteth-20, coco-glucoside, diethylhexyl sodium sulfosuccinate, ammonium cocoyl isethionate, ammonium cocoyl sarcosinate, diethylhexyl sodium sulfosuccinate, cocamide-MEA, PEG-7 glyceryl cocoate, glycol distearate, sodium oleoyl sarcosinate, sodium cocoyl isethionate, sodium cocoamphoacetate, sodium cocoyl glutamate, and sodium methyl cocoyl taurate, cocamide MIPA, disodium cocoyl glutamate, disodium lauryl sulfosuccinate, lauroyl/myristoyl methyl glucamide, sodium C14-C16 olefin sulfonate, sodium cocoamphoacetate, sodium cocoyl alaninate, sodium cocoyl glutamate, sodium cocoyl glycinate, sodium cocoyl isethionate, sodium laureth-5 carboxylate, sodium laureth-6 carboxylate, sodium lauroyl glutamate, sodium lauroyl lactylate, sodium lauroyl methyl isethionate, laureth-4, isostearamide MIPA, lauryl hydroxysultaine, PEG-200 hydrogenated glyceryl palmate, PEG-4 rapeseedamide, PEG-40 hydrogenated castor oil, trideceth-9, and sodium lauroyl sarcosinate,
(ii) optionally water,
(iii) one or more fatty acid esters chosen from 3-hydroxypropyl caprylate and 3-hydroxypropyl undecylenate
(iv) optionally, one or more fragrance(s),
(v) optionally, one or more plant oil(s) chosen from *Persea gratissima* oil, *Olea europaea* oil, *Prunus amygdalus dulcis* oil, *Helianthus annuus* seed oil, *Simmondsia chinensis* seed oil, *Mauritia flexuosa* fruit oil, *Calophyllum inophyllum* seed oil and *Triticum vulgare* germ oil,
(vi) optionally, one or more preservative(s) chosen from 2-phenoxyethanol, benzyl alcohol, dehydroacetic acid, methyl paraben, sorbic acid, and benzoic acid, and
(vii) optionally, one or more active ingredient(s) chosen from 4-hydroxyacetophenone, 1,2-pentanediol, 1,2-hexanediol, 1,2-octanediol, 1,2-decanediol, caprylhydroxamic acid, sorbitan caprylate, and ethylhexylglycerine.

11. The product according to claim 10, wherein the shampoo is sulfate-free.

12. The product according to claim 1, wherein the product is a hair or body cream comprising:
(i) water,
(ii) one or more emulsifying agent(s) chosen from PEG-100 stearate, cetearyl glycoside, distearyldimonium chloride, palmitamidopropyltrimonium chloride, glyceryl stearate citrate, glyceryl oleate citrate, polyglyceryl-3 methylglucose distearate, cetearyl alcohol, potassium cetyl phosphate, sodium cetyl phosphate, acrylates/C10-30 alkyl acrylate cross-polymer, ammonium acryloyldimethyltaurate/Beheneth-25 methacrylate crosspolymer, polyglyceryl-4 caprate, polyglyceryl-4 caprylate/caprate, cetyl PEG/PPG-10/1, dimethicone, polyglycer-yl-6 dioleate, polyglyceryl-2 stearate, PEG-30 dipoly-hydroxystearate, sodium stearoyl lactylate, xanthan gum, dehydro xanthan gum, hydrogenated palm glycerides, polyglyerol-3 oleate, polyglyceryl-3 polyricinoleate, sodium caproyl/lauroyl lactylate, glyceryl stearate se, polyglyceryl-3 dicitrate/stearate, and PEG-40 hydrogenated castor oil,
(iii) one or more oil body/bodies chosen from caprylic capric triglycerides, mineral oil, *Simmondsia chinensis* seed oil, *Butyrospermum parkii* butter, dicaprylyl ether, cyclomethicone, dimethicone, C12-15 alkyl benzoate, isopropyl palmitate, isopropyl myristate, octyldodecanol, cetearyl ethylhexanoate, cetearyl nonanoate, ethylhexyl isononanoate, propylene glycol dicaprylate/dicaprate, propylheptyl caprylate, decyl oleate, hexyl laurate, ethylhexyl stearate, triisononanoin, iso-adipate, stearyl heptanoate, and stearyl caprylate,
(iv) one or more fatty acid esters chosen from 3-hydroxypropyl caprylate and 3-hydroxypropyl undecylenate,
(v) one or more fragrance(s),
(vi) one or more preservative(s) chosen from 2-phenoxyethanol, benzyl alcohol, dehydroacetic acid, methyl paraben, sorbic acid, and benzoic acid, and
(vii) one or more active ingredient(s) chosen from 4-hydroxyacetophenone, 1,2-pentanediol, 1,2-hexanediol, 1,2-octanediol, 1,2-decanediol, caprylhydroxamic acid, sorbitan caprylate, and ethylhexylglycerine.

13. The product according to claim 1, wherein the product is a soap comprising:
(i) one or more surfactant(s) chosen from sodium lauryl ether sulfate, cocamidopropyl betaine, lauryl glucoside, caprylyl/capryl glucoside, sodium lauryl sulfate, disodium laureth sulfosuccinate, sodium lauryl sulfoacetate, decyl glucoside, glycol distearate, coco-betaine, PPG-5-ceteth-20, coco-glucoside, diethylhexyl sodium sulfosuccinate, ammonium cocoyl isethionate, ammonium cocoyl sarcosinate, diethylhexyl sodium sulfosuccinate, cocamide-MEA, PEG-7 glyceryl cocoate, glycol/distearate, sodium oleoyl sarcosinate, sodium cocoyl isethionate, sodium cocoamphoacetate, sodium cocoyl glutamate, and sodium methyl cocoyl taurate, cocamide MIPA, disodium cocoyl glutamate, disodium lauryl sulfosuccinate, lauroyl/myristoyl methyl glucamide, sodium C14-C16 olefin sulfonate, sodium cocoamphoacetate, sodium cocoyl alaninate, sodium cocoyl glutamate, sodium cocoyl glycinate, sodium cocoyl isethionate, sodium laureth-5 carboxylate, sodium laureth-6 carboxylate, sodium lauroyl glutamate, sodium lauroyl lactylate, sodium lauroyl methyl isethionate laureth-4, isostearamide MIPA, lauryl hydroxysultaine, PEG-200 hydrogenated glyceryl palmate, PEG-4 rapeseedamide, PEG-40 hydrogenated castor oil, trideceth-9, sodium cocoate, sodium stearate, sodium oleate, sodium palmitate, sodium linoleate, sodium laurate, sodium linoleate, sodium myristate, sodium isethionate, sodium lauroyl isethionate, stearic acid, sodium palmitate, lauric acid, aqua, sodium isethionate, sodium stearate, cocamidopropyl betaine, sodium palm kernelate, glycerin, parfum, sodium chloride, zinc oxide, tetrasodium EDTA, tetrasodium etidronate, alumina, alpha-isomethyl ionone, benzyl alcohol, butylphenyl methylpropionalpotassium palm kernelate, sodium palmate, potassium palmate, sodium castorate, sodium carbonate, sodium isostearoyl lactylate, sodium dodecylbenzenesulfonate, sodium palm kernelate, lanolin, lecithin, silica, talc, glycerin, sodium lauroyl isethionate, sodium sulfate, sodium laureth sulfate, glycerin, sodium tallowate, stearic acid, palm acid, palm kernel acid, coconut acid, lauric acid, PEG-4, PEG-20, alpha olefin sulfonate, glycerol monostearate, cetostearyl alcohol, paraffin wax, sodium cocoamphoacetate, sodium cocoyl isethionate, disodium lauryl sulfosuccinate, sodium laureth-5 carboxylate, cetearyl alcohol, glyceryl stearate, paraffin, disodium lauryl sulfosuccinate, glyceryl stearate, palmitic acid, stearic acid, lanolin, lecithin, cetyl palmitate, and sodium lauroyl sarcosinate, (ii) optionally water,
(iii) one or more fatty acid esters chosen from 3-hydroxypropyl caprylate and 3-hydroxypropyl undecylenate,
(iv) one or more fragrance(s),
(v) one or more plant oil(s) chosen from *Persea gratissima* oil, *Olea europaea* oil, *Prunus amygdalus dulcis* oil, *Helianthus annuus* seed oil, *Simmondsia chinensis* seed oil, *Mauritia flexuosa* fruit oil, *Calophyllum inophyllum* seed oil and *Triticum vulgare* germ oil,
(vi) one or more preservative(s) selected from the group consisting of 2-phenoxyethanol, benzyl alcohol, dehydroacetic acid, methyl paraben, sorbic acid, and benzoic acid, and
(vii) one or more active ingredient(s) chosen from 4-hydroxyacetophenone, 1,2-pentanediol, 1,2-hexanediol, 1,2-octanediol, 1,2-decanediol, caprylhydroxamic acid, sorbitan caprylate, and ethylhexylglycerine.

14. The product according to claim 1, wherein the product is in the form of an oil-in-water emulsion, a water-in-oil emulsion, an aqueous formulation, or an aqueous and/or ethanolic and/or glycolic-based formulation.

15. The product according to claim 1, wherein the product is a rinse-off product.

16. The rinse-off product according to claim 15, wherein the rinse-off product is a surfactant-based cleansing product.

17. The rinse-off product according to claim 15, wherein the product is an anti-dandruff shampoo.

18. The surfactant-based cleansing product according to claim 16, wherein the product is sulfate-free.

19. The skin or hair care product of claim 1, wherein the product further comprises one or more fatty acid esters selected from glyceryl monocaprylate and glyceryl monoundecylenate.

20. The product of claim 9, wherein the product comprises sodium cocoyl isethionate, sodium cocoamphoacetate, sodium cocoyl glutamate, sodium methyl cocoyl taurate, sodium cocoyl isethionate, sodium cocoamphoacetate, sodium cocoyl glutamate, and sodium methyl cocoyl taurate, cocamide MIPA, disodium cocoyl glutamate, disodium lauryl sulfosuccinate, lauroyl/myristoyl methyl glucamide, sodium C14-C16 olefin sulfonate, sodium cocoamphoacetate, sodium cocoyl alaninate, sodium cocoyl glutamate, sodium cocoyl glycinate, sodium cocoyl isethionate, sodium laureth-5 carboxylate, sodium laureth-6 carboxylate, sodium lauroyl glutamate, sodium lauroyl lactylate, sodium lauroyl methyl isethionate, coco-glucoside, decyl glucoside, lauryl glucoside, cocamide MEA, cocoamidopropyl betaine, coco betaine, glycol distearate, laureth-4, isostearamide MIPA, lauryl hydroxysultaine, PEG-200 hydrogenated glyceryl palmate, PEG-7 glyceryl cocoate, PEG-4 rapeseedamide, PEG-40 hydrogenated castor oil, trideceth-9, sodium lauroyl sarcosinate, or a combination thereof.

* * * * *